United States Patent [19]  [11] Patent Number: 4,826,530
Lee  [45] Date of Patent: May 2, 1989

[54] 2,6-SUBSTITUTED PYRIDINE COMPOUNDS

[75] Inventor: Len F. Lee, St. Charles, Mo.

[73] Assignee: Monsanto Company, St. Louis, Mo.

[21] Appl. No.: 62,012

[22] Filed: Jun. 15, 1987

Related U.S. Application Data

[60] Division of Ser. No. 602,021, Apr. 29, 1984, Pat. No. 4,692,184, which is a continuation-in-part of Ser. No. 522,430, Aug. 11, 1983, abandoned.

[51] Int. Cl.$^4$ .................. C07D 213/80; A01N 43/40
[52] U.S. Cl. ............................................ 71/94; 71/90; 546/321; 546/316; 546/286; 546/283; 546/257; 546/284; 546/268; 546/275; 546/315; 546/318; 546/322

[58] Field of Search ...................... 71/94, 90; 546/321, 546/316, 286, 283, 257, 284, 268, 275, 315, 318, 322

[56] References Cited

U.S. PATENT DOCUMENTS 4,698,093 10/1987 Lee et al. ............................ 546/275

Primary Examiner—Jane T. Fan
Attorney, Agent, or Firm—James C. Bolding

[57] ABSTRACT

There are disclosed novel 2,6-substituted-3,5-pyridinedicarboxylic acids, esters, salts, amides, halides, and cyano compounds useful as herbicides, and as intermediates which provide herbicides.

56 Claims, No Drawings

2,6-SUBSTITUTED PYRIDINE COMPOUNDS

This application is a divisional of copending U.S. application Ser. No. 602,021 filed Apr. 29, 1984, now U.S. Pat. No. 4,692,184 which is a continuation-in-part of U.S. application Ser. No. 522,430 filed Aug. 11, 1983 now abandoned.

This invention relates to a new class of 2,6-substituted-3,5-pyridinedicarboxylic acid derivatives having a wide range of activity as herbicides.

Pyridine derivatives have, for many years, been investigated for use in the biological sciences. For example, 2,6-bis-(trifluoromethyl)-4-pyridinols have been found useful as herbicides and fungicides as disclosed in U.S. Pat. No. 3,748,334. Such compounds are characterized by substitution in the 4-position by a hydroxyl radical. In addition to the hydroxyl radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO Pat. No. 44,262 there is disclosed 2,6-dialkyl-3-phenylcarbamyl-5-pyridinecarboxylates and -5-cyano-compounds useful as herbicides. There is no disclosure of the 2-haloalkyl radicals nor any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4 position is occupied by a silver salt, U.S. Pat. No. 1,944,412 discloses that such compounds have been utilized in the production of X-ray pictures with intraveneous injection of such compounds.

BRIEF DESCRIPTION OF THE INVENTION

It is an object of this invention to provide herbicidal methods utilizing the novel pyridines of this invention.

Another object of this invention is to provide novel methods for preparing the novel compounds of this invention and novel intermediates useful therein.

The novel compounds of this invention are useful as herbicides or intermediates which provide herbicides and represented by Formula I

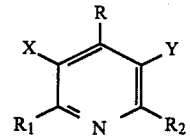

wherein:

R is selected from the group consisting of lower alkyl, lower alkenyl, lower alkynyl, lower alkenylalkyl, haloalkyl, haloalkenyl, $C_{3-7}$ cycloalkyl, $C_{3-6}$ cycloalkanylalkyl, $C_{3-6}$ cycloalkenyl, aryl, arylmethyl, alkoxyalkyl, benzyloxymethyl, alkylthioalkyl, dialkoxyalkyl, (1-alkoxy-1-alkylthio)alkyl, aminoalkyl, alkylaminoalkyl, dialkylaminoalkyl, alkylsulfonylalkyl, alkylsulfinylalkyl, alkyl substituted with a dialkyl sulfonium salt, cyanoalkyl, carbamylalkyl, carbalkoxyalkyl, carbalkoxyalkenyl, formylalkyl, dialkylaminoalkenyl, saturated and unsaturated heterocyclic radicals having from 3 to 6 atoms in the ring including from 1 to 3 hetero atoms selected from O, S, and N, and wherein the radical is joined to the pyridine ring by a C—C bond, and lower alkyl substituted with a saturated or unsaturated heterocyclic radical wherein the hetero atom is selected from O, S, and N;

$R_1$ and $R_2$ are independently selected from alkyl, fluorinated methyl, and chlorofluorinated methyl radicals, provided that one of $R_1$ and $R_2$ must be a fluorinated methyl or chlorofluorinated methyl radical; and X and Y are independently selected from the group consisting of

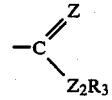

wherein Z is selected from O and $NR_7$ and where $R_7$ is hydrogen or lower alkyl, and wherein $Z_2$ is selected from O and S wherein $R_3$ in each occurrence is independently selected from hydrogen, alkyl $C_{1-4}$, alkenylalkyl $C_{3-4}$, haloalkyl $C_{1-4}$, cycloalkanylalkyl, cyanoalkyl, or alkynylalkyl $C_{3-4}$;

wherein
$R_4$ is selected from hydrogen and halogen,

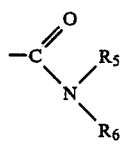

wherein
$R_5$ and $R_6$ are independently selected from
hydrogen, lower alkyl, and phenyl; —CH$_2$OH; and —C≡N.

Compounds of this invention which are of particular interest as herbicides include those of the above Formula I wherein X and Y are both ester groups in which $R_3$ in each ester group is independently an alkyl group having 1-3 carbon atoms. Of these preferred 3, 5 diester compounds, a more preferred grouping in those compounds in which $R^1$ and $R_2$ are dissimilar fluorinated methyl radicals; and within this more preferred grouping, the most preferred compounds are those which R is an alkyl or alkylthioalkyl substituent having 1-5 carbon atoms.

The term "alkyl" means herein both straight and branched chain radicals which include, but are not limited to, ethyl, methyl, n-propyl, 1-ethylpropyl, 1-methylpropyl, n-butyl, 2,2-dimethylpropyl, pentyl, isobutyl, isopropyl. The term "cycloalkyl" is intended to mean cycloalkyl radicals such as cyclopropyl, cyclobutyl, cyclopentyl, cyclohexyl, and cycloheptyl.

The term "lower alkyl" herein means an alkyl radical having 1 to 7 carbon atoms. The terms "lower alkenyl" and "lower alkynyl" herein mean alkenyl and alkynyl groups having 2 to 7 carbon atoms. Examples of such alkenyl groups include ethenyl, 1-propenyl, 2-propenyl, 1-butenyl, 2-butenyl, 3-butenyl, 2-methyl-1-propenyl, 2-methyl-2-propenyl, 1-methylethenyl, and the like. Examples of such lower alkynyl groups include ethynyl, 1-propynyl, 2-propynyl, and so forth.

The term "saturated and unsaturated heterocyclic radicals" means heterocyclic radicals having from 3 to 6 atoms in the ring including from 1 to 3 hetero atoms selected from O, S, and N, and typically include, but are not limited to, furyl, pyridyl, thienyl, thiiranyl, oxiranyl, and aziridinyl.

The term "cycloalkanylalkyl" is intended to mean alkyl radicals substituted with a $C_{3-6}$ cycloalkyl radical. The term "haloalkyl" is intended to mean alkyl radicals substituted with one or more halogen atoms.

The term "fluorinated methyl" means herein methyl radicals having one or more fluorine atoms attached thereto including radicals wherein all hydrogen atoms substituted by fluorine.

The term "chlorofluorinated methyl" means herein a methyl radical having at least one hydrogen substituted by fluorine and at least one other hydrogen substituted by chlorine.

DETAILED DESCRIPTION OF THE INVENTION PREPARATION OF SYMMETRICAL PYRIDINES

Scheme I below describes a method whereby symmetrical pyridines (D) of this invention may be produced. They are conveniently obtained from dihydropyridines (C) which are, in turn, obtained from the corresponding dihydroxypiperidines (B) by dehydration. Suitable dehydration agents are, for example, but not limited to, sulfuric acid, toluenesulfonic acid and trifluoroacetic anhydride. Typically, the dihydroxypiperidines (B) are obtained from the corresponding dihydroxytetrahydropyrans (A) by treatment with aqueous or gaseous ammonia. To provide the desired dihydroxytetrahydropyran (A), the appropriate aldehyde is reacted with an appropriate 3-ketoester and a catalytic amount of a base such as piperidine or KF in a suitable reaction medium. This reaction provides the dihydroxytetrahydropyran from which is obtained by reaction with $NH_3$ or $NH_4OH$ the dihydroxypiperidine which, in turn, provides the dihydropyridine (C) by dehydration. Isolation of the dihydroxytetrahydropyran and dihydroxypiperidine intermediates is unnecessary in this reaction scheme, although the intermediate may be isolated as in some of the following Examples. Oxidation of the dihydropyridine (C), as mentioned above, provides the symmetrical pyridines (D) of this invention. Reaction Scheme 1 further illustrates the reaction scheme.

When providing the dihydropyridine compounds wherein the 4-position is substituted by either an aryl, arylmethyl, phenylmethoxymethyl or heterocyclic radicals wherein the hetero atom is oxygen or sulfur, it is preferred to utilize a catalytic amount of an organic acid as the dehydration agent in place of the usual inorganic acid. Typically, toluenesulfonic acid in a reaction medium of, for example, toluene, has been found to be suitable for this purpose. The reaction is generally run at reflux temperature and water is removed by azeotropic distillation. To provide a major amount of the 3,4-dihydropyridine isomers from the corresponding piperidine, trifluoroacetic anhydride is the preferred dehydration agent. In said process, the reaction medium is typically a chlorinated hydrocarbon such as methylene chloride.

SCHEME I

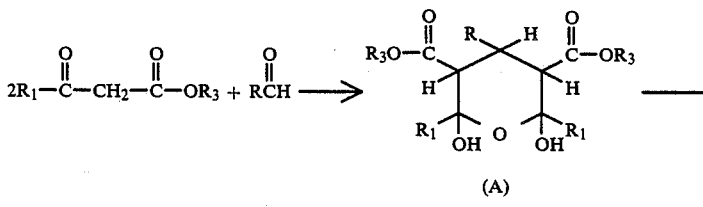

(A)

-continued
SCHEME I

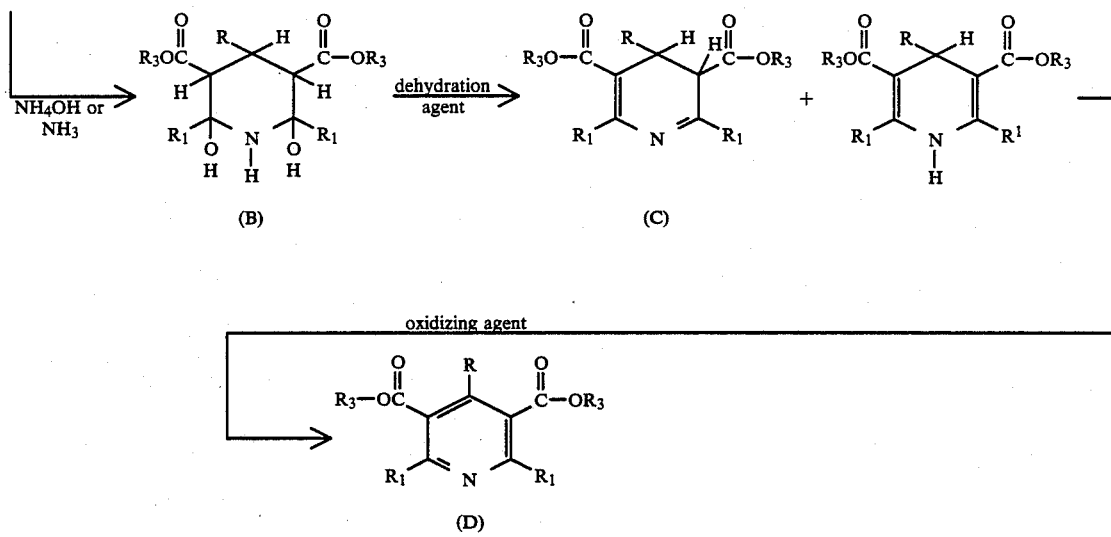

The above Scheme I conveniently provides symmetrical diesters of 2,6-bis substituted-3,5-pyridine-dicarboxylic acids represented by the Formula (D).

Diester compounds of Formula I which are represented by the following formula:

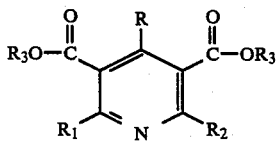

wherein R, $R_1$, $R_2$ and $R_3$ are each defined as above, with the exception that $R_1$ and $R_2$ cannot both be $CF_3$ and wherein each $R_3$ is equal and cannot be hydrogen, can be prepared by a novel dehydrofluorination reaction reacting an equimolar mixture of the corresponding dihydropyridine wherein one of $R_1$ and $R_2$ has one more fluorine than product and a nonaqueous organic base such as 1,8-diazabicyclo-[5.4.0]-undec-5-ene (DBU) or 2,6-lutidine, trialkylamines, and pyridine or mono-, di-, and tri-alkylsubstituted pyridine in the presence of catalytical amounts of DBU either neat or in a suitable solvent such as tetrahydrofuran, or aromatic solvent such as toluene.

Similarly, diester compounds of Formula II in which one of $R_1$ and $R_2$ has two fewer fluorines than the other (i.e., one of $R_1$ and $R_2$ is $CF_3$ and the other is $CFH_2$) are prepared by the further reduction of the compound thus prepared as follows: The compound of Formula II in which one of $R_1$ and $R_2$ is $CF_3$ and the other is $CF_2H$ is reduced to the corresponding 1,2-dihydropyridine using as a strong reducing agent an alkali metal borohydride such as sodium borohydride in any suitable solvent, preferably N,N-dimethylformamide. The dihydropyridine so obtained is then once again dehydrofluorinated using a nonaqueous organic base such as DBU or 2,6-lutidine in an appropriate solvent such as diethyl ether or tetrahydrofuran to the corresponding pyridine compound in which one of $R_1$ and $R_2$ is $CF_3$ and the other is $CFH_2$. If desired, this sodium borohydride reduction/dehydrofluorination sequence may be repeated to form a pyridine compound in which one of $R_1$ and $R_2$ is $CF_3$ and the other is $CH_3$, again proceeding by way of a 1,2-dihydropyridine intermediate.

These novel and unexpected reactions are used herein to provide unexpectedly effective herbicides of this invention.

The mono-acid compounds represented by the following Formula III

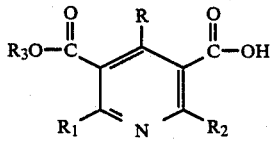

(wherein R, $R_1$, $R_2$ and $R_3$ are each as defined in Formula I above) can be derived from compounds of Formula (D) or II by partial (or selective) hydrolysis. It has been discovered that when $R_2$ in Formula III is a difluoromethyl radical ($-CHF_2$) and $R_1$ is not a difluoromethyl radical, the ester group adjacent the difluoromethyl radical is selectively removed by the hydrolysis procedure, leaving the ester group adjacent $R_1$ intact.

To prepare a compound of Formula I wherein the 3,5-ester groups are dissimilar, there is first prepared a compound represented by the following Formula IV:

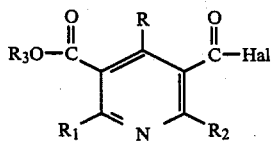

wherein R, $R_1$, $R_2$ and $R_3$ have the same meaning as in Formula I above and Hal means halogen selected from chlorine, bromine, and fluorine.

Compounds of Formula IV above can be prepared by mixing a compound of Formula III above with excess thionyl halide or other suitable agent and holding the mixture at reflux for several hours. Compounds of Formula IV are refluxed with an appropriate alcohol for several hours. The desired product is recovered by known methods to give the desired compound of Formula I above wherein X and Y are dissimilar esters.

Alternatively, a mixture of a compound of Formula III and an excess of an appropriate alkyl halide is stirred in a suitable solvent such as N,N-dimethylformamide (DMF) or acetone with 4 equivalents of potassium fluoride or one equivalent of potassium carbonate as the base. After constant stirring for about 16 hours, the residue is poured into water and extracted with solvent. The solvent extract is dried and concentrated to give the unsymmetrical dicarboxylic acid diester.

To provide the pyridinedicarboxylic acid of the Formula V

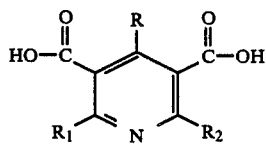

wherein R, $R_1$ and $R_2$ have the same meaning as in Formula I above, an appropriate pyridinedicarboxylic acid diester is mixed with an excess of appropriate base and a suitable solvent. This mixture is held at reflux for several hours and concentrated. After concentration, the desired product is recovered and purified by known methods to provide the desired pyridinedicarboxylic acid. The symmetrical dicarboxylic acid can also be obtained by the hydrolysis of the corresponding ester in the manner described above. Usually recrystallization from an appropriate solvent adequately purifies the product.

Compounds of this invention represented by the following Formula VI:

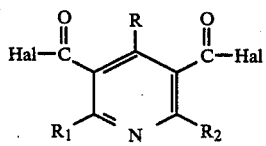

(wherein R, $R_1$ and $R_2$ are defined above) can be prepared by reacting a compound of Formula V with an excess of thionyl or phosphorus halide at reflux conditions for several hours. The product is concentrated and dried.

The symmetrical diester compound of Formula I can also be provided by the reaction of a compound of Formula VI with the appropriate alcohol at reflux conditions for a period of time such as from 15–20 hours. Alternatively, a mixture of one equivalent of a compound of Formula VI, an excess of an appropriate alkyl halide and two equivalents of potassium carbonate is stirred in suitable solvent such as N,N-dimethylformamide for several hours and then poured into water. The desired product is recovered by known methods of solvent extraction and purification.

As can be seen from the above, the appropriate ester is prepared from the corresponding carbonyl chloride by admixture with the appropriate alcohol to provide the desired ester. This can be performed for both the symmetrical and unsymmetrical compounds of the above-described formula.

Compounds of this invention represented by Formula VII:

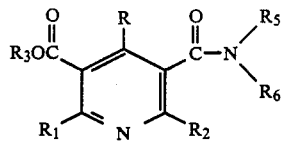

(wherein R, $R_1$, $R_2$, $R_3$, $R_5$ and $R_6$ are as defined above in Formula I) are prepared by reacting a compound of Formula IV with an appropriate amount of amine or ammonia. The procedure is demonstrated in Examples 88 and 89 below.

Compounds of this invention represented by formula VIII:

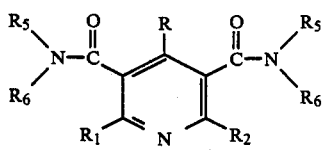

(wherein R, $R_1$, $R_2$, $R_3$, $R_5$ and $R_6$ are defined above in Formula I) are prepared by reacting an excess of the appropriate amine or ammonia with a compound of Formula VI. The procedure is similar to that of Examples 88 and 89 below.

Compounds of this invention represented by formula IX:

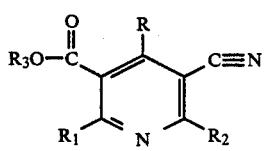

(wherein R, $R_1$, $R_2$, and $R_3$ are as defined in Formula I above) can be prepared by reacting a compound of Formula VII, wherein $R_5$ and $R_6$ are both hydrogen, with an excess of dehydration agent such as phosphorus oxychloride at reflux. The procedure is demonstrated in of Examples 92 and 93 below.

Compounds of this invention represented by formula X:

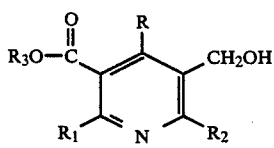

(wherein R, $R_1$, $R_2$, and $R_3$ are as defined in Formula I above) are prepared by reacting a compound of Formula III with an excess of reducing agent such as borane in a suitable solvent. The procedure is demonstrated in Example 96 below.

Compounds of this invention represented by formula XI:

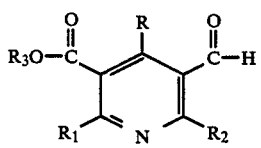

(wherein R, R₁, R₂, and R₃, are as defined above in Formula I) can be prepared by reacting a compound of Formula X with a suitable oxidant such as pyridinium chlorochromate in a suitable solvent such as methylene chloride. The procedure is demonstrated in Example 97 below.

Compounds of this invention represented by the formula XII:

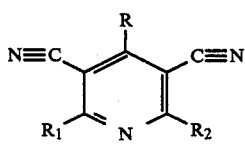

(wherein R, R₁ and R₂, are as defined in Formula I above) are prepared by reacting a compound of Formula VIII, wherein R₅ and R₆ are hydrogen, with excess phosphorus oxychloride at reflux. The procedure is similar to that of Example 92.

Compounds of this invention represented by formula XIII:

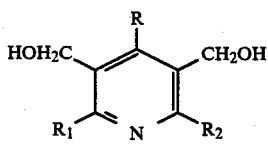

(wherein R, R₁ and R₂, are as defined in Formula I above) can be prepared by reacting a compound of Formula V with excess borane in a procedure similar to that described in Example 96 below.

Compounds of this invention represented by the formula XIV

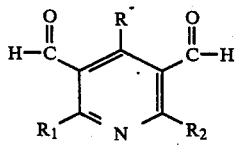

(wherein R, R₁, R₂, and R₃ are as defined in Formula I above) are prepared by reacting a compound of Formula XIII with two equivalents of a suitable oxidant such as pyridinium chlorochromate in a procedure similar to that described in Example 97 below.

Thioester compounds of this invention having the following Formula XV:

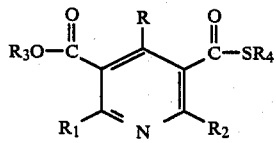

are prepared by reacting an appropriate thiol with a compound of the Formula IV above in the same manner as the preparation of an ordinary ester.

Similarly, dithioesters represented by the following Formula XVI:

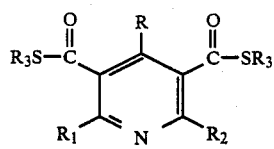

are prepared by reaction of a compound of the Formula VI above with an appropriate thiol. In general, preparation of the various thioester types parallels preparation of the esters described above. Thioesters are exemplified in Examples 140-149.

Imidate compounds of this invention represented by the Formula XVII:

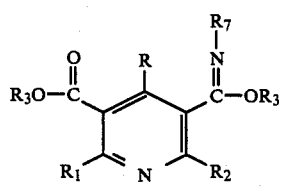

are prepared from the corresponding amide of Formula 8 via the reaction of the amide with thionyl chloride to form a chloroimide, followed by reaction of the chloroimide with an alcohol. This procedure is exemplified in Example 152.

Preparation of the compounds of this invention will become more clear upon examination of the following examples in which, for the most part, the preparation of the dihydroxytetrahydropyran (A), the dihydroxypiperidine (B), and the dihydropyridine (C) precursors is exemplified in detail in a stepwise manner, isolating each precursor before beginning the synthesis of the next. However, a particularly preferred synthesis of the dihydropyridine, precursor compounds is achieved according to Example jj below (the "one pot synthesis") without isolation of the dihydroxytetrahydropyran and dihydroxypiperidine precursors. According to this preferred method to provide the desired dihydropyridines, there is provided a first reaction wherein a mixture of two equivalents of an appropriate 3-ketoester, one equivalent of an appropriate aldehyde and a catalytic amount of piperidine is allowed to react at 40°-100° C. neat or in a suitable solvent (such as methylene chloride or toluene) for a period of 4-20 hours. After the reaction is completed as indicated by ¹⁹F NMR analysis, suitable solvent is added to the product and gaseous ammonia is passed through the mixture until the second reaction is completed. The reaction mixture is then purged with nitrogen to remove excess ammonia. The reaction mixture is then cooled with an ice-water bath to 5°-10° before treatment with concentrated sulfuric acid. After the reaction mixture is stirred for a period of 10 minutes to 2 hours, the mixture is poured onto crushed ice, the methylene chloride layer is separated, dried and concentrated to provide the desired dihydropyridines. In this mode of operation, the desired dihydropyridines is produced in one reaction vessel without isolation of the precursor, dihydroxytetrahydropyran and dihydroxypiperidine. The desired dihydropyridine is therefore obtained in better yield.

To provide the dihydroxytetrahydropyran, precursor of Structure A, the procedure of Day et al as described in the *Journal of Organic Chemistry*, Vol. 30, page 3237 (1965) may be employed. According to this procedure, an appropriate aldehyde is reacted with an appropriate 3-ketoester and a catalytic amount of piperidine with or without a suitable reaction medium.

Preparation of Dihydroxytetrahydropyrans

The following examples a–m provide typical procedures for preparation of precursor compounds of structure (A) shown in Scheme I above.

EXAMPLE a

Preparation of diethyl 2,6-bis(trifluoromethyl)-2,6-dihydroxy-4-propyl-tetrahydro-3,5-pyrandicarboxylate A 500 ml single necked flask is charged with 20 g (0.278 mole) of butyraldehyde, 102 g (0.555 mole) of ethyl trifluoroacetoacetate and approximately 150 ml of ethanol. To this is added 3 g (0.0156 mole) of potassium fluoride. The mixture is stirred at room temperature for 18 hours. The material is concentrated and diluted with ethyl ether. The organics are washed with water, dried and concentrated to give a white powder. The crude product is recrystallized from hot methyl cyclohexane to give 13 g (10.7%) of product, m.p. 128°–132° C.

Anal. Calc'd for $C_{16}H_{22}O_7F_6$: C, 43.63; H, 5.00; Found: C, 43.58; H, 5.04.

EXAMPLE b

Preparation of dimethyl 2,6-bis(trifluoromethyl)-2,6-dihydroxy-4-isobutyl-tetrahydro-3,5-pyrandicarboxylate To a mechanically stirred mixture of 280 g (2.0 mole) of 80% pure methyl trifluoroacetoacetate and 86 g (1.0 mole) of isovaleraldehyde is added 1 ml of piperidine. An exothermic reaction occurs and the temperature of the reaction mixture reaches 105° C. After 5 hours of stirring, the reaction mixture is triturated with 450 ml of hexane and 30 ml of ether and cooled with a dry ice bath to give 1.68 g of a first crop, m.p. 83°–87° C. and 14.51 g of a second crop, m.p. 67°–73° C.

The first crop is the desired product which contains a mixture of 5:1 cis and trans isomers.

Anal. Calc'd for $C_{15}H_{20}F_6O_7$: C, 42.26; H, 4.73; Found: C, 42.54; H, 4.77.

The second crop is a 2:1 mixture of cis and trans isomers. The mother liquor is concentrated to give 344 g of a residue which is a crude mixture of cis and trans isomer of the desired product.

The cis isomer has a structure A1 with the two ester groups cis to each other whereas the trans isomer has a structure A2 with the two ester groups trans to each other as shown below:

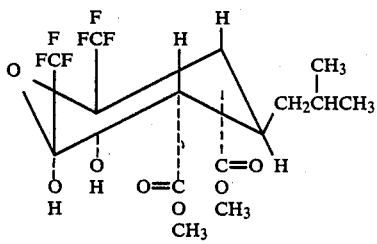

A1

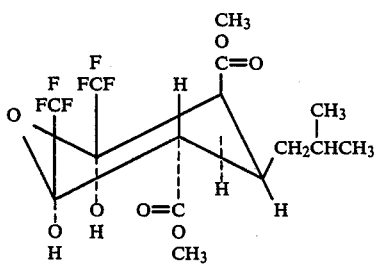

A2

Additional compounds are prepared according to the procedure described in Example a and listed in Table 1 by reacting the appropriate aldehyde with the appropriate trifluoroacetoacetate.

TABLE 1
PREPARATION OF DIHYDROXYTETRAHYDROPYRANS

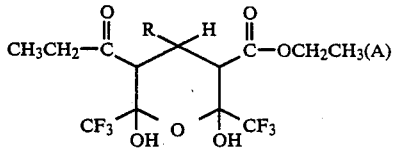

| Example | R | mp °C. | C Calc'd | C Found | H Calc'd | H Found |
|---|---|---|---|---|---|---|
| c | —CH$_2$CH$_3$ | 123–127 | 42.25 | 42.41 | 4.69 | 4.72 |
| d | —CH$_2$CH$_2$CH$_2$CH$_3$ | 45–61 | 44.93 | 45.16 | 5.28 | 5.27 |
| e | —CH(CH$_3$)$_2$ | 88–98 | 43.63 | 43.72 | 5.00 | 5.05 |
| f | —CH$_2$CH(CH$_3$)$_2$ | 87–90 | 44.95 | 45.02 | 5.28 | 5.20 |
| g | —CH(CH$_2$CH$_3$)$_2$ | 105–111 | 46.15 | 46.23 | 5.55 | 5.66 |
| h | cyclopropyl | 98–101 | 43.84 | 43.96 | 4.60 | 4.52 |
| i | cyclohexyl | 100–103 | 47.60 | 47.38 | 5.26 | 5.63 |

TABLE 1-continued
PREPARATION OF DIHYDROXYTETRAHYDROPYRANS

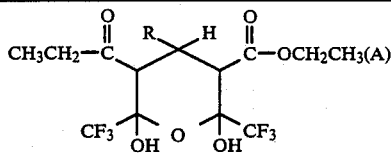

| Example | R | mp °C. | C Calc'd | C Found | H Calc'd | H Found |
|---|---|---|---|---|---|---|
| j | —CH₂—C₆H₅ | 120–125 | 49.07 | 49.79 | 4.70 | 4.42 |
| k | —CH₂OCH₂—C₆H₅ | 90–93 | 49.03 | 49.45 | 4.71 | 4.71 |
| l | —CH₂OCH₃ | 77.5–81 | 40.73 | 40.69 | 4.56 | 4.71 |
| m | —C₆H₅ | 128–136 | 48.11 | 47.68 | 4.25 | 4.07 |

Preparation of Dihydroxypiperidines

To provide the dihydroxypiperidine precursor (B), four different methods may be employed. The first method (Method I) employs the procedure wherein a mixture of two equivalents of a 3-ketoester, one equivalent of an appropriate aldehyde and 1.5 equivalents of ammonium hydroxide is refluxed in ethanol for 4–18 hours and concentrated to provide B similar to the literature procedure.

In the second method (Method II), (Journal of Heterocyclic Chemistry, Vol. 17, 1109 (1980)), a mixture of one equivalent of dihydroxytetrahydropyran of structure A, 1.5 equivalents of aqueous ammonium hydroxide and a suitable amount of ethanol is stirred at room temperature or held at reflux for 4–18 hours and concentrated. The residue is recrystallized from the appropriate solvent or purified in another suitable manner to provide (B).

In the third method (Method III), a stream of gaseous ammonia is passed through a solution of dihydroxytetrahydropyran of structure (A) in a suitable solvent (such as tetrahydrofuran, toluene, or methylene chloride) for several hours until the $^{19}$F NMR analysis indicates a complete reaction. The reaction mixture is concentrated and the residue is recrystallized from an appropriate solvent otherwise purified as appropriate to provide the precursor of structure (B).

In the fourth method (Method IV), a mixture of two equivalents of an appropriate 3-ketoester, one equivalent of an appropriate aldehyde and a catalytic amount of piperidine is stirred with or without an appropriate solvent at 40°–100° for a period of from several hours to several days until the $^{19}$F NMR analysis indicates a complete reaction. After completion of the above first step of Method IV, an appropriate solvent is added to the above reaction mixture if the first step reaction is carried out without a solvent. A stream of anhydrous ammonia gas is passed through the solution at 40°–70° C. until the $^{19}$F NMR indicates a complete reaction (usually in the period of about six to ten hours). The reaction mixture is concentrated and the residue is recrystallized from an appropriate solvent to provide the precursor structure (B).

Method IV is the preferred method because it provides higher yield of the desired product.

To further illustrate Methods I–IV, the following examples n–ff are provided.

EXAMPLE n

Preparation of dimethyl 2,6-bis(trifluoromethyl)-2,6-dihydroxy-4-isobutyl-3,5-piperidinedicarboxylate To a solution of 344 g (0.920 mole) crude product from Example b in 500 ml of tetrahydrofuran (THF) is passed 58 g (3.41 mole) of gaseous ammonia for 3 hours. The reaction mixture is concentrated and the residue (332 g) is recrystallized from hexane-ether to give 53.7 g (13% yield from methyl trifluoroacetoacetate) of the desired product as a white solid, m.p. 102°–106° C.

Anal. Calc'd for $C_{15}H_{21}F_6N_1O_6$: C, 42.36; H, 5.00; N, 3.29; Found: C, 42.84; H, 4.94; N, 3.29.

The mother liquor is concentrated to provide more of the crude desired product.

EXAMPLE o

Preparation of diethyl 2,6-bis(trifluoromethyl)-2,6-dihydroxy-4-(2-furyl)-3,5-piperidinedicarboxylate A 500 mL 3 necked flask is charged with 60 mL ethanol, 29.07 g (0.3 mole) of 2-furaldehyde and 110 g (0.6 mole) of ethyl trifluoroacetoacetate. The reaction mixture is cooled in an ice bath before 21.15 21.15 g (0.35 mole) of aqueous ammonium hydroxide is added slowly with stirring. The mixture is heated at reflux for 2 hours and cooled. The resulting precipitate is filtered and recrystallized from hot ethanol to give 53.34 g (39%) of crystals, m.p. 129°–131° C.

Anal. Calc'd C$_{17}$H$_{17}$F$_6$N$_1$O$_7$: C, 44.06; H, 4.10; N, 3.02; Found: C, 44.04; H, 4.12; N, 3.03.

EXAMPLE p

Preparation of diethyl 2,6-bis(trifluoromethyl)-2,6-dihydroxy-4-propyl-3,5-piperidinedicarboxylate A 500 ml round bottomed flask was charged with 150–200 mL of ethanol and 40 g (0.0909 mole) of product of Example a. The mixture is stirred by a magnetic stirrer while 8.23 g (0.136 mole) of 58% aqueous ammonium hydroxide is added slowly to the flask. The mixture is stirred for 18 hours under nitrogen. The precipitate is filtered to yield 17.83 g (44.68%) of the desired product, m.p. 140°–142° C.

Anal. Calc'd for C$_{16}$H$_{23}$O$_6$N$_1$F$_7$: C, 43.73; H, 5.23; N, 3.18; Found: C, 43.67; H, 5.26; N, 3.19.

EXAMPLE q

Preparation of trans-diethyl2,6-bis(difluoromethyl)-2,6-dihydroxy-4-isobutyl-3,5-piperidinedicarboxylate To a mixture of 25.0 g (0.150 mole) of ethyl difluoroacetotoacetate (EDFAA) and 8.04 ml (0.075 mole) of isovaleradehyde is added to 2 ml of piperidine. The reaction mixture becomes exothermic and temperature of the mixture reaches 86°. After the temperature of the reaction mixture has subsided to room temperature, the reaction mixture is treated with THF (100 ml). Gaseous NH$_3$ is passed through the above THF solution until $^{19}$F NMR indicates a complete reaction. The reaction mixture is concentrated to 32.77 g (100%) of an oil which contains the desired product and its cis isomer. This oil is crystallized from hexane to give a solid. Part of this solid (5.0 g) is dissolved in ether. The ether solution is washed with water, dried (MgSO$_4$) and concentrated to an oil which crystallized upon standing. Recrystallization from hexane gives 1.0 g (22.8%) of this desired product as a white solid, m.p. 98°–100° C. This material is identified as the trans isomer by $^{19}$F NMR.

Anal. Calc'd for C$_{17}$H$_{27}$F$_4$NO$_6$: C, 48.92; H, 6.52; N, 3.36; Found: C, 48.93; H, 6.51; N, 3.31.

EXAMPLE r

Preparation of diethyl 2,6-bis(trifluoromethyl)-2,6-dihydroxy-4-butyl-3,5-piperidinedicarboxylate To a 500 mL 3-necked flask is charged 40 g (0.0881 mole) of the product of Example d in Table 1 and about 200–250 mL of THF. The flask is fitted with 2 dry ice condensers and a nitrogen inlet. Ammonia gas, 5 g (0.294 mole) is bubbled into the solution and the solution is stirred for 18 hours. The organics are concentrated, diluted with ethyl ether, washed in water, dried over anhydrous MgSO$_4$ and concentrated. The residue is triturated with n-hexane and filtered to give 7.57 g (19%) of the desired product, m.p. 77°–80° C.

Anal. Calc'd for C$_{17}$H$_{25}$F$_6$N$_1$O$_6$: C, 45.03; H, 5.51; N, 3.09; Found: C, 44.96; H, 5.58; N, 3.03.

Additional examples of 2,6-dihydroxypiperidines of structure B above are prepared according to the above-described method of Examples n to r and are listed in Table 2.

TABLE 2

PREPARATION OF DIHYDROXYPIPERIDINES

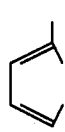

| | | | | C | | H | | N | |
|---|---|---|---|---|---|---|---|---|---|
| Example | R | mp °C. | n$^{25}$ | Calc'd | Found | Calc'd | Found | Calc'd | Found |
| s | —CH$_3$ | 133–135 | | 41.07 | 41.28 | 4.15 | 4.25 | 3.42 | 3.35 |
| t | —CH$_2$CH$_3$ | 129–131 | | 42.35 | 42.40 | 4.94 | 5.00 | 3.29 | 3.33 |
| u | —CH(CH$_3$)$_2$ | 85–89 | | 43.74 | 44.08 | 5.28 | 5.13 | 3.19 | 2.74 |
| v | —CH$_2$CH(CH$_3$)$_2$ | 69–73 | | 45.03 | 45.20 | 5.51 | 5.50 | 3.09 | 3.11 |
| w | 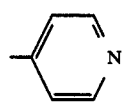 | 103–105 | | 42.58 | 43.08 | 3.96 | 4.06 | 2.92 | 2.78 |
| x | 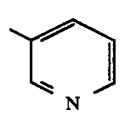 | 179° | | 45.58 | 45.51 | 4.25 | 4.03 | 5.91 | 5.52 |
| y |  | 133–135 | | 45.58 | 45.59 | 4.25 | 4.28 | 5.91 | 5.90 |
| z | —CH(CH$_2$CH$_3$)$_2$ | 86–89 | | 46.25 | 46.67 | 5.82 | 5.79 | 3.00 | 3.17 |

TABLE 2-continued
PREPARATION OF DIHYDROXYPIPERIDINES

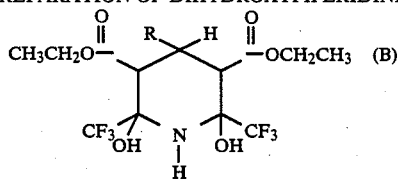 (B)

| Example | R | mp °C. | $n^{25}$ | C Calc'd | C Found | H Calc'd | H Found | N Calc'd | N Found |
|---|---|---|---|---|---|---|---|---|---|
| aa | —CH₂—(phenyl) | 134–141 | | 49.28 | 50.38 | 4.72 | 4.67 | 2.87 | 2.78 |
| bb | (cyclohexenyl) | 99–101 | | 48.21 | 47.96 | 4.27 | 4.25 | 2.96 | 2.79 |
| cc | —CH₂CH₂SCH₃ | 55–73 | | 40.76 | 40.81 | 4.92 | 4.86 | 2.97 | 3.10 |
| dd | —CH₂OCH₃ | 122–123 | | 40.82 | 40.87 | 4.80 | 4.70 | 3.17 | 3.40 |
| ee | —CH₂CH₂OCH₂CH₃ | | 1.4269 | 43.50 | 43.82 | 5.37 | 5.30 | 2.98 | 3.14 |
| ff | —CH₂OCH₂—(phenyl) | 102–109 | | 48.75 | 48.74 | 4.87 | 4.87 | 2.71 | 2.71 |

Preparation of Dihydropyridines

The dihydropyridine precursors of structure (C) are obtained by dehydration of the corresponding dihydroxypiperidines with dehydration agents such as concentrated sulfuric acid (Method V) or trifluoroacetic anhydride (Method VI) or by azeotropic removal of water using p-toluenesulfonic acid as catalyst (Method VII).

To further illustrate the above-described Methods V–VII, the following examples gg-fff are provided.

EXAMPLE gg

Preparation of a 2:1 mixture of dimethyl 2,6-bis(trifluoromethyl)-1,4-dihydro-4-isobutyl-3,5-pyridine-dicarboxylate and its 3,4-dihydropyridine isomer To an ice water cooled mixture of 200 ml of concentrated sulfuric acid and 200 ml of methylene chloride is added 48.7 g (0.115 mole) of the product of Example n at once. The reaction mixture is stirred for 20 minutes and poured into 1 L. of ice water. The methylene chloride layer is separated and washed once with 100 ml of saturated sodium bicarbonate, dried and concentrated to give 28.0 g (64.6%) of crude product. A portion (5.0 g) of this product is kugelrohr distilled at 0.5 torr (pot temperature at 120° C.) to give 4.8 g of the desired product, $n_D^{25}$ 1.4391.

Anal. Calc'd for $C_{15}H_{17}F_6N_1O_4$: C, 46.28; H, 4.40; N, 3.60; Found: C, 46.39; H, 4.44; N, 3.60.

EXAMPLE hh

Preparation of diethyl 2,6-bis(difluoromethyl-1,4-dihydro-4-isobutyl-3,5-pyridinedicarboxylate A 5.0 g (0.012 mole) crude cis and trans mixture of the product of Example q is stirred with 10 ml of trifluoroacetic anhydride. The temperature of the reaction mixture rises to 36° C. After the temperature subsides to room temperature, the reaction mixture is concentrated. The residue is dissolved in ether and washed with saturated NaHCO₃, dried (MgSO₄) and concentrated to an oil (3.76 g, 82.3%) which is chromatographed by HPLC using 10% ethyl acetate/cyclohexane as eluent to give 1.73 g (37.8%) of the desired product as an oil, $n_D^{25}$ 1.4716.

Anal. Calc'd for $C_{17}H_{23}F_4NO_4$: C, 53.54; H, 6.08; N, 3.67; Found: C, 53.38; H, 6.40; N, 3.25.

EXAMPLE ii

Preparation of diethyl 2,6-bis(trifluoromethyl)-1,4-dihydro-4-(2-thienyl)-3,5-pyridinedicarboxylate Approximately 100 ml of toluene is refluxed using a Dean-Stark trap to remove water. To the cooled toluene is added 20 g (0.0418 mole) of the product of Example w in Table 2 and 2.0 g (0.0105 mole) of p-toluenesulfonic acid. The mixture is heated to reflux and refluxed for 5½ hours. The solution is cooled and filtered. The solvent is stripped off and the product is chromatographed using 20% ethyl acetate/cyclohexane as eluent. Wt. of product—2.45 g (13.3%), $n_D^{25}$ 1.4937.

Anal. Calc'd for $C_{17}H_{15}O_4N_1F_6S_1$: C, 46.04; H, 3.38; N, 3.16; S, 7.22; Found: C, 46.11; H, 3.44; N, 3.12; S, 7.16.

In the preferred method to provide the desired dihydropyridines, there is provided a first reaction wherein a mixture of two equivalents of an appropriate 3-ketoester, one equivalent of an appropriate aldehyde and a catalytic amount of piperidine is allowed to react at 40°–100° C. with or without a suitable solvent (such as methylene chloride) for a period of 4–20 hours. After the reaction is completed as indicated by $^{19}F$ NMR analysis, methylene chloride is added to the product and gaseous ammonia is passed through the mixture until the second reaction is completed. The reaction mixture is then purged with nitrogen to remove excess ammonia. The reaction mixture is then cooled with an ice-water bath to 5°-10° C. before treatment with concentrated sulfuric acid. After the reaction mixture is stirred for a period of 10 minutes to 2 hours, the mixture is poured onto crushed ice, the methylene chloride layer is separated, dried and concentrated to provide the desired dihydropyridines. In this mode of operation, the desired dihydropyridine is produced in one reaction vessel without isolation of the intermediates dihydroxytetrahydropyran and dihydroxypiperidine. The desired dihydropyridine is therefore obtained in better yield. To illustrate the above-described procedure, the following examples are provided.

EXAMPLE jj

One pot synthesis of a mixture of diethyl 2,6-bis(trifluoromethyl)-1,4-dihydro-4-ethyl-3,5-pyridinedicarboxylate and its 3,4-dihydropyridine isomer A mixture of 368 g (2.0 mole) of ethyl trifluoroacetoacetate, 58 g (1.0 mole) of propionaldehyde and 1 ml of piperidine in 400 ml of methylene chloride is stirred for 1 hr at 20° C. and then for 1 h at 30° C. and refluxed for 1 hr and cooled. An additional 16.8 g (0.289 mole) of propionaldehyde is added to the above mixture and then refluxing is continued for 2 hrs. The heating mantle is removed. Through the reaction mixture is passed 108 g (6.35 mole) of ammonia gas in 2 hours. The reaction mixture is stirred for 40 hours at 20° C. then cooled in ice water. To the reaction mixture is added carefully 100 ml of concentrated sulfuric acid in 20 minutes followed by an additional 300 ml of concentrated sulfuric acid in 10 minutes. The reaction mixture is poured onto 600 g of crushed ice in a 4 L. beaker. The methylene chloride layer is separated, dried (MgSO$_4$) and concentrated to give 386 g of an oil which contains a mixture of the desired product and its 3,4-dihydro isomer. This oil is added to a vigorously stirred mixture of 300 ml of concentrated sulfuric acid and 300 ml of methylene chloride. The mixture is stirred for 30 min. and poured onto 1 kg of ice. The methylene chloride layer is separated, dried (MgSO$_4$) and concentrated to give 348 g of an oil which is triturated with 400 ml of petroleum ether to remove 9.5 g of an insoluble solid. The petroleum ether filtrate is then concentrated. The residue is kugelrohr distilled at 0.4 torr to give 290 g (74.5%) of an oil which is more than 90% pure of a mixture of the desired product containing 1,4-dihydro (84%) and its 3,4-dihydro (16%) isomers determined by a $^{19}$F nmr analysis.

Additional examples of dihydropyridines of structure (C) in Scheme I are prepared according to the above-described methods in Examples gg to jj and are listed in Table 3. In all of the Examples in Table 3, R$_3$ is ethyl.

TABLE 3
PREPARATION OF DIHYDROPYRIDINES

| Example | R | R$_1$ | 1,4 | 3,4 | $n_D^{25}$ | C Calc'd | C Found | H Calc'd | H Found | N Calc'd | N Found |
|---|---|---|---|---|---|---|---|---|---|---|---|
| kk | —CH$_3$ | CF$_3$ | 100 | | 1.4377 | 44.81 | 44.98 | 4.03 | 4.06 | 3.73 | 3.61 |
| ll | —CH$_2$CH$_3$ | CF$_3$ | 100 | | 1.4441 | 46.27 | 46.41 | 4.37 | 4.19 | 3.59 | 3.62 |
| mm | —CH$_2$CH$_2$CH$_3$ | CF$_3$ | 100 | | 1.4427 | 47.88 | 47.92 | 4.23 | 4.28 | 3.49 | 3.47 |
| nn | —CH(CH$_3$)$_2$ | CF$_3$ | 100 | | 1.4440 | 47.64 | 47.69 | 4.71 | 4.75 | 3.47 | 3.46 |
| oo | —CH$_2$CH$_2$CH$_2$CH$_3$ | CF$_3$ | 100 | | 1.4414 | 48.95 | 48.95 | 5.03 | 5.09 | 3.35 | 3.35 |
| pp | CH$_2$CH(CH$_3$)$_2$ | CF$_3$ | 100 | | 1.4420 | 48.92 | 48.78 | 5.03 | 5.06 | 3.35 | 3.31 |
| qq | CH$_2$—C$_6$H$_5$ | CF$_3$ | 100 | | 1.4820 | 52.98 | 53.24 | 4.63 | 4.27 | 3.09 | 3.09 |
| rr | (furyl) | CF$_3$ | 100 | | 1.4720 | 47.77 | 47.83 | 3.51 | 3.51 | 3.27 | 3.25 |
| ss | (pyridyl) | CF$_3$ | 100 | | (a) | 49.31 | 49.33 | 3.65 | 3.72 | 6.39 | 6.39 |
| tt | (pyridyl) | CF$_3$ | 100 | | (b) | 49.31 | 49.32 | 3.65 | 3.68 | 6.39 | 6.35 |

TABLE 3-continued
PREPARATION OF DIHYDROPYRIDINES

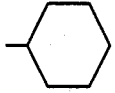 (C)

| Example | R | R₁ | 1,4 | 3,4 | $n_D^{25}$ | C Calc'd | C Found | H Calc'd | H Found | N Calc'd | N Found |
|---|---|---|---|---|---|---|---|---|---|---|---|
| uu | 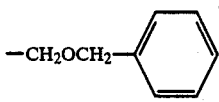 | CF₃ |  | 100 | 1.4586 | 51.46 | 50.15 | 5.23 | 5.38 | 3.16 | 3.24 |
| vv | —CH₂OCH₂—  | CF₃ | 100 |  | 1.4845 | 52.40 | 52.48 | 4.40 | 4.42 | 2.91 | 2.92 |
| ww | —CH₂OCH₃ | CF₃ | 92 | 8 | 1.4436 | 44.45 | 44.26 | 4.23 | 4.40 | 3.46 | 3.22 |
| xx | —CH₂CH₂OCH₂CH₃ | CF₃ | 85 | 15 | 1.4419 | 47.12 | 46.96 | 4.88 | 4.69 | 3.23 | 3.02 |
| yy | —CH₂SCH₃ | CF₃ | 89 | 11 | 1.4486 | 42.76 | 42.72 | 4.07 | 4.24 | 3.32 | 3.07 |
| zz | —CH₂CH₂SCH₃ | CF₃ | 84 | 14 | 1.4688 | 44.14 | 44.12 | 4.40 | 4.19 | 3.22 | 3.05 |
| aaa | —CH(CH₂CH₃)₂ | CF₃ | 100 |  | 1.4433 | 50.11 | 50.15 | 5.37 | 4.99 | 3.25 | 3.22 |
| bbb | —CH₂CH₂CH₃ | CF₂H | 100 |  | 1.4726 | 52.32 | 51.98 | 5.76 | 5.86 | 3.81 | 3.66 |
| ccc | 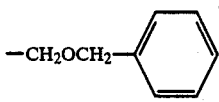 | CF₂H | 100 |  | (c) | 56.02 | 56.16 | 6.18 | 6.42 | 3.44 | 3.42 |
| ddd | 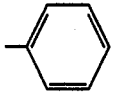 | CF₃ | 100 |  | (d) | 52.18 | 52.33 | 3.92 | 3.95 | 3.20 | 3.16 |
| eee | —CHCH₂CH₃<br>\|<br>CH₃ | CF₃ | 80 | 20 | 1.4417 | 48.92 | 49.05 | 5.07 | 5.10 | 3.36 | 3.34 |
| fff | —CH₂C(CH₃)₃ | CF₃ | 75 | 25 | 1.4393 | 50.12 | 50.19 | 5.37 | 5.37 | 3.25 | 3.20 |

(a) m.p. 171–172° C.
(b) m.p. 136–138° C.
(c) m.p. 40–44° C.
(d) m.p. 42–45° C.

The following examples illustrate, in a nonlimiting manner, the preparation of particular novel herbicides and intermediates for the production of herbicides in accordance with this invention.

To prepare the symmetrical 3,5-pyridinedicarboxylates according to Scheme 1, the corresponding dihydropyridines C are treated with sodium nitrite in acetic acid. The above described procedure is illustrated by Examples 1 to 11.

EXAMPLE 1

Preparation of diethyl 2,6-bis(trifluoromethyl)-4-ethyl-3,5-pyridinedicarboxylates A 250 ml flask is charged with 35 ml of glacial acetic acid and 13.89 g (0.0354 mole) of diethyl 2,6-bis-(trifluoromethyl)-4-ethyl-1,4-dihydro-3,5-pyridinedicarboxylate. Sodium nitrite is added in the amount of 3 g (0.0434 mole) and the mixture is stirred for 72 hours under nitrogen. The solution is poured over ice/water and stirred. The organics are extracted in ether and washed with aqueous saturated sodium bicarbonate solution. Organics are then dried on anhydrous magnesium sulfate, filtered and concentrated to yield 4.93 g (35.67%) of product, m.p. 33°–35° C.

Anal. Calc'd for C₁₅H₁₅O₄N₁F₆: C, 46.51; H, 3.87; N, 3.61; Found: C, 46.54, H, 3.90; N, 3.63.

EXAMPLE 2

Preparation of diethyl 2,6-bis(trifluoromethyl)-4-methyl-3,5-pyridinedicarboxylate A 50 ml round bottomed flask is charged with 20 ml of glacial acetic acid. To this is added 5 g (0.0133 mole) of diethyl 2,6-bis(trifluoromethyl)-4-methyl-1,4-dihydro-3,5-pyridinedicarboxylate, followed by a slow addition of 3 g (0.0434 mole) of sodium nitrite. The flask is immediately fitted with a condenser and nitrogen line, the stirring continued for 18 hours, and the mixture is poured over crushed ice and water. The organics are extracted twice with ether, washed once with saturated aqueous sodium chloride and washed twice with saturated aqueous sodium bicarbonate solution. The organics are dried over anhydrous magnesium sulfate and concentrated yielding 2.16 g (43.5%) of product, m.p. 55°–58° C.

Anal. Calc'd for $C_{14}H_{13}F_6NO_4$: C, 45.05; H, 3.48; N, 3.75; Found: C, 44.95; H, 3.56; N, 3.75.

In a similar manner as described in Examples 1 and 2 above, but substituting the appropriate starting material and reaction conditions, other pyridinedicarboxylates are prepared. The same or equivalent solvents, bases and catalysts, together with the appropriate temperatures and times are readily used in these process embodiments. Typical other compounds prepared in accordance with the above procedure are shown in Table 4 together with certain of their physical properties.

TABLE 4

PREPARATION OF SYMMETRICAL 3,5-PYRIDINEDICARBOXYLATES (D)

| Ex. No. | Starting Material Product of Example | Compound | Empirical Formula | m.p. °C. | $n_D^{25}$ | Analysis Element | Calc'd % | Found % |
|---|---|---|---|---|---|---|---|---|
| 3 | ddd | Diethyl 2,6-bis(trifluoromethyl)-4-phenyl-3,5-pyridinedicarboxylate | $C_{19}H_{15}F_6N_1O_4$ | | 1.4696 | C | 52.42 | 52.47 |
| | | | | | | H | 3.47 | 3.51 |
| | | | | | | N | 3.22 | 3.20 |
| 4 | rr | Diethyl 2,6-bis(trifluoromethyl)-4-(2-furyl)-3,5-pyridinedicarboxylate | $C_{17}H_{13}F_6N_1O_5$ | 45–47 | | C | 48.00 | 47.97 |
| | | | | | | H | 3.05 | 3.08 |
| | | | | | | N | 3.29 | 3.29 |
| 5 | ii | Diethyl 2,6-bis(trifluoromethyl)-4-(2-thienyl)-3,5-pyridinedicarboxylate | $C_{17}H_{13}F_6N_1O_4S_1$ | 48–50 | | C | 46.25 | 46.13 |
| | | | | | | H | 2.94 | 2.94 |
| | | | | | | N | 3.14 | 3.14 |
| | | | | | | S | 7.25 | 7.31 |
| 6 | mm | Diethyl 2,6-bis(trifluoromethyl)-4-propyl-3,5-pyridinedicarboxylate | $C_{16}H_{17}O_4N_1F_6$ | | 1.4315 | C | 47.88 | 48.15 |
| | | | | | | H | 4.23 | 3.85 |
| | | | | | | N | 3.49 | 3.47 |
| 7 | pp | Diethyl 2,6-bis(trifluoromethyl)-4-isobutyl-3,5-pyridinedicarboxylate | $C_{17}H_{19}O_4N_1F_6$ | | 1.4280 | C | 49.15 | 48.93 |
| | | | | | | H | 4.57 | 4.66 |
| | | | | | | N | 3.37 | 3.45 |
| 8 | tt | Diethyl 2,6-bis(trifluoromethyl)-4-(3-pyridyl)-3,5-pyridinedicarboxylate | $C_{18}H_{14}O_4N_2F_6$ | | 1.4710 | C | 49.55 | 49.58 |
| | | | | | | H | 3.23 | 3.26 |
| | | | | | | N | 6.42 | 6.37 |
| 9 | ss | Diethyl 2,6-bis(trifluoromethyl)-4-(4-pyridyl)-3,5-pyridinedicarboxylate | $C_{18}H_{14}O_4N_2F_6$ | | 1.4711 | C | 49.55 | 49.27 |
| | | | | | | H | 3.23 | 3.27 |
| | | | | | | N | 6.42 | 6.47 |
| 10 | ww | Diethyl 2,6-bis(trifluoromethyl)-4-(methoxymethyl)-3,5-pyridinedicarboxylate | $C_{15}H_{15}F_6NO_5$ | | 1.4291 | C | 44.67 | 44.79 |
| | | | | | | H | 3.75 | 3.78 |
| | | | | | | N | 3.47 | 3.44 |
| 11 | bbb | Diethyl 2,6-bis(difluoromethyl)-4-propyl-3,5-pyridinedicarboxylate | $C_{16}H_{19}F_4NO_4$ | 22 | | C | 52.60 | 52.63 |
| | | | | | | H | 5.24 | 5.61 |
| | | | | | | N | 3.43 | 3.65 |

The following examples 12–27 illustrate a novel procedure of preparing compounds of this invention represented by the Formula II.

EXAMPLE 12

Preparation of diethyl 2-(difluoromethyl)-4-ethyl-6-(trifluoromethyl)-3,5-pyridinedicarboxylate A mixture of 1558 g (4.00 moles) of diethyl 2,6-bis(trifluoromethyl)-1,4-dihydro-4-ethyl-3,5-pyridinedicarboxylate, 628 g (4.0 moles) of 1,8-diazabicyclo-[5.4.0]-undec-5-ene (DBU), and 500 ml of tetrahydrofuran is held at reflux for 19 hours, cooled and poured into a mixture of 2 kg of ice and 250 ml of concentrated hydrochloric acid. The organic layer is separated and the aqueous layer extracted with 500 ml of $CH_2Cl_2$ twice. The combined organic materials are dried ($MgSO_4$) and concentrated. The residue is kugelrohr distilled at 1 torr (pot temperature of 150°–160° C.) to give 1158 g (78.5%) of desired product, $n_D^{25}$ 1.4458.

Anal. Calc'd. $C_{15}H_{16}F_5NO_4$: C, 48.78; H, 4.37; N, 3.79; Found: C, 48.75; H, 4.29; N, 3.72.

EXAMPLE 13

Preparation of diethyl 2-(difluoromethyl)-4-n-propyl-6-(trifluoromethyl)-3,5-pyridinedicarboxylate A mixture of 20.0 g (0.05 mole) of diethyl 2,6-bis(trifluoromethyl)-1,4-dihydro-4-n-propyl-3,5-pyridinedicarboxylate, 7.62 g (0.05 mole) of DBU, and 200 ml of THF is held at reflux for 9 hours, cooled and poured into 500 ml of ice water. The mixture is extracted with ether (2×200 ml). The ether extract is washed with diluted hydrochloric acid, dried ($MgSO_4$), and concentrated to give 12.4 g (64.5%) of the desired product, $n_D^{25}$ 1.4436.

Anal. Calc'd. for $C_{16}H_{18}F_5N_1O_4$: C, 50.13; H, 4.73; N, 3.65; Found: C, 49.92; H, 4.71; N, 3.58.

EXAMPLE 14

Preparation of dimethyl 2-(difluoromethyl)-6-(trifluoromethyl)-4-isobutyl-3,5-pyridinedicarboxylate (a) Reaction of the Product of Example gg with DBU A mixture of 23.0 g (0.0591 mole) of the product of Example gg, 12.2 g (0.077 mole) of 96% pure DBU, and 100 ml of THF is held at reflux for 3 days and poured into 250 ml of 3N HCl. The oil precipitate is extracted into ether (2×100 ml). The ether extracts are dried ($MgSO_4$) and concentrated to give 14.4 g of an oil which, according to $^1H$ NMR, contained the desired product and acidic products. This oil is dissolved in ether and extracted with 100 ml of saturated sodium bicarbonate. The ether layer is dried ($MgSO_4$) and concentrated to give 8.9 g of an oil which is 71% pure desired product (by $^{19}F$ NMR).

The sodium bicarbonate extract is acidified with concentrated HCl to give an oil which is extracted into ether. The ether layer is dried (MgSO$_4$) and concentrated to give 4.8 g of a residue which contained monocarboxylic acid and dicarboxylic acid (9:1) derived from the desired product. This residue is treated with 3.0 g (0.0217 mole) of potassium carbonate, 20 ml of methyl iodide, and 50 ml of acetone. The mixture is held at reflux for 42 hours and concentrated. The residue is treated with water and extracted with ether (2×100 ml). The ether layer is dried and concentrated. The residue is kugelrohr distilled at 1 torr (pot temperature of 130° C.) to give 5.1 g (23.4% from Example gg) of the desired product as an oil, n$_D^{25}$ 1.4478. This product crystallizes after standing, m.p. 36°–37° C.

Anal. Calc'd. for C$_{15}$H$_{16}$F$_5$N$_1$O$_4$: C, 48.79; H, 4.37; N, 3.79; Found: C, 48.75; H, 4.39; N, 3.77.

The 71% pure desired product described previously was chromatographed by HPLC using 3% ethyl acetate/cyclohexane as eluent to give an earlier fraction (0.79 g, retention time 7–8.5 min) which was identified as methyl 6-(difluoromethyl)-4-(isobutyl)-2-(trifluoromethyl)-3-pyridinecarboxylate. The second fraction (retention time 8.5–18.5 min) is an additional 6.4 g (29.4%) of pure desired product, n$_D^{25}$ 1.4474.

(b) Reaction of the Product of Example gg with Tributylamine

A mixture of 38.9 g of a 80% pure product of Example gg and 20.5 g of tributylamine is heated to 155° C. in 30 minutes. The reaction mixture was cooled to 30° C. and diluted with 100 ml of toluene. The toluene solution is washed successively with 6N hydrochloric acid, saturated sodium bicarbonate, and brine, dried and concentrated to give 36.4 g of a 73% pure product which corresponds to a 86% yield. This reaction can also be carried out in excess of tributylamine (10 equivalent) giving essentially similar results.

(c) Reaction of the Product of Example gg with Tributylamine in Toluene

A mixture of 38.9 g of a 80% pure product of Example gg, 20.4 g of tributylamine and 30 ml of toluene is heated to 155° C. in 40 minutes and held at 115° C. for 1 hour and 40 minutes. The reaction mixture is cooled and worked up as in (b) to give 36.3 g of a 76% pure product which corresponds to a 90% yield.

(d) Reaction of the Product of Example gg with Triethylamine

A mixture of 11.8 g of a 80% pure product of Example gg and 3.34 g of triethylamine is heated at 100° C. for 10 minutes, then at 125° C. for 10minutes. The reaction mixture was cooled and worked up as in (b) to give 8.14 g of a 76% pure product which corresponds to a 63% yield.

(e) Reaction of the Product of Example gg with 2,6-Lutidine in the Presence of a Catalytic Amount of DBU A mixture of 5.0 g of product of Example gg and 2.13 g of 2,6-lutidine is heated at 143° C. for 30 minutes. Two drops of DBU is added and the reaction mixture is heated for additional 1 hour and 30 minutes, cooled and worked up as in (b) to give 4.23 g of the desired product. The reaction can also be carried out in excess of 2,6-lutidine and catalytic amount of DBU without solvent or in the presence of toluene as solvent giving similar results.

EXAMPLE 15

Preparation of diethyl 2-(difluoromethyl)-4-isopropyl-6-(trifluoromethyl)-3,5-pyridinedicarboxylate A mixture of 50.0 g (0.124 mole) of diethyl 2,6-bis(trifluoromethyl)-1,4-dihydro-4-isopropyl-3,5-pyridinedicarboxylate, 18.87 g (0.124 mole) of DBU and 200 ml of THF is held at reflux for 18 hours and poured into water and extracted with ether. The ether extract is washed with diluted hydrochloric acid, dried (MgSO$_4$) and concentrated. The residue is kugelrohr distilled at 1 torr to give 17.97 g (37.8%) of the desired product which is a liquid, n$_D^{25}$ 1.4465.

Anal. Calc'd. for C$_{16}$H$_{18}$F$_5$N$_1$O$_4$: C, 50.13; H, 4.73; N, 3.65; Found: C, 50.16; H, 4.76; N, 3.65.

EXAMPLE 16

Preparation of diethyl 2-(difluoromethyl)-4-isobutyl-6-(trifluoromethyl)-3,5-pyridinedicarboxylate A mixture of 10.0 g (0.0240 mole) of diethyl 2,6-bis(trifluoromethyl)-1,4-dihydro-4-isobutyl-3,5-pyridinedicarboxylate, 3.65 g (0.0240 mole) of DBU and 150 ml of THF is held at reflux for 18 hours and concentrated. The residue is dissolved in ether and washed with diluted hydrochloric acid, dried (MgSO$_4$) and concentrated. The residue is kugelrohr distilled at 0.1 torr to give 4.80 g (50%) of the desired product as an oil, n$_D^{25}$ 1.4436.

Anal. Calc'd. for C$_{17}$H$_{20}$F$_5$N$_1$O$_4$: C, 51.39; H, 5.07; N, 3.53; Found: C, 51.35; H, 5.08; N, 3.51.

EXAMPLE 17

Preparation of diethyl 2-(difluoromethyl)-4-cyclopropyl-6-(trifluoromethyl)-3,5-pyridinedicarboxylate To a solution of 40 g (0.0916 mole) of diethyl 2,6-bis(trifluoromethyl)-2,6-dihydroxy-4-cyclopropyl-tetrahydropyran-3,5-dicarboxylate in 200 ml of THF is introduced 55.5 g (3.26 moles) of ammonia. The reaction mixture is concentrated to give 38.5 g (96.7%) of a solid. A portion (28 g) of this material is stirred with 27.08 g (0.129 mole) of trifluoroacetic anhydride for one day. The reaction mixture is concentrated and diluted with ether. The ether solution is washed with saturated sodium bicarbonate, dried (MgSO$_4$), and concentrated to give 21 g (81.3%) of an oil, n$_D^{25}$ 1.4460. This oil is identified as diethyl 2,6-bis(trifluoromethyl)-4-cyclopropyl-1,4-dihydro-pyridine-3,5-dicarboxylate. A portion (18 g) of this oil and 150 ml of THF is treated with 6.82 g (0.0449 mole) of DBU. The reaction mixture is held at reflux for 24 hours and concentrated. The residue is stirred with water and extracted with ether. The ether extract is washed with diluted HCl, dried (MgSO$_4$), and concentrated. The residue is crystallized to give 13 g (76.0%) of crude product. A portion (2.0 g) of this product is recrystallized from petroleum ether at low temperature to give 1.17 g (85%) of desired product, m.p. 30°–32° C.

Anal. Calc'd. for C$_{16}$H$_{16}$F$_5$N$_1$O$_4$: C, 50.40; H, 4.23; N, 3.67; Found: C, 50.48; H, 4.32; N, 3.78.

In a manner similar to Example 12, other unsymmetrical pyridine compounds of this invention are prepared as indicated in Table 5.

TABLE 5
PREPARATION OF UNSYMMETRICAL DIETHYL PYRIDINEDICARBOXYLATES

| Ex. No. | Starting Material | Compound | Empirical Formula | m.p. °C. | $n_D^{25}$ | Element | Analysis Calc'd % | Found % |
|---|---|---|---|---|---|---|---|---|
| 18 | kk | Diethyl 2-(difluoromethyl)-4-methyl-6-(trifluoromethyl)-3,5-pyridinedicarboxylate | $C_{14}H_{14}O_4N_1F_5$ | | 1.4410 | C<br>H<br>N | 47.33<br>3.97<br>3.94 | 47.25<br>4.02<br>3.87 |
| 19 | vv | Diethyl 2-(difluoromethyl)-4-phenylmethoxymethyl-6-(trifluoromethyl)-3,5-pyridinedicarboxylate | $C_{21}H_{20}F_5N_1O_5$ | 48–51.5 | | C<br>H<br>N | 54.67<br>4.37<br>3.04 | 54.43<br>4.17<br>3.01 |
| 20 | oo | Diethyl 2-(difluoromethyl)-4-n-butyl-6-(trifluoromethyl)-3,5-pyridinedicarboxylate | $C_{17}H_{20}F_5N_1O_4$ | | 1.4443 | C<br>H<br>N | 51.39<br>5.07<br>3.53 | 51.43<br>5.17<br>3.48 |
| 21 | uu | Diethyl 2-(difluoromethyl)-4-cyclohexyl-6-(trifluoromethyl)-3,5-pyridinedicarboxylate | $C_{19}H_{22}F_5N_1O_4$ | | 1.4614 | C<br>H<br>N | 53.90<br>5.24<br>3.31 | 54.19<br>5.33<br>3.51 |
| 22 | aaa | Diethyl 2-(difluoromethyl)-4-(1-ethylpropyl)-6-(trifluoromethyl)-3,5-pyridinedicarboxylate | $C_{18}H_{22}F_5N_1O_4$ | | 1.4489 | C<br>H<br>N | 52.55<br>5.39<br>3.40 | 52.59<br>5.43<br>3.33 |
| 23 | zz | Diethyl 2-(difluoromethyl)-4-(methylthioethyl)-6-(trifluoromethyl)-3,5-pyridinedicarboxylate | $C_{16}H_{18}F_5N_1O_4S_1$ | | 1.4709 | C<br>H<br>N | 46.26<br>4.37<br>3.37 | 46.40<br>4.41<br>3.42 |
| 24 | ww | Diethyl 2-(difluoromethyl)-4-(methoxymethyl)-6-(trifluoromethyl)-3,5-pyridinedicarboxylate | $C_{15}H_{16}F_5N_1O_5$ | | 1.4448 | C<br>H<br>N | 46.76<br>4.19<br>3.68 | 46.83<br>4.21<br>3.88 |
| 25 | yy | Diethyl 2-(difluoromethyl)-4-(methylthiomethyl)-6-(trifluoromethyl)-3,5-pyridinedicarboxylate | $C_{15}H_{16}F_5N_1O_4S_1$ | | 1.4748 | C<br>H<br>N | 44.89<br>4.02<br>3.49 | 45.04<br>4.07<br>3.35 |
| 26 | eee | Diethyl 2-(difluoromethyl)-4-(1-methylpropyl)-6-(trifluoromethyl)-3,5-pyridinedicarboxylate | $C_{17}H_{20}F_5N_1O_4$ | | 1.4471 | C<br>H<br>N | 51.39<br>5.07<br>3.53 | 51.32<br>5.08<br>3.50 |

EXAMPLE 27

Preparation of diethyl 2-(difluoromethyl)-4-(2,2-dimethylpropyl)-6-(trifluoromethyl)-3,5-pyridinedicarboxylate To a solution of 11.0 g (0.105 mole) of 3,3-dimethylbutanol in 20 ml of methylene chloride is added 3.11 g (0.15 mole) of pyridinium chlorochromate. The mixture is stirred for 2 hours. The methylene chloride solution is decanted and filtered through a silica gel column. The silica gel column is washed with 200 ml of methylene chloride. The combined methylene chloride solution is concentrated at reduced pressure at 20° C. to give 3.7 g of a residue which is 66% pure 2,2-dimethylbutyraldehyde.

A mixture of the above aldehyde, 14 g (0.076 mole) of ethyl trifluoroacetoacetate, 0.5 ml of piperidine, and 50 ml of THF is held at reflux for 3 days and cooled to room temperature. To the above THF solution is passed 36 g of ammonia in one hour. The reaction mixture is stirred with 100 ml of water and 100 ml of ether. The ether layer is separated, dried, and concentrated to give 14.9 g of a residue. The residue is poured into a cold (10° C.) mixture of 50 ml concentrated sulfuric acid and 50 ml of methylene chloride. The mixture is stirred for 10 minutes and poured onto 300 g of crushed ice. The methylene chloride layer is separated, dried, and concentrated. The residue is kugelrohr distilled at 0.4 torr. The earlier fraction (pot temperature 90° C.) is discarded. The second fraction (pot temperature 120° C.) is 5.3 g of an oil which is purified by HPLC using 10% ethyl acetate/cyclohexane as eluent. The first fraction is 4.83 g of a syrup identified as diethyl 2,6-bis(trifluoromethyl)-1,4-dihydro-4-(2,2-dimethylpropyl)-3,5-pyridinedicarboxylate. A mixture of 3.83 g (0.0089 mole) of the above syrup, 1.41 g (0.0089 mole) of DBU and 50 ml of THF is held at reflux for 20 hours and concentrated. The residue is stirred with 100 ml of 6N HCl and 100 ml of ether and filtered. The ether filtrate is separated, washed successively with water, saturated sodium bicarbonate, saturated sodium chloride, dried, and concentrated. The residue is kugelrohr distilled at 1 torr (pot temperature 130° C.) to give 1.9 g of an oil which is purified by HPLC using 3% ethyl acetate/chloride as eluent. The earlier fraction is discarded. The second fraction affords 1.4 g of the desired product, $n_D^{25}$ 1.4522.

Anal. Calc'd for $C_{18}H_{22}F_5N_1O_4$: C, 52.55; H, 5.39; N, 3.40; Found: C, 52.54, H, 5.42; N, 3.40.

The mono-acid compounds, represented by the Formula III, are prepared by selective hydrolysis of diester compounds of Formula II as illustrated by the following examples of 28–37:

EXAMPLE 28

Preparation of 2-(difluoromethyl)-4-ethyl-6-(trifluoromethyl)-3,5-pyridinedicarboxylic acid, 5-ethyl ester A mixture of 18.5 g (0.050 mole) of the product of Example 12, 3.3 g (0.072 mole) of 85% potassium hydroxide, and 100 ml of ethanol is stirred for 18 hours and poured into water. The reaction mixture is extracted with 200 ml of ether. The aqueous layer is acidified with 50 ml of concentrated hydrochloric acid. The oily precipitate is extracted into ether (2×100 ml) and the ether extracts dried (MgSO4) and concentrated. The residual solid is recrystallized from ether-petroleum ether to give 14.4 g (84.7%) of the desired product, m.p. 117°–120° C.

Anal. Calc'd. for $C_{13}H_{12}F_5N_1O_4$: C, 45.76; H, 3.54; N, 4.10; Found: C, 45.77; H, 3.42; N, 4.09.

EXAMPLE 29

Preparation of 2-(difluoromethyl)-4-propyl-6-(trifluoromethyl)-3,5-pyridinedicarboxylic acid, 5-ethyl ester A 500 ml flask is charged with 32 g (0.0835 mole) of the product of Example 13 and 150 ml of ethanol. In a separate flask, 5.51 g (0.0835 mole) of 85% potassium hydroxide and 75 ml of water are combined. The aqueous KOH is poured into the 500 ml flask and the mixture heated to reflux for 18 hours. The reaction mixture is concentrated and stirred in water. The aqueous solution is acidified with concentrated HCl and extracted with ethyl ether. The organics are dried over anhydrous $MgSO_4$, filtered, and concentrated to yield 23.15 g (78%) of the desired product, m.p. 98°–100° C.

Anal. Calc'd for $C_{14}H_{14}O_4N_1F_5$: C, 47.32; H, 3.98; N, 3.94; Found: C, 47.45; H, 3.99; N, 3.95.

EXAMPLE 30

Preparation of 2-(difluoromethyl)-4-isobutyl-6-(trifluoromethyl)-3,5-pyridinedicarboxylic acid, 5-methyl ester A mixture of 6.4 g (0.0173 mole) of the product of Example 14, 1.2 g (0.0182 mole) of 85% KOH, 30 ml of methanol, and 2 ml of water is stirred for 2 days and concentrated. The residue was stirred with 200 ml of water and extracted with ether. The aqueous layer is made acidic with concentrated HCl and the oily precipitate is extracted into ether (2×100 ml). The ether extracts are dried and concentrated to give 5.9 g of solid which is recrystallized from hexane to give 4.9 g of the desired product as solid, m.p. 100°–102° C.

Anal. Calc'd. for $C_{14}H_{14}F_5N_1O_4$: C, 47.33; H, 3.97; N, 3.94; Found: C, 47.40; H, 3.97; N, 3.90.

In a manner similar to Examples 28, 29, and 30, other 2-(difluoromethyl)-6-(trifluoromethyl)-3,5-pyridinedicarboxylic acid 5-ethyl esters of this invention are prepared as indicated in Table 6 by hydrolysis of the listed starting material.

TABLE 6

3,5-PYRIDINEDICARBOXYLIC ACID, 5-MONOESTERS

| Ex. No. | Product | Starting Material | Empirical Formula | m.p. °C. | $n_D^{25}$ | Element | Calc'd % | Found % |
|---|---|---|---|---|---|---|---|---|
| 31 | 2-(difluoromethyl)-4-isopropyl-6-(trifluoromethyl)-3,5-pyridinedicarboxylic acid, 5-ethyl ester | Ex. 15 | $C_{14}H_{14}F_5N_1O_4$ | 80–87 | | C<br>H<br>N | 47.33<br>3.97<br>3.94 | 47.56<br>4.19<br>3.62 |
| 32 | 2-(difluoromethyl)-4-isobutyl-6-(trifluoromethyl)-3,5-pyridinedicarboxylic acid, 5-ethyl ester | Ex. 16 | $C_{15}H_{16}F_5N_1O_4$ | | 1.4453 | C<br>H<br>N | 48.79<br>4.37<br>3.79 | 48.55<br>4.51<br>3.66 |
| 33 | 2-(difluoromethyl)-4-n-butyl-6-(trifluoromethyl)-3,5-pyridinedicarboxylic acid, 5-ethyl ester | Ex. 20 | $C_{15}H_{16}F_5N_1O_4$ | 83–85 | | C<br>H<br>N | 48.79<br>4.37<br>3.79 | 48.86<br>4.36<br>3.71 |
| 34 | 2-(difluoromethyl)-4-cyclopropyl-6-(trifluoromethyl)-3,5-pyridinedicarboxylic acid, 5-ethyl ester | Ex. 17 | $C_{14}H_{12}F_5N_1O_4$ | 113–115 | | C<br>H<br>N | 47.60<br>3.42<br>3.97 | 47.67<br>3.56<br>3.92 |
| 35 | 2-(difluoromethyl)-4-(methylthioethyl)-6-(trifluoromethyl)-3,5-pyridinedicarboxylic acid, 5-ethyl ester | Ex. 23 | $C_{14}H_{14}F_5N_1O_4S_1$ | 121.5–122.5 | | C<br>H<br>N | 43.41<br>3.64<br>3.62 | 43.51<br>3.69<br>3.62 |
| 36 | 2-(difluoromethyl)-4-(methoxymethyl)-6-(trifluoromethyl)-3,5-pyridinedicarboxylic acid, 5-ethyl ester | Ex. 24 | $C_{13}H_{12}F_5N_1O_5$ | 108–108.5 | | C<br>H<br>N | 43.71<br>3.39<br>3.92 | 43.68<br>3.45<br>3.88 |
| 37 | 2-(difluoromethyl)-4-cyclohexyl-6-(trifluoromethyl)-3,5-pyridinedicarboxylic acid, 5-ethyl ester | Ex. 21 | $C_{17}H_{18}F_5N_1O_4$ | 88–91 | | C<br>H<br>N | 51.65<br>4.59<br>3.54 | 51.45<br>4.58<br>3.60 |

The pyridinedicarboxylic acids of Formula V in this invention are prepared by complete hydrolysis of compounds of Formula (D) and II as illustrated by the following examples of 38–43.

EXAMPLE 38

Preparation of 2,6-bis(trifluoromethyl)-4-ethyl-3,5-pyridinecarboxylic acid

A single-necked flask is charged with 10 g (0.025 mole) of the product of Example 1 and 100 ml of 10% aqueous KOH. The mixture is refluxed for 48 hours and the aqueous mixture is extracted once with ethyl ether. The water layer is acidified with concentrated HCl and the organics are extracted twice with ether, dried over $MgSO_4$, and concentrated to give 2.73 g (32.23%) of the desired product, m.p. 263°–269° C. (decomp.).

Anal. Calc'd. for $C_{11}H_7O_4N_1F_6$: C, 39.87; H, 2.11; N, 4.22; F, 34.44; Found: C, 39.92; H, 2.22; N, 4.17; F, 34.60.

EXAMPLE 39

Preparation of 2-(difluoromethyl)-4-n-propyl-6-(trifluoromethyl)-3,5-pyridinedicarboxylic acid A mixture of 20.1 g (0.0525 mole) of the product of Example 13, 11.4 g of 85% KOH, and 100 ml of methanol is held at reflux for 19 hours and concentrated. The residue is treated with 200 ml of water and extracted with ether. The aqueous layer is separated and acidified with 30 ml of concentrated HCl. The oily precipitate is extracted into ether and the ether extract is dried and concentrated. The residue is recrystallized from chloroform to give 4.2 g (24%) of the desired product, m.p. 235.5°–236.5° C.

Anal. Calc'd. for $C_{12}H_{10}F_5NO_4$: C, 44.05; H, 3.08; N, 4.28; Found: C, 43.92; H, 2.98; N, 4.19.

The combined mother liquor is concentrated and the residue treated with 10 g of KOH, 50 ml of methanol, and 2 ml of water as described above to give an additional 2.2 g (12.8%) of the desired product.

EXAMPLE 40

Preparation of 6-(difluoromethyl)-4-ethyl-2-(trifluoromethyl)-3,5-pyridinedicarboxylic acid A 1-liter flask is charged with 60 g (0.163 mole) of the product of Example 12 and 200 ml of methyl alcohol. In another flask, 150 ml of water and 21.52 g (0.326 mole) of potassium hydroxide are combined. The aqueous KOH is poured into the 1-liter flask and the mixture is heated to reflux overnight. The reaction mixture is cooled and extracted once with ethyl ether. The aqueous layer is acidified with concentrated hydrochloric acid and extracted with ethyl ether. The organics are dried on anhydrous magnesium sulfate, filtered, and concentrated to yield 26.72 g (52%) of the desired product, m.p. 237°–239° C.

Anal. Calc'd. for $C_{11}H_8O_4N_1F_5$: C, 42.17; H, 2.55; N, 4.47; Found: C, 43.29; H, 2.81; N, 4.34.

In a manner similar to Examples 39 and 40, other unsymmetrical pyridinedicarboxylic acids of this invention are prepared as indicated in Table 7 utilizing the starting material listed in Table 7.

TABLE 7

| Ex. No. | Product | Starting Material | Empirical Formula | m.p. °C. | $n_D^{25}$ | Element | Calc'd % | Found % |
|---|---|---|---|---|---|---|---|---|
| 41 | 2-(difluoromethyl)-4-isopropyl-6-(trifluoromethyl)-3,5-pyridinedicarboxylic acid | Ex. 15 | $C_{12}H_{10}F_5N_1O_4$ | 278 (dec) | | C<br>H<br>N | 44.05<br>3.08<br>4.28 | 43.99<br>3.10<br>4.24 |
| 42 | 2-(difluoromethyl)-4-methoxymethyl-6-(trifluoromethyl)-3,5-pyridinedicarboxylic acid | Ex. 24 | $C_{11}H_8F_5N_1O_5$ | 243–247 | | C<br>H<br>N | 40.14<br>2.45<br>4.26 | 39.95<br>2.66<br>4.22 |
| 43 | 2-(difluoromethyl)-4-isobutyl-6-(trifluoromethyl)-3,5-pyridinedicarboxylic acid | Ex. 14 | $C_{13}H_{12}F_5N_1O_4$ | 219–219.5 | | C<br>H<br>N | 45.76<br>3.54<br>4.10 | 45.66<br>3.57<br>4.08 |

The mono acid chlorides and diacid chlorides in this invention represented by the Formula IV and VI are prepared from the corresponding mono acids and diacids as illustrated by the following Examples 44–51:

EXAMPLE 44

Preparation of ethyl 5-chlorocarbonyl-6-(difluoromethyl)-4-isopropyl-2-(trifluoromethyl)-pyridine-3-carboxylate A mixture of 3.72 g (0.105 mole) of the product of Example 31 and 50 ml of thionyl chloride is held at reflux for 18 hours and concentrated in vacuo to give 3.8 g (97%) of the desired product as an oil, $n_D^{25}$ 1.4570.

Anal. Calc'd. for $C_{14}H_{13}Cl_1F_5NO_3$: C, 45.00; H, 3.51; N, 3.75; Found: C, 45.10; H, 3.53; N, 3.68.

In a manner similar to Example 44, other monoacid chlorides and diacid chlorides of this invention are prepared from the indicated starting materials and listed in Table 8.

TABLE 8

| Ex. No. | Product | Starting Material | Empirical Formula | m.p. °C. | $n_D^{25}$ | Element | Calc'd % | Found % |
|---|---|---|---|---|---|---|---|---|
| 45 | 6-(difluoromethyl)-4-ethyl-2-(trifluoromethyl)-3,5-pyridinedicarboxylic diacid chloride | Ex. 40 | $C_{11}H_6O_2N_1F_5Cl_2$ | | 1.4706 | C<br>H<br>N | 37.74<br>1.73<br>4.00 | 37.83<br>2.12<br>3.70 |
| 46 | ethyl 5-chlorocarbonyl-6-(difluoromethyl)-4-ethyl-2-(trifluoromethyl)-3-pyridinecarboxylate | Ex. 28 | $C_{13}H_{11}O_3N_1F_5Cl$ | | 1.4583 | C<br>H<br>N | 43.45<br>3.06<br>3.89 | 43.60<br>3.09<br>3.91 |
| 47 | ethyl 5-chlorocarbonyl-6-(difluoromethyl)-4-propyl-2-(trifluoromethyl)-3-pyridinecarboxylate | Ex. 29 | $C_{14}H_{13}O_3N_1F_5Cl$ | 33–34 | | C<br>H<br>N | 44.99<br>3.48<br>3.74 | 45.02<br>3.52<br>3.71 |
| 48 | 2,6-bis(trifluoro- | Ex. 38 | $C_{11}H_5O_2N_1F_6Cl_2$ | | 1.4509 | C | 35.90 | 36.05 |

TABLE 8-continued

| Ex. No. | Product | Starting Material | Empirical Formula | m.p. °C. | $n_D^{25}$ | Element | Calc'd % | Found % |
|---|---|---|---|---|---|---|---|---|
| | methyl)-4-ethyl-3,5-pyridinedicarboxylic acid diacid chloride | | | | | H | 1.37 | 1.43 |
| | | | | | | N | 3.81 | 3.73 |
| 49 | ethyl 5-(chlorocarbonyl)-4-n-butyl-6-(difluoromethyl)-2-(trifluoromethyl)-3-pyridinecarboxylate | Ex. 33 | $C_{15}H_{15}Cl_1F_5N_1O_3$ | 46–48 | | C | 46.47 | 46.33 |
| | | | | | | H | 3.90 | 3.78 |
| | | | | | | N | 3.61 | 3.58 |
| 50 | ethyl 5-(chlorocarbonyl)-4-cyclopropyl-6-(difluoromethyl)-2-(trifluoromethyl)-3-pyridinecarboxylate | Ex. 34 | $C_{14}H_{11}Cl_1F_5N_1O_3$ | 53–54 | | C | 45.24 | 45.24 |
| | | | | | | H | 2.98 | 3.01 |
| | | | | | | N | 3.77 | 3.78 |
| 51 | 2-(difluoromethyl)-4-propyl-6-(trifluoromethyl)-3,5-pyridinedicarboxylic acid diacid chloride | Ex. 39 | $C_{12}H_8O_2N_1F_5Cl_2$ | | 1.4713 | C | 39.58 | 39.61 |
| | | | | | | H | 2.21 | 2.34 |
| | | | | | | N | 3.85 | 3.50 |

EXAMPLE 52

Preparation of 3-ethyl 5-methyl 6-(difluoromethyl)-4-propyl-2-(trifluoromethyl)-3,5-pyridinedicarboxylate A mixture of 5.0 g of the product of Example 47 and 100 ml of methanol is held at reflux for 18 hours and concentrated. The residue is dissolved in ether. The ether solution is washed with aqueous saturated sodium bicarbonate, dried, and concentrated to give 2.37 g (48%) of the desired product as an oil, $n_D^{25}$ 1.4428.

Anal. Calc'd. for $C_{15}H_{16}F_5N_1O_4$: C, 48.92; H, 4.11; N, 3.80; Found: C, 49.00; H, 4.13; N, 3.76.

EXAMPLE 53

Preparation of 3-ethyl 5-methyl 6-(difluoromethyl)-4-isopropyl-2-(trifluoromethyl)-3,5-pyridinedicarboxylate A mixture of 2.8 g (0.0074 mole) of the product of Example 44 and 60 ml of methanol is held at reflux for 3 hours and concentrated to give 1.61 g (59%) of the desired product as an oil, $n_D^{25}$ 1.4483.

Anal. Calc'd. for $C_{15}H_{16}F_5N_1O_4$: C, 48.79; H, 4.37; N, 3.79; Found: C, 48.69; H, 4.41; N, 3.75.

EXAMPLE 54

Preparation of 3-methyl 5-ethyl 2-(difluoromethyl)-4-isobutyl-6-(trifluoromethyl)-3,5-pyridinedicarboxylate A mixture of 10 g (0.0270 mole) of the product of Example 32 and 100 ml of thionyl chloride is held at reflux overnight and concentrated to give a residue (9.59 g). A portion (5.03 g) of this residue is held at reflux with 50 ml of methanol for 3 hours and concentrated. The residue (3.72 g) is kugelrohr distilled to give 2.83 g (56.3%) of the desired product as an oil, $N_D^{25}$ 1.4453.

Anal. Calc'd. for $C_{16}H_{18}F_5N_1O_4$: C, 50.13; H, 4.73; N, 3.65; Found: C, 49.91; H, 4.87; N, 3.43.

EXAMPLE 55

Preparation of 3-ethyl 5-methyl 4-cyclopropyl-6-(difluoromethyl)-2-(trifluoromethyl)-3,5-pyridinedicarboxylate A mixture of 3.0 g (0.008 mole) of the product of Example 50 and 30 ml of methanol is held at reflux for 1.5 hours and concentrated. The residue (2.81 g) is recrystallized from petroleum ether to to give 1.85 g (63.1%) of the desired product as a white solid, m.p. 61°–63° C.

Anal. Calc'd. for $C_{15}H_{14}F_5N_1O_4$: C, 49.05; H, 3.81; N, 3.81; Found: C, 48.99; H, 3.88; N, 3.79.

A second crop (0.69 g, 23.5%) is also isolated from the mother liquor, m.p. 49°–52° C.

EXAMPLE 56

Preparation of dimethyl-2,6-bis(trifluoromethyl)-4-ethyl-3,5-pyridinedicarboxylate To 70 ml of methanol in a 500 ml flask is added 5 g (0.0136 mole) of product of Example 48. The reaction mixture is heated to reflux and refluxed for 9 hours. The mixture is concentrated, diluted with ethyl ether, washed with aqueous saturated sodium bicarbonate solution, dried in anhydrous MgSO4, and concentrated to yield 3.3 g (68%) of the desired product, m.p. 45°–47° C.

Anal. Calc'd. for $C_{13}H_{11}O_4N_1F_6$: C, 43.45; H, 3.06; N 3.89; Found: C, 43.57; H, 3.06; N, 3.86.

In a manner similar to the procedure of Examples 52–56 above, other novel compounds of this invention are prepared. As noted above with respect to Table 4, having due regard for the starting material substituted and reaction conditions, suitable to the reactants employed, additional examples are provided as noted in Table 9 below.

TABLE 9

MIXED ESTERS OF 3, 5-PYRIDINEDICARBOXYLIC ACIDS

| Ex. No. | Starting Material | Reactant | Product | Empirical Formula | m.p. °C. | $n_D^{25}$ | Element | Calc'd % | Found % |
|---|---|---|---|---|---|---|---|---|---|
| 57 | Ex. 46 | isopropanol | 5-ethyl 3-isopropyl-2-(difluoromethyl)-4-ethyl-6- | $C_{16}H_{18}O_4N_1F_5$ | | 1.4440 | C | 50.13 | 50.12 |
| | | | | | | | H | 4.69 | 4.72 |
| | | | | | | | N | 3.65 | 3.66 |

TABLE 9-continued
MIXED ESTERS OF 3, 5-PYRIDINEDICARBOXYLIC ACIDS

| Ex. No. | Starting Material | Reactant | Product | Empirical Formula | m.p. °C. | $n_D^{25}$ | Analysis Element | Calc'd % | Found % |
|---|---|---|---|---|---|---|---|---|---|
| 58 | Ex. 45 | butanol | (trifluoromethyl)-3,5-pyridinedicarboxylate dibutyl 6-(difluoromethyl)-4-ethyl-2-(trifluoromethyl)-3,5-pyridinedicarboxylate | $C_{19}H_{24}O_4N_1F_5$ | | 1.4467 | C H N | 53.65 5.69 3.29 | 53.05 5.55 3.37 |
| 59 | Ex. 45 | methanol | dimethyl 2-(difluoromethyl)-4-ethyl-6-(trifluoromethyl)-3,5-pyridinedicarboxylate | $C_{13}H_{12}O_4N_1F_5$ | 47–49 | | C H N | 45.74 3.51 4.10 | 45.79 3.57 4.07 |
| 60 | Ex. 48 | isopropanol | bis(isopropyl) 2,6-bis(trifluoromethyl)-4-ethyl-3,5-pyridinedicarboxylate | $C_{17}H_{19}O_4N_1F_6$ | 46–49 | | C H N | 49.15 4.57 3.37 | 49.21 4.63 3.37 |
| 61 | Ex. 46 | allyl alcohol | 3-ethyl 5-(2-propenyl) 6-difluoromethyl)-4-ethyl-2-(trifluoromethyl)-3,5-pyridinedicarboxylate | $C_{16}H_{16}O_4N_1F_5$ | | 1.4525 | C H N | 50.39 4.19 3.67 | 50.34 4.22 3.66 |
| 62 | Ex. 46 | 2-chloro ethanol | 5-ethyl 3-(2-chloroethyl) 2-(difluoromethyl)-4-ethyl-6-(trifluoromethyl)-3,5-pyridinedicarboxylate | $C_{15}H_{15}O_4N_1F_5Cl_1$ | | 1.4570 | C H N | 44.62 3.71 3.47 | 44.48 3.76 3.40 |
| 63 | Ex. 46 | methyl alcohol | 3-ethyl 5-methyl 6-(difluoromethyl)-4-ethyl-2-(trifluoromethyl)-3,5-pyridinedicarboxylate | $C_{14}H_{14}O_4N_1F_5$ | | 1.4448 | C H N | 47.32 3.94 3.94 | 47.23 3.99 3.92 |
| 64 | Ex. 46 | 2-fluoro ethanol | 3-ethyl 5-(2-fluoroethyl) 6-(difluoromethyl)-4-ethyl-2-(trifluoromethyl)-3,5-pyridinedicarboxylate | $C_{15}H_{15}F_6N_1O_4$ | | 1.4459 | C H | 46.52 3.90 | 46.76 4.20 |
| 65 | Ex. 49 | methanol | 3-ethyl 5-methyl-4-n-butyl-6-(difluoromethyl)-2-(trifluoromethyl)-3,5-pyridinedicarboxylate | $C_{16}H_{18}F_5N_1O_4$ | | 1.4465 | C H N | 50.13 4.73 3.65 | 49.97 4.77 3.64 |
| 66 | Ex. 49 | 2,2,2-trifluoroethanol | 3-ethyl 5-(2,2,2-trifluoroethyl)-4-n-butyl-6-(difluoromethyl)-3,5-pyridinedicarboxylate | $C_{17}H_{17}F_8N_1O_4$ | 37–38 | | C H N | 45.24 3.80 3.10 | 45.69 3.86 3.14 |
| 67 | Ex. 51 | methanol | dimethyl 2-(difluoromethyl)-4-n-propyl-6-(trifluoromethyl)-3,5-pyridinedicarboxylate | $C_{14}H_{14}F_5N_1O_4$ | | 1.4435 | C H N | 52.55 5.39 3.40 | 52.59 5.28 3.37 |
| 68 | Ex. 51 | n-propanol | dipropyl 2-(difluoromethyl)-4-n-propyl-6-(trifluoromethyl)-3,5-pyridinedicarboxylate | $C_{18}H_{22}F_5N_1O_4$ | | 1.4451 | C H N | 52.55 5.39 3.40 | 52.59 5.28 3.37 |

EXAMPLE 69

Preparation of 3-ethyl 5-methyl 2-(difluoromethyl)-4-isobutyl-6-(trifluoromethyl)-3,5-pyridinecarboxylate A mixture of 2.9 g (0.00817 mole) of the product of Example 30, 11 g (0.0705 mole) of ethyl iodide, 1.3 g (0.00942 mole) of potassium carbonate, and 50 ml of acetone is held at reflux for 4 hours and concentrated. The residue is treated with 200 ml of water and extracted with 50 ml of ether twice. The ether extracts are washed once with 50 ml of sodium bicarbonate, dried (MgSO$_4$), and concentrated to give an oil which is kugelrohr distilled at 2 torr (pot temperature 130° C.) to give 3.0 g (98%) of the desired product as a liquid, $n_D^{25}$ 1.4469.

Anal. Calc'd. for $C_{16}H_{18}F_5N_1O_4$: C, 50.13; H, 4.73; N, 3.65; Found: C, 50.19; H, 4.78; N, 3.56.

In a manner similar to the procedure of Example 69, other pyridinedicarboxylates of this invention are prepared. As noted above with respect to Table 4, having due regard for the starting material substituted and reaction conditions suitable to the reactants employed, additional examples are provided as noted in Table 10.

and concentrated to give 10.8 g of a syrup. Part (8.8 g) of this syrup is mixed with 34 g of methyl iodide, 3.16 g (0.0230 mole) of $K_2CO_3$ and 30 ml of acetone. The mixture was stirred and held at reflux for 3 hours and concentrated. The residue is stirred with 100 ml of ether and 100 ml of water. The ether solution is washed once with 50 ml of saturated $NaHCO_3$, dried ($MgSO_4$), and concentrated to give 7.6 g of a brown oil which is kugelrohr distilled at 1.5 torr (pot temperature of 115° C.) to give 7.6 g distillate. This distillate is chromatographed on silica gel by HPLC using 3% ethyl acetate-cyclohex-

TABLE 10
ALTERNATIVE PREPARATION OF PYRIDINEDICARBOXYLATE DERIVATIVES

| Ex. No. | Starting Material | Reactant | Solvent-Condition | Product | Empirical Formula | m.p. °C. | $n_D^{25}$ | Element | Calc'd % | Found % |
|---|---|---|---|---|---|---|---|---|---|---|
| 70 | Ex. 35 | KF—$CH_3I$ | DMF - room temperature | 3-ethyl 5-methyl 6-(difluoromethyl)-4-(methylthioethyl)-2-(trifluoromethyl)-3,5-pyridinedicarboxylate | $C_{15}H_{16}F_5N_1O_4S_1$ | 59-60.5 | | C H N | 44.89 4.02 3.49 | 44.87 4.02 3.47 |
| 71 | Ex. 36 | KF—$CH_3I$ | DMF - room temperature | 3-ethyl 5-methyl 6-(difluoromethyl)-4-(methoxymethyl)-2-(trifluoromethyl)-3,5-pyridinedicarboxylate | $C_{14}H_{14}F_5NO_5$ | 52-54 | | C H N | 45.29 3.80 3.77 | 45.08 3.79 3.69 |
| 72 | Ex. 41 | $K_2CO_3$—$CH_3I$ | acetone - reflux | dimethyl 2-(difluoromethyl)-4-isopropyl-6-(trifluoromethyl)-3,5-pyridinedicarboxylate | $C_{14}H_{14}F_5N_1O_4$ | | 1.4573 | C H N | 47.33 3.97 3.94 | 47.46 4.03 3.88 |
| 73 | Ex. 43 | $K_2CO_3$—$BrCH_2C{\equiv}CH$ | DMF - room temperature | dipropargyl 2-(difluoromethyl)-4-isobutyl-6-(trifluoromethyl)-3,5-(pyridinedicarboxylate | $C_{19}H_{16}F_5N_1O_4$ | | 1.4696 | C H N | 54.68 3.86 3.36 | 54.61 3.84 3.34 |
| 74 | Ex. 42 | $K_2CO_3$—$CH_3I$ | acetone - reflux | dimethyl 2-(difluoromethyl)-4-(methoxymethyl)-6-(trifluoromethyl)-3,5-pyridinedicarboxylate | $C_{13}H_{12}F_5N_1O_5$ | 43-44 | | C H N | 43.71 3.39 3.92 | 43.78 3.40 3.89 |

EXAMPLE 75

Preparation of 3-methyl 5-ethyl 2-(difluoromethyl)-4-(1-ethylpropyl)-6-trifluoromethyl)-3,5-pyridinedicarboxylate A 12.0 g (0.0386 mole) of a 90% pure product of Example 22, 2.6 g (0.0394 mole) of 85% potassium hydroxide, 30 ml of ethanol, and 2 ml of water is held at reflux for 20 hours and concentrated. The residue is treated with 100 ml of water and extracted with 100 ml of ether. The aqueous layer is acidified with 50 ml of concentrated HCl. The oil precipitate is extracted with 200 ml of ether. The ether solution is dried ($MgSO_4$)

ane as eluent. The first fraction (retention time 14–16 minutes) is 2.0 g of a mixture of the desired product and unidentified material. The second fraction (retention time 16–22 minutes) is 4.3 g of an oil which after kugelrohr distillation at 1 torr (pot temperature of 130° C.) gives 4.1 g of desired product as a colorless oil, $n_D^{25}$ 1.4519.

Anal. Calc'd. for $C_{17}H_{20}F_5NO_4$: C, 51.39; H, 5.07; N, 3.53; Found: C, 51.40; H, 5.14; N, 3.50.

Other pyridinedicarboxylic acid monoesters in this invention listed in Table 11 are prepared by a method similar to that described for Example 30.

TABLE 11
PYRIDINEDICARBOXYLIC ACID MONOESTERS

| Ex. No. | Compound | Starting Material | Empirical Formula | M.P. | Element | Calc'd | Found |
|---|---|---|---|---|---|---|---|
| 76 | 2-(difluoromethyl)-4-n-propyl-6-(trifluoromethyl)-3,5-pyridinedicarboxylic acid, 5-n-propyl ester | Ex. 68 | $C_{15}H_{16}F_5NO_4$ | 69-71 | C H N | 48.79 4.37 3.79 | 48.71 4.40 3.79 |
| 77 | 2-(difluoromethyl)-4-n-propyl-6-(trifluoromethyl)-3,5-pyridinedicarboxylic acid, | Ex. 67 | $C_{13}H_{12}F_5NO_4$ | 113-115 | C H N | 45.76 3.54 4.10 | 45.86 3.65 3.96 |

TABLE 11-continued
PYRIDINEDICARBOXYLIC ACID MONOESTERS

| Ex. No. | Compound | Starting Material | Empirical Formula | M.P. | Element | Calc'd | Found |
|---|---|---|---|---|---|---|---|
| 78 | 5-methyl ester 2-(difluoromethyl)-4-(methoxymethyl)-6-(trifluoromethyl)-3,5-pyridinedicarboxylic acid, 5-methyl ester | Ex. 74 | $C_{12}H_{10}F_5N_1O_5$ | 132–133.5 | C H N | 41.99 2.94 4.08 | 42.09 2.95 4.03 |
| 79 | 2-(difluoromethyl)-4-isobutyl-6-(trifluoromethyl)-3,5-pyridinedicarboxylic acid, 5-propargyl ester | Ex. 73 | $C_{16}H_{14}F_5N_1O_4$ | 98.5–99.5 | C H N | 50.67 3.72 3.69 | 50.56 3.75 3.63 |

EXAMPLE 80

Preparation of 3-methyl 5-propargyl 2-(difluoromethyl)-4-isobutyl-6-(trifluoromethyl)-3,5-pyridinedicarboxylate A mixture of 2.1 g of the product of Example 79, 1.1 g of potassium carbonate, 25.3 g of methyl iodide, and 40 ml of DMF is stirred for 24 hours and poured into water. The mixture is extracted with ether. The ether extract is washed twice with 100 ml of water, dried, and concentrated. The residue is kugelrohr distilled at 0.5 torr to give 2.1 g (96%) of the desired product as an oil, $n_D^{25}$ 1.4598.

Anal. Calc'd. for $C_{17}H_{16}F_5N_1O_4$: C, 51.91; H, 4.10; N, 3.56; Found: C, 51.92; H, 4.14; N, 3.56.

EXAMPLE 81

Preparation of 3-ethyl 5-methyl 2-(difluoromethyl)-4-(methoxymethyl)-6-(trifluoromethyl) 3,5-pyridinedicarboxylate In accordance with the procedure of Example 69 with the exception that the starting material is the product of Example 78, there is obtained 3-ethyl 5-methyl-2-(difluoromethyl)-4-(methoxymethyl)-6-trifluoromethyl)-3,5-pyridinedicarboxylate as an oil, $n_D^{25}$ 1.4467.

Anal. Calc'd. for $C_{14}H_{14}F_5N_1O_5$: C, 45.29; H, 3.80; N, 3.77; Found: C, 45.39; H, 3.84; N, 3.74.

Other 5-chlorocarbonyl-3-pyridinecarboxylates of this invention are prepared from the corresponding 3,5-pyridinedicarboxylic acid 3-monoester by a method similar to that described for Example 44 and are listed in Table 12.

TABLE 12

| Ex. No. | Compound | Starting Material | Empirical Formula | m.p. | $n_D^{25}$ | Element | Calc'd | Found |
|---|---|---|---|---|---|---|---|---|
| 82 | 3-methyl 5-chlorocarbonyl-6-(difluoromethyl)-4-n-propyl-2-(trifluoromethyl)-3-pyridinecarboxylate | Ex. 77 | $C_{13}H_{11}Cl_1F_5N_1O_3$ | 47–50 | | C H N | 43.41 3.08 3.89 | 43.62 3.05 3.76 |
| 83 | 3-propyl 5-chlorocarbonyl-6-(difluoromethyl)-4-n-propyl-2-(trifluoromethyl)-3-pyridinecarboxylate | Ex. 76 | $C_{15}H_{15}Cl_1F_5N_1O_3$ | | 1.4560 | C H N | 46.47 3.90 3.61 | 46.39 3.95 3.60 |

Other unsymmetrical pyridinedicarboxylates in this invention are prepared from the corresponding 5-chlorocarbonyl-3-pyridinecarboxylate and an appropriate alcohol by a method similar to that described in Example 52 and are listed in Table 13.

TABLE 13

| Ex. No. | Starting Material | Reactant | Product | Empirical Foumula | $n_D^{25}$ | Element | Calc'd % | Found % |
|---|---|---|---|---|---|---|---|---|
| 84 | Ex. 82 | n-propanol | 3-methyl 5-n-propyl 6-(difluromethyl)-4-n-propyl-2-(trifluoromethyl)-3,5-pyridinedicarboxylate | $C_{16}F_{18}F_5N_1O_4$ | 1.4447 | C H N | 50.13 4.73 3.65 | 50.25 4.73 3.62 |
| 85 | Ex. 83 | methanol | 3-methyl 5-n-propyl-2-(difluoromethyl)-4-n-propyl-6-(trifluoromethyl-3,5-pyridinedi carboxylate | $C_{16}H_{18}F_5N_1O_4$ | 1.4453 | C H N | 50.13 4.73 3.65 | 50.54 4.71 3.60 |
| 86 | Ex. 82 | ethanol | 3-methyl 5-ethyl 6-(difluoromethyl)-4-n-propyl-2-(trifluoromethyl)-3,5-pyridinedi- | $C_{15}H_{16}F_5N_1O_4$ | 1.4439 | C H N | 48.79 4.37 3.79 | 48.69 4.44 3.74 |

TABLE 13-continued

| Ex. No. | Starting Material | Reactant | Product | Empirical Foumula | $n_D^{25}$ | Analysis | | |
|---|---|---|---|---|---|---|---|---|
| | | | | | | Element | Calc'd % | Found % |
| | | | carboxylate | | | | | |

EXAMPLE 87

Preparation of 3-ethyl 5-methyl 2,6-bis(difluoro-methyl)-4-propyl-3,5-pyridinecarboxylate A mixture of 5.67 g (0.016 mol) of the product of Example 11, 1.06 g (0.016 mol) of 85% KOH, 40 ml of ethanol, and 10 ml of water is stirred for 24 hours and concentrated. The residue is treated with 50 ml of water and extracted with 50 ml of ether. The aqueous layer is acidified with 50 ml of concentrated HCl. The oil precipitate is extracted with ether, dried (MgSO$_4$), and concentrated to give 2.64 g (49%) of a monoacid. Part (1.64 g, 0.00486 mole) of this acid is refluxed with 10 ml of thionyl chloride until HCl evolution ceased. The reaction mixture is concentrated and the residue is dissolved in ether, dried over MgSO$_4$, and concentrated to give 1.22 g of the desired product as an oil, $n_D^{25}$ 1.4629.

Anal. Calc'd. for $C_{15}H_{17}F_4NO_4$: C, 51.29; H, 4.88; N, 3.99; Found: C, 50.93; H, 4.99; N, 3.87.

EXAMPLE 88

Preparation of ethyl 5-(aminocarbonyl) 6-difluoromethyl)-4-ethyl-2-(trifluoromethyl) 3-pyridinecarboxylate An excess of ammonia gas (3 g, 0.176 mole) is condensed into a three-necked 250 ml flask using dry ice acetone condensers. To 50 ml of ether is added 7 g (0.0196 mole) of the product of Example 46. The ether solution is slowly poured into the reaction flask and the total mixture is stirred for 18 hours. The resulting solid is washed with water and dried under vacuum for 18 hours to yield 5.67 g (86%) of the desired product, m.p. 165°–167° C.

Anal. Calc'd. for $C_{13}H_{13}O_3N_2F_5$: C, 45.88; H, 3.82; N, 8.23; Found: C, 45.87; H, 3.84; N, 8.23.

In a manner similar to Example 88, other pyridinecarboxamides of this invention are prepared as indicated in Table 14.

EXAMPLE 92

Preparation of ethyl 5-cyano-6-(difluoromethyl)-4-ethyl-2-(trifluoromethyl)-3-pyridinecarboxylate To 100 ml of phosphorus oxychloride in a 500 ml flask is added 3.5 g (0.0102 mole) of the product of example 88. The mixture is refluxed for 18 hours, concentrated, washed in water, and extracted with ethyl ether. The ether extracts are dried on anhydrous MgSO$_4$, concentrated, and dried under vacuum to yield 1.23 g (37%) of the desired product, m.p. 38°–40° C.

Anal. Calc'd. for $C_{13}H_{11}O_2N_2F_5$: C, 48.44; H, 3.41; N, 8.69. Found: C, 48.38; H, 3.48; N, 8.65.

EXAMPLE 93

Preparation of ethyl 5-cyano-6-(difluoromethyl)-4-n-propyl-2-(trifluoromethyl)-3-pyridinecarboxylate A mixture of 4.0 g (0.0112 mole) of the product of Example 91 and 100 g of phosphorus oxychloride is held at reflux for 20 hours and concentrated. The residue is poured into water and extracted with ether. The ether extract is dried (MgSO$_4$) and concentrated. The residue was kugelrohr distilled at 0.1 torr to give 2.26 g of an oil which is recrystallized from hexane at low temperature to give 1.11 g of the desired product as a solid, m.p. 40°–41° C.

Anal. Calc'd. for $C_{14}H_{13}F_5H_2O_2$: C, 50.01; H, 3.90; N, 8.33; Found: C, 49.75; H, 3.98; N, 8.21.

EXAMPLE 94

Preparation of diethyl 2,6-bis(trifluoromethyl)-4-(1-methyl-3-butenyl)-3,5-pyridinedicarboxylate A three-necked 250 ml flask is desiccated and purged with argon. Approximately 45 ml of dried tetrahydrofuran is injected into the flask via syringe. The flask is cooled at −78° C. and charged with 14 ml (0.0227 mole) of 1.6M n-butyl lithium followed by 2.96 ml (0.0227 mole) of diisopropyl amine. After stirring for 5 minutes, 8.8 g (0.0227 mole) of the product of Example 1 is diluted with 10 ml of dried tetrahydrofuran and

TABLE 14

| Ex. No. | Starting Material | Reactant | Product | Empirical Formula | m.p. °C. | Analysis % | | |
|---|---|---|---|---|---|---|---|---|
| | | | | | | Element | Calc'd | Found |
| 89 | Ex. 46 | butylamine | ethyl 5-[(butylamino)-carbonyl]-6-(difluoro-methyl)-4-ethyl-2-(trifluoromethyl)-3-pyridinecarboxylate | $C_{17}H_{21}O_3N_2F_5$ | 83–85 | C<br>H<br>N | 51.51<br>5.30<br>7.07 | 51.38<br>5.35<br>7.02 |
| 90 | Ex. 46 | aniline | ethyl 6-(difluoro-methyl)-4-ethyl-5-[(phenylamino)carbonyl]-2-(trifluoromethyl)-3-pyridinecarboxylate | $C_{19}H_{17}F_5N_2O_3$ | 182–183 | C<br>H<br>N | 54.80<br>4.08<br>6.73 | 54.69<br>4.13<br>6.68 |
| 91 | Ex. 47 | ammonia gas | ethyl 5-(amino-carbonyl)-6-(difluoro-methyl)-4-n-propyl-2-(trifluoromethyl)-3-pyridinecarboxylate | $C_{14}H_{15}O_3N_2F_5$ | 141–143 | C<br>H<br>N | 47.46<br>4.27<br>7.91 | 47.64<br>4.32<br>7.71 | injected into the flask. The mixture is stirred one hour. To this mixture is added 4.23 g (0.035 mole) of allyl bromide and the mixture stirred for 90 minutes at room temperature.

The mixture is diluted with ethyl ether and washed successively with water and 10% aqueous HCl. The organics are dried over $MgSO_4$ and concentrated. Chromatography in 5% ethyl acetate/cyclohexane yields 1.4 g (14.4%) of the desired product, $n_D^{25}$ 1.4410.

Anal. Calc'd. for $C_{18}H_{19}O_4N_1F_6$: C, 50.58; H, 4.44; N, 3.27; Found: C, 50.69; H, 4.47; N, 3.30.

EXAMPLE 95

Preparation of diethyl 2,6-bis(trifluoromethyl)-4-(3-butenyl)-3,5-pyridinedicarboxylate A three-necked 250 ml flask is heated, desiccated, and purged with argon. Tetrahydrofuran (50 ml) is injected via syringe and the flask is cooled to $-78°$ C. To this is added 8.33 ml (0.0133 mole) of 1.6M n-butyl lithium via syringe followed by 2 ml (0.0133 mole) of diisopropyl amine. To 10 ml of dried tetrahydrofuran, 5 g (0.0133 mole) of the product of Example 2 is added and the solution is injected into the reaction mixture. The mixture is stirred for an hour. Allyl bromide, 2.4 g (0.02 mole) is injected into the flask and the mixture is stirred for 90 minutes at room temperature.

The mixture is diluted with ethyl ether and washed successively with water and 10% HCl. The organics are dried, concentrated, and chromatographed with 5% ethyl acetate in cyclohexane to yield 0.7 g (29.26%) product; $n_D^{25}$ 1.4365.

Anal. Calc'd. for $C_{17}H_{17}O_4N_1F_6$: C, 49.39; H, 4.11; N, 3.39; Found: C, 49.54; H, 4.14; N, 3.36.

EXAMPLE 96

Preparation of ethyl 6-(difluoromethyl)4-ethyl-5-hydroxymethyl-2-(trifluoromethyl)3-pyridinecarboxylate To a dry 500 ml four-necked flask is charged 30.6 g (0.09 mole) of the product of Example 28 and 40 ml of tetrahydrofuran under nitrogen. The reaction mixture is cooled to 10° C. with an ice-water bath. To the above solution is added via a syringe 180 ml (0.18 mole) of 1M borane in tetrahydrofuran. The reaction mixture is stirred for 160 hours and poured into water. The organics are extracted into 300 ml of ether and the ether extract washed with 200 ml of saturated sodium bicarbonate, dried ($MgSO_4$), and concentrated. The residue is crystallized from petroleum ether to give 25 g (84.9%) of the desired product, m.p. 59.5°–60.5° C.

Anal. Calc'd. for $C_{13}H_{14}F_5N_1O_3$: C, 47.71; H, 4.31; N, 4.28; Found: C, 47.72; H, 4.31; N, 4.25.

EXAMPLE 97

Preparation of ethyl 6-(difluoromethyl)4-ethyl-5-formyl-2-(trifluoromethyl)-3-pyridinecarboxylate A mixture of 4.74 g (0.0145 mole) of the product of Example 96, 8.6 g (0.0336 mole) of pyridinium chlorochromate, and 70 ml of $CH_2Cl_2$ is held at room temperature for 18 hours. The $CH_2Cl_2$ solution is decanted and is chromatographed on silica gel using $CH_2Cl_2$ as eluent. The first 2 L eluate gives 3.93 g (83.4%) of the desired product as white solid, m.p. 63.5°–65° C.

Anal. Calc'd. for $C_{13}H_{12}F_5N_1O_3$: C, 48.01; H, 3.72; N, 4.31; Found: C, 48.02; H, 3.74; N, 4.28.

EXAMPLE 98

Preparation of diethyl 2-(difluoromethyl)4-(2-methylsulfonylethyl)-6-(trifluoromethyl-3,5-pyridinedicarboxylate To a solution of 12.0 g (0.0289 mole) of the product of Example 23 in 200 ml of methylene chloride is added 13.0 g (0.064 mole) m-chloroperbenzoic acid. The reaction mixture is stirred for 24 hours and poured into a mixture of 25 ml 10% sodium hydroxide and 400 ml of water. The methylene chloride layer is separated and washed successively with diluted sodium bicarbonate, sodium thiosulfate, saturated sodium chloride, dried, and concentrated to give 12.9 g of a solid. A portion (5.0 g) of this solid is purified by HPLC using 33% ethyl acetate/cyclohexane as eluent to give 3.6 g of the desired product, m.p. 98°–101° C.

Anal. Calc'd. for $C_{16}H_{18}F_5N_1O_6S$: C, 42.96; H, 4.06; N, 3.13; Found: C, 42.80; H, 4.06; N, 3.12.

EXAMPLE 99

Preparation of 3-ethyl 5-methyl 6-(difluoromethyl)-4-vinyl-2-(trifluoromethyl)-3,5-pyridinedicarboxylate A mixture of 17.31 g (0.0387 mole) of the product of Example 98, 2.16 g (0.054 mole) of sodium hydroxide, 125 ml of water, and 60 ml of ethanol is stirred for 24 hours and concentrated. The residue is stirred with ether and 600 ml of 1.5N sodium hydroxide. The aqueous layer is acidified with concentrated hydrochloric acid. The organic is extracted into methylene chloride (2×400 ml). The methylene chloride extracts were dried and concentrated to give 11.67 g of a residue. A mixture of the above residue, 14.70 g (0.104 ml) of methyl iodide, 14.3 (0.104 mole) of potassium carbonate, and 300 ml of acetone is refluxed for 18 hours and concentrated. The residue is stirred with 500 ml of water and 500 ml of ether. The ether layer is dried and concentrated. The residue (11.34 g) is kugelrohr distilled at 0.3 torr to give 7.50 g (62%) of the desired product, $n_D^{25}$ 1.4567.

Anal. Calc'd. for $C_{14}H_{12}F_5N_1O_4$: C, 47.60; H, 3.42; N, 3.97; Found: C, 47.46; H, 3.55; N, 3.85.

EXAMPLE 100

Preparation of diethyl 4-[2-(methylsulfinyl)-ethyl]-2-(difluoromethyl)-6-(trifluoromethyl)pyridine-3,5-dicarboxylate To a stirred solution of 20.09 g (0.048 mole) of product of Example 23 in 50 ml methylene chloride cooled in an ice bath is added a solution of 10.3 g (0.050 moles) of m-chloroperbenzoic acid in 100 ml methylene chloride holding the reaction temperature below 10° C. Stirring and cooling with an ice bath is continued for one hour after addition is complete.

The resulting slurry is poured into a solution prepared from 25 ml 10% sodium hydroxide and 600 ml of water. After mixing well, the phases are separated. The aqueous phase is extracted with 50 ml methylene chloride. The methylene chloride phases are combined, washed successively with solution, 600 ml of 0.5% sodium bicarbonate, 0.5% sodium chloride solution, dried over magnesium sulfate, filtered, and stripped, to give 20.5 g of light yellow solid.

The product is purified by recrystallizing twice from hexane/ether to give 12.5 g of white solid, m.p. 90.5°–91.5° C., 60% yield.

Anal. Calc'd. for $C_{16}H_{18}F_5N_1O_5S_1$: C, 44.55; H, 4.21; N, 3.25; Found: C, 44.45; H, 4.22; N, 3.20.

EXAMPLE 101

Preparation of 3-ethyl 5-methyl 6-(difluoromethyl)-4-(methylthiomethyl)-2-(trifluoromethyl)-3,5-pyridinedicarboxylate A mixture of 32.8 g (0.081 mole) of the crude product of Example 25, 37 g of 10% sodium hydroxide, 35 ml of water, and 125 ml of ethanol is stirred for one hour and concentrated. The residue is stirred with 700 ml of water and 200 ml of methylene chloride. The aqueous layer is made acidic and the precipitate is extracted into methylene chloride. The methylene chloride extract is dried and concentrated to give 19.9 g of an acid, m.p. 81°–85° C. A portion (10.6 g, 0.1078 mole) of this acid, 5.2 ml (0.085 mole) of methyl iodide, 11.8 g (0.085 mole) of potassium carbonate, and 150 ml of acetone are mixed and held at reflux for 24 hours. The reaction mixture is concentrated and the residue is stirred with 150 ml of methylene chloride and 200 ml of water. The methylene chloride layer is dried and concentrated. The residue is kugelrohr distilled at 0.25 torr (pot temperature 135°–170° C.) to give 7.16 g of a distillate. This distillate is purified by HPLC using 7% ethyl acetate/cyclohexane as eluent.

The earlier fraction (retention time 4–6 min) gives 4.75 g of a solid which is recrystallized twice from hexane/ether to give 2.78 g of the desired product, m.p. 67°–68.5° C.

Anal. Calc'd. for $C_{14}H_{14}F_5N_1O_4S_1$: C, 43.41; H, 3.64; N, 3.62; Found: C, 43.13; H, 3.61; N, 3.55.

EXAMPLE 102

Preparation of diethyl 6-(difluoromethyl)-2-(trifluoromethyl)-4-vinyl-3,5-pyridinedicarboxylate A mixture of 3.7 g of product of Example 99, 13.75 g of 10% sodium hydroxide, and 10 ml of water is stirred for 24 hours and concentrated. The residue is stirred with 300 ml of water and 50 ml of methylene chloride. The aqueous layer is acidified with concentrated hydrochloric acid and extracted with methylene chloride. The methylene chloride extract is dried and concentrated to give 2.99 g of a yellow solid which is recrystallized from petroleum ether to give 2.01 g of a white solid. A mixture of this solid, 1 ml of ethyl iodide, 10 ml of DMF, and 2.09 g of potassium carbonate is stirred for 24 hours and poured into 300 ml of water. The reaction mixture is extracted with methylene chloride and the methylene chloride extract dried and concentrated. The residue is kugelrohr distilled at 0.1 torr to give 1.41 g of the desired product, $n_D^{25}$ 1.4529.

Anal. Calc'd. for $C_{15}H_{14}F_5N_1O_4$: C, 49.05; H, 3.84; N, 3.81 Found: C, 49.09; H, 3.84; N, 3.81.

EXAMPLE 103

Preparation of diethyl 4-[(1-ethoxy)methoxymethyl]-2-(difluoromethyl)-6-(trifluoromethyl)-pyridine-3,5-dicarboxylate To a stirred solution of 4.0 g (0.010 mole) of the product of Example 24 in 30 ml of carbon tetrachloride is added 2.5 g (0.015 mole) of bromine. The solution is cooled to 10° C., a stream of dry nitrogen is passed over the reaction mixture (to purge hydrogen bromide), and the reaction is illuminated with a 150 watt spotlight. The reaction temperature is held at 10°–15° C. for 6 hours. The light is removed and the nitrogen stream stopped.

A solution of 1.41 g (0.013 mole) 2,6-lutidine in 5 ml absolute ethanol is added to the reaction mixture, and this resulting reaction mixture is stirred for 18 hours at ambient temperature.

The reaction mixture is poured into 100 ml water with 50 ml methylene chloride. After mixing well, the organic phase is separated, washed with 100 ml of 0.50% hydrochloric acid solution, 100 ml of 1% sodium bicarbonate, dried over magnesium sulfate, filtered, and stripped to give 4.29 g of yellow oil.

The product is purified by HPLC on silica gel using 10% ethylacetate in cyclohexane as a solvent to give 2.18 g of light yellow oil, yield 48%, $n_D^{25}$ 1.4446.

Anal. Calc'd. for $C_{17}H_{20}F_5N_1O_6$: C, 47.56; H, 4.70; N, 3.26; Found: C, 47.55; H, 4.71; N, 3.26.

In a manner similar to the procedure of Example 103, the product of Example 24 is brominated and the resulting product is reacted with an appropriate alcohol or alkylthiol as indicated in the following examples as noted in Table 15 to provide the product listed.

TABLE 15

| Ex. No. | Starting Material | Reactant | Product | Empirical Formula | $n_D^{25}$ | Element | Analysis % Calc'd | Found |
|---|---|---|---|---|---|---|---|---|
| 104 | Ex. 71 | methanol | 3-ethyl 5-methyl 6-(difluoromethyl)-4-(dimethoxymethyl)-2-(trifluoromethyl)-3,5-pyridinedicarboxylate | $C_{15}H_{16}F_5N_1O_6$ | 1.4428 | C<br>H<br>N | 44.90<br>4.02<br>3.49 | 44.71<br>3.81<br>3.45 |
| 105 | Ex. 71 | methanethiol | 3-ethyl 5-methyl 6-(difluoromethyl)-4-[methoxy(methylthio)methyl]-2-(trifluoromethyl-3,5-pyridinedicarboxylate | $C_{15}H_{16}F_5NO_5S$ | 1.4457 | C<br>H<br>N | 43.17<br>3.86<br>3.36 | 43.06<br>3.68<br>3.34 |

In a manner similar to Example 39, additional pyridinedicarboxylic acids of this invention are prepared as indicated in Table 16.

TABLE 16

| Ex. No. | Compound | Starting Material | Empirical Formula | m.p. °C. | Element | Analysis % Calc'd | Found |
|---|---|---|---|---|---|---|---|
| 106 | 2-(difluoromethyl)-4-(1-methylpropyl)- | Ex. 26 | $C_{13}H_{12}F_5NO_4$ | 222–225.5 | C<br>H | 45.76<br>3.54 | 45.71<br>3.71 |

TABLE 16-continued

| Ex. No. | Compound | Starting Material | Empirical Formula | m.p. °C. | Element | Analysis % Calc'd | Found |
|---|---|---|---|---|---|---|---|
| | 6-(trifluoromethyl)-3,5-pyridinedicarboxylic acid | | | | N | 4.10 | 3.88 |
| 107 | 2-(difluoromethyl)-4-(2,2-dimethylpropyl)-6-trifluoromethyl)-3,5-pyridinedicarboxylic acid | Ex. 27 | $C_{14}H_{14}F_5NO_4$ | 247–249 | C H N | 47.16 4.03 3.94 | 47.33 3.97 3.94 |
| 108 | 2-(difluoromethyl)-4-cyclopropyl-6-(trifluoromethyl)-3,5-pyridinedicarboxylic acid | Ex. 17 | $C_{12}H_8F_5N_1O_4$ | 260–264 (dec) | C H N | 44.32 2.48 4.31 | 44.22 2.52 4.26 |

In a manner similar to the procedure of Example 69, other pyridinedicarboxylates of this invention are prepared, with the exception that the reactions are conducted at room temperature. As noted above with respect to Table 10, having due regard for starting material substituted and reaction conditions suitable for the reactants employed, additional examples are provided as shown in Table 17.

TABLE 17

| Ex. No. | Starting Material | Reactant | Solvent-Condition | Product | Emperical Formula | $n_D^{25}$ | m.p. °C. | Element | Analysis % Calc'd | Found |
|---|---|---|---|---|---|---|---|---|---|---|
| 109 | Ex. 43 | $K_2CO_3$—$CH_3CH_2CH_2I$ | DMF | dipropyl 2-(difluoromethyl-4-isobutyl-6-(trifluoromethyl)-3,5-pyridinedicarboxylate | $C_{19}H_{24}F_5NO_4$ | 1.4473 | | C H N | 53.65 5.69 3.29 | 53.68 5.65 3.26 |
| 110 | Ex. 107 | $K_2CO_3$—$CH_3I$ | DMF | dimethyl 2-(difluoromethyl)-4-(2,2-dimethylpropyl)-6-(trifluoromethyl)-3,5-pyridinedicarboxylate | $C_{16}H_{18}F_5NO_4$ | | 77.5–77.8 | C H N | 50.13 4.73 3.65 | 50.06 4.49 3.61 |
| 111 | Ex. 106 | $K_2CO_3$—$CH_3I$ | DMF | dimethyl 2-(difluoromethyl)-4-(1-methylpropyl)-6-(trifluoromethyl)-3,5-pyridinedicarboxylate | $C_{15}H_{16}F_5NO_4$ | 1.4515 | | C H N | 48.79 4.37 3.79 | 48.90 4.39 3.77 |
| 112 | Ex. 41 | $K_2CO_3$—H—C≡C—$CH_2Br$ | DMF | dipropargyl 2-(difluoromethyl)-4-isopropyl-6-(trifluoromethyl)3,5-pyridinedicarboxylate | $C_{18}H_{14}F_5NO_4$ | 1.4698 | | C H N | 53.61 3.50 3.47 | 53.60 3.52 3.43 |
| 113 | Ex. 39 | $K_2CO_3$—H—C≡C—$CH_2Br$ | DMF | dipropargyl 2-(difluoromethyl)-4-n-propyl-6-(trifluoromethyl)-3,5-pyridinedicarboxylate | $C_{18}H_{14}F_5NO_4$ | 1.4713 | | C H N | 53.61 3.50 3.47 | 53.74 3.54 3.44 |
| 114 | Ex. 108 | $K_2CO_3$—$CH_3I$ | DMF | dimethyl 4-cyclopropyl-2-(difluoromethyl)-6-(trifluoromethyl)-3,5-pyridinedicarboxylate | $C_{14}H_{12}F_5N_1O_4$ | | 77–79 | C H N | 47.60 3.42 3.97 | 47.64 3.44 3.92 |
| 115 | Ex. 108 | $K_2CO_3$—HC≡$CCH_2Br$ | DMF | dipropargyl 4-cyclopropyl-2-(difluoromethyl)-6-(trifluoro- | $C_{18}H_{12}F_5N_1O_4$ | 1.4783 | | C H N | 53.87 3.01 3.49 | 53.46 3.27 3.45 |

TABLE 17-continued

| Ex. No. | Starting Material | Reactant | Solvent-Condition | Product | Empirical Formula | $n_D^{25}$ | m.p. °C. | Analysis % Element | Calc'd | Found |
|---|---|---|---|---|---|---|---|---|---|---|
| 116 | Ex. 37 | K$_2$CO$_3$—CH$_3$I | DMF | methyl)-3,5-pyridinedi-carboxylate 3-ethyl 5-methyl 4-cyclohexyl-2-(trifluoro-methyl)-6-(difluoro-methyl)-3,5-pyridinedi-carboxylate | C$_{18}$H$_{20}$F$_5$N$_1$O$_4$ | 1.4654 | | C<br>H<br>N | 52.81<br>4.92<br>3.42 | 52.73<br>4.93<br>3.39 |

EXAMPLE 117

Preparation of 3-methyl 5-propargyl 2-(difluoromethyl)-4-n-propyl-6-(trifluoromethyl)-3,5-pyridinedicarboxylate A mixture of 5.06 g (0.0125 mole) of product of Example 113, 1.24 g (0.0188 mole) of 85% potassium hydroxide, 65 ml of ethanol, and 50 ml of water is stirred for 48 hours and then extracted with ether. The aqueous layer is acidified with 30 ml of concentrated hydrochloric acid. The oily precipitate is extracted into 100 ml of ether. The ether extract is dried (MgSO$_4$) and concentrated to give 3.99 g of a solid, m.p. 91°–94° C.

A portion (2.14 g, 0.0058 mole) of the above solid, 0.80 g (0.0058 mole) of potassium carbonate, 0.99 g (0.007 mole) of methyl iodide, and 60 ml of DMF is stirred for 72 hours and poured into 200 ml of water. The oily precipitate is extracted twice with 100 ml of ether. The combined ether extracts were dried over magnesium sulfate and concentrated. The residue is kugelrohr distilled to give 1.21 g (55.3%) of the desired product as an oil, $n_D^{25}$ 1.4556.

Anal. Calc'd. for C$_{16}$H$_{14}$F$_5$NO$_4$: C, 50.67; H, 3.72; N, 3.67; Found: C, 50.57; H, 3.73; N, 3.67.

In a manner similar to Examples 28, 29, and 30, other 2-(difluoromethyl)-6-(trifluoromethyl)-3,5-pyridinedicarboxylic acid 5-monoester of this invention are prepared.

Having due regard for starting materials substituted and the reaction condition suitable for the reactant employed, additional examples are provided as noted in Table 18.

TABLE 18

| Ex. No. | Starting Material | Solvent-Condition | Product | Empirical Formula | m.p. °C. | Analysis % Element | Calc'd | Found |
|---|---|---|---|---|---|---|---|---|
| 118 | Ex. 112 | ethanol-water; room temperature | 2-(difluoromethyl)-4-isopropyl-6-(trifluoro-methyl)-3,5-pyridine-dicarboxylic acid 5-propargyl ester | C$_{15}$H$_{12}$F$_5$NO$_4$ | 89–92 | C<br>H<br>N | 49.32<br>3.31<br>3.83 | 49.03<br>3.35<br>3.79 |
| 119 | Ex. 27 | ethanol-water; room temperature | 2-(difluoromethyl)-4-(2,2-dimethylpropyl)-6-(trifluoromethyl)-3,5-pyridinedicarboxylic acid 5-ethyl ester | C$_{16}$H$_{18}$F$_5$NO$_4$ | 110–111.5 | C<br>H<br>N | 50.13<br>4.73<br>3.65 | 50.04<br>4.78<br>3.60 |
| 120 | Ex. 26 | ethanol-water; room temperature | 2-(difluoromethyl)-4-(1-methylpropyl)-6-(trifluoromethyl)-3,5-pyridinedicarboxylic acid 5-ethyl ester | C$_{15}$H$_{16}$F$_5$NO$_4$ | 83.5–85.5 | C<br>H<br>N | 48.79<br>4.37<br>3.79 | 48.86<br>4.38<br>3.77 |
| 121 | Ex. 72 | ethanol-water; room temperature | 2-(difluoromethyl)-4-isopropyl-6-(tri-fluoromethyl)-3,5-pyridinedicarboxylic acid 5-methyl ester | C$_{13}$H$_{12}$F$_5$NO$_4$ | 114–116 | C<br>H<br>N | 45.76<br>3.54<br>4.10 | 45.86<br>3.57<br>4.10 |

In a manner similar to the procedure of Example 69, other pyridinedicarboxylates of this invention are prepared from the appropriate monoacids. Having due regard for starting material substituted and reaction condition suitable for the reactants employed, additional examples are provided as noted in Table 19.

TABLE 19

| Ex. No. | Starting Material | Reactant | Solvent-Condition | Product | Empirical Formula | $n_D^{25}$ | Analysis % Element | Calc'd | Found |
|---|---|---|---|---|---|---|---|---|---|
| 122 | Ex. 77 | K$_2$CO$_3$—HC≡CCH$_2$Br | DMF, room temperature | 5-methyl 3-propargyl 2-(difluoromethyl)-4-n-propyl-6-(trifluoromethyl)-3,5-pyridinedi-carboxylate | C$_{16}$H$_{14}$F$_5$NO$_4$ | 1.4582 | C<br>H<br>N | 50.67<br>3.72<br>3.69 | 50.54<br>3.79<br>3.61 |
| 123 | Ex. 120 | K$_2$CO$_3$—CH$_3$I | DMF; room temperature | 3-ethyl 5-methyl 6-(difluoromethyl)-4-(1-methylpropyl)-2-(trifluoromethyl)- | C$_{16}$H$_{18}$F$_5$N$_1$O$_4$ | 1.4500 | C<br>H<br>N | 50.19<br>4.73<br>3.65 | 49.90<br>4.78<br>3.59 |

TABLE 19-continued

| Ex. No. | Starting Material | Reactant | Solvent-Condition | Product | Empirical Formula | $n_D^{25}$ | Element | Analysis % Calc'd | Found |
|---|---|---|---|---|---|---|---|---|---|
| 124 | Ex. 119 | K₂CO₃—CH₃I | DMF; room temperature | 3,5-pyridinedicarboxylate 3-ethyl 5-methyl 6-(difluoromethyl)-4-(2,2-dimethylpropyl)-2-(trifluoromethyl)-3,5-pyridinedicarboxylate | $C_{17}H_{20}F_5NO_4$ | 1.4538 | C H N | 51.39 5.07 3.53 | 51.34 5.07 3.53 |
| 125 | Ex. 118 | K₂CO₃—CH₃I | DMF; room temperature | 3-methyl 5-propargyl 2-(difluoromethyl)-4-isopropyl-6-(trifluoromethyl)-3,5-pyridinedicarboxylate | $C_{16}H_{14}F_5NO_4$ | 1.4589 | C H N | 50.67 3.72 3.69 | 50.47 3.78 3.65 |

EXAMPLE 126

Preparation of diethyl 2-(difluoromethyl)-4-(4-pyridyl)-6-(trifluoromethyl)-3,5-pyridinedicarboxylate In a manner similar to the procedure of Example 13, product of Example ss of Table 3 is reacted with 1,8-diaza-bicyclo-[5.4.0]-undec-5-ene to give the desired product as a solid, m.p. 43°–45° C.

Anal. Calc'd. for $C_{18}H_{15}F_5N_2O_4$: C, 51.68; H, 3.61; N, 6.70; Found: C, 51.51; H, 3.63; N, 6.66.

EXAMPLE 127

Preparation of 3-ethyl 5-methyl 6-(difluoromethyl)-4-(2-oxiranyl)-2-(trifluoromethyl)-3,5-pyridinedicarboxylate A stirred mixture of 14.0 g (0.039 mole) of product of Example 99, 105 ml of ethanol, 70 ml (0.60 mole) of 30% hydrogen peroxide, and 2.9 g (0.033 mole) of sodium bicarbonate is heated at 70° C. for 3 hours. The reaction mixture is cooled and concentrated in vacuo to approximately 30 ml then extracted with 75 ml of methylene chloride. The methylene chloride solution is washed with 300 ml of water. The aqueous layer is extracted twice with 75 ml of methylene chloride. The combined methylene chloride extracts were dried over magnesium sulfate and concentrated. The residue is purified by HPLC using 8% ethyl acetate/cyclohexane as eluent to give a yellow solid which after recrystallization from hexane/ether gave 2.32 g of the desired product as a white solid; m.p. 57.5°–59° C.

Anal. Calc'd. for $C_{14}H_{12}F_5NO_5$: C, 45.54; H. 3.28; N, 3.79; Found: C, 45.63; H, 3.28; N, 3.77.

EXAMPLE 128

Preparation of 3-ethyl 5-methyl 4-(1,2-dibromoethyl)-6-(difluoromethyl)-2-(trifluoromethyl)-3,5-pyridinedicarboxylate A solution of 3.0 g (0.084 mole) of product of Example 99, 1.49 g (0.091 mole) of bromine in 30 ml of carbon tetrachloride is stirred for 3 days and concentrated. The residue is kugelrohr distilled at 0.1 torr (pot temperature, 140°–150° C.) to give 3.45 g (80%) of the desired product as an oil, $n_D^{25}$ 1.4950.

Anal. Calc'd. for $C_{14}H_{12}Br_2F_5NO_4$: C, 32.77; H, 2.36; N, 2.73; Found: C, 33.00; H, 2.39; N, 2.93.

EXAMPLE 129

Preparation of 3-ethyl 5-methyl 4-(1-bromoethenyl)-6-(difluoromethyl)-2-(trifluoromethyl)-3,5-pyridinedicarboxylate To a stirred mixture of 0.49 g (0.012 mole) of 60% sodium hydride in oil dispersion and 4 ml of anhydrous THF is added 10 ml of methanol under nitrogen. The reaction mixture is cooled with an ice bath to 5° C. then treated slowly with a solution of 3.0 g (0.0058 mole) of product of Example 128 in 2 ml of anhydrous THF, while the reaction mixture is maintained below 15° C. The mixture is stirred at 0° C. for 2 hours and poured into 180 ml of 1% hydrochloric acid then extracted three times with 50 ml of methylene chloride. The combined methylene chloride extracts are dried over magnesium sulfate and concentrated. The residue is purified by a radially-accelerated preparatory TLC using 10% ethyl acetate/cyclohexane as eluent to give 0.85 g (33%) of the desired product as a light yellow oil, $n_D^{25}$ 1.4734.

Anal. Calc'd. for $C_{14}H_{11}BrF_5NO_4$: C, 38.91; H, 2.57; N, 3.29; Found: C, 39.00; H, 2.64; N, 3.37.

EXAMPLE 130

Preparation of 3-ethyl 5-methyl 6-(difluoromethyl)-4-methylsulfonylmethyl-2-(trifluoromethyl)-3,5-pyridinedicarboxylate To a cold (15° C.) stirred solution of 0.5 g (0.0012 mole) of product of Example 101 in 20 ml of methylene chloride is added 0.55 g of m-chloroperbenzoic acid in portion. The reaction mixture is stirred at ambient temperature for 16 hours, poured into 150 ml of 1% aqueous sodium hydroxide. The methylene chloride layer is separated, washed with 100 ml of water, dried over magnesium sulfate, and concentrated in vacuo to give a white solid. Recrystallization from ether/hexane gives 0.46 g of the desired product as a white solid, m.p. 110.5°–11.5° C.

Anal. Calc'd. for $C_{14}H_{14}F_5NO_6S$: C, 40.10; H, 3.37; N, 3.34; Found: C, 39.97; H, 3.37; N, 3.33.

EXAMPLE 131

Preparation of dimethyl 2-(difluoromethyl)-4-methylthiomethyl-6-(trifluoromethyl)-3,5-pyridinedicarboxylate A mixture of 25.0 g (0.062 mole) of product of Example 25, 100 ml of 10% aqueous sodium hydroxide, 40 ml of ethanol, and 150 ml of water is held at reflux for 48 hours and concentrated to approximate 150 ml. The residual solution is diluted with 1 L of water and acidified to pH 1-2 with concentrated hydrochloride acid. The aqueous mixture is extracted three times with 300 ml of ether. The combined ether extracts are dried over magnesium sulfate and concentrated to give 11.7 g (55%) of a solid, m.p. 209°-210° C.

A mixture of 7.08 g (0.0226 mole) of above solids, 3.0 ml (0.0475 mole) of methyl iodide, 3.45 g (0.025 mole) of potassium carbonate, and 35 ml of DMF is stirred for 16 hours. The reaction mixture is poured into 300 ml of 1% hydrochloride acid and extracted with 100 ml of methylene chloride. The methylene chloride solution is washed successively with 200 ml of water and 200 ml of 1% sodium bicarbonate, dried over magnesium sulfate, and concentrated. The residue is kugelrohr distilled at 0.15 torr (pot temperature, 120°-125° C.) to give a white solid which is recrystallized from ether/hexane to give 3.0 g (36%) of the desired product, m.p. 50.5°-51.5° C.

Anal. Calc'd. for $C_{13}H_{12}F_5NO_4S$: C, 41.83; H, 3.24; N, 3.75; Found: C, 41.84; H, 3.25; N, 3.75.

EXAMPLE 132

Preparation of dimethyl 2-(difluoromethyl)4-iodomethyl-6-(trifluoromethyl)-3,5-pyridinedicarboxylate A mixture of 10.43 g (0.033 mole) of the solid (m.p. 209°-210° C.) described in Example 131, 8.2 ml (0.132 mole) of methyl iodide, 20.2 g (0.146 mole) of potassium carbonate, and 45 ml of DMF is stirred at ambient temperature for 5 days. The reaction mixture is poured into 550 ml of 1% aqueous hydrochloric acid and extracted three times with 100 ml of methylene chloride. The combined extracts are washed successively with 1% hydrochloride acid, 1% sodium bicarbonate, and 10% sodium chloride, dried over magnesium sulfate, and concentrated. The residual is purified by HPLC using 15% ethyl acetate/cyclohexane as eluent to give a yellow oil which crystallizes after standing. Recrystallization twice from ether/hexane gives 2.27 g (15%) of the desired product as a white solid, m.p. 78°-79° C.

Anal. Calc'd. for $C_{12}H_9F_5INO_4$: C, 31.81; H, 2.00; N, 3.09; Found: C, 31.95; H, 1.90; N, 3.07.

EXAMPLE 133

Preparation of 3-ethyl 5-methyl 2-(difluoromethyl)-4-methylthiomethyl-6-(trifluoromethyl)-3,5-pyridinecarboxylate A mixture of 2.8 g (0.0077 mole) of product of Example 131, 3.7 g (0.0092 mole) of 10% sodium hydroxide, 3 ml of water, and 20 ml of ethanol is stirred at ambient temperature for 5½ hours, and concentrated. The residue is dissolved in 150 ml of water and extracted twice with 50 ml of methylene chloride. The aqueous layer is acidified to pH 1-2 with concentrated hydrochloride acid and extracted three times with methylene chloride. The combined methylene chloride extracts are dried over magnesium sulfate and concentrated to give 2.6 g of a solid.

A mixture of 2.47 g (0.0066 mole) of the above solid, 1.28 g (0.0082 mole) of ethyl iodide, 0.71 g (0.051 mole) of potassium carbonate, and 20 ml of DMF is stirred for 48 hours and poured into 200 ml of 1% hydrochloride acid. The mixture is extracted three times with 50 ml of methylene chloride. The combined methylene chloride extracts are washed successively with 150 ml of 1% sodium chloride and 150 ml of 1% sodium bicarbonate, dried over magnesium sulfate, and concentrated. The residue is kugelrohr distilled at 0.3 torr. The distillate (collected at pot temperature of 120°-130° C.) is further purified by radially-accelerated preparatory TLC using 10% ethylene acetate/cyclohexane to give an oil. Kugelrohr distillation of this oil at 0.15 torr (collected at pot temperature of 125°-130° C.) gives the desired product as a light yellow oil, $n_D^{25}$ 1.4750.

Anal. Calc'd. for $C_{14}H_{14}F_5NO_4S$: C, 43.41; H, 3.64; N, 3.62; Found: C, 43.42; H, 3.65; N, 3.62.

EXAMPLE 134

Preparation of 3-ethyl 5-methyl 6-(difluoromethyl)-4-methyl-2-(trifluoromethyl)-3,5-pyridinedicarboxylate This product is isolated as a by-product in the preparation of the product of Example 101. The crude material is purified by HPLC as noted in Example 101. After removal of the product of Example 101, the later fraction gives 1.42 g of a yellow oil which is kugelrohr distilled at 0.5 torr (pot temperature of 125°-135° C.) to give 1.35 g of the desired product, $n_D^{25}$ 1.4483.

Anal. Calc'd. for $C_{13}H_{12}F_5NO_4$: C, 45.76; H, 3.54; N, 4.10; Found: C, 45.76; H, 3.52; N, 4.08.

EXAMPLE 135

Preparation of [3-carbomethoxy-5-carbethoxy-2-(difluoromethyl)-6-(trifluoromethyl)]-4-pyridylmethyl-dimethylsulfonium tetrafluoroborate To a solution of 19.9 g (0.0513 mole) of product of Example 101 in 150 ml of acetonitrile under nitrogen is added 10.0 g (0.051 mole) of silver tetrafluoroborate followed immediately by 4.6 ml (0.075 mole) of methyl iodide. The reaction mixture is stirred at ambient temperature for 16 hours, then maintained at 45° for 24 hours. The grayish precipitate is filtered. The filtrate is concentrated to a light brown oil which crystallizes upon standing. Recrystallization from ether-tetrahydrofuran gives 21.6 g (86% yield) of the desired product as a white solid, mp 119.5°-121°. Anal. Calc'd. for $C_{15}H_{17}BF_9NO_4S$: C, 36.83; H, 3.50; N, 2.86; Found: C, 36.86; H, 3.46; N, 2.76.

EXAMPLE 136

Preparation of 5-ethyl-3-methyl 2-(difluoromethyl)-4-(N,N-dimethylaminomethyl)-6-(trifluoromethyl)-3,5-pyridinedicarboxylate To a stirred solution of 3.0 g (0.0061 mole) of product of example 135 in 15 ml of N,N-dimethylformamide under nitrogen is added 1.4 g (0.0093 mole) of sodium iodide. The reaction mixture is stirred at 25° for ½ hour, then treated with 2.3 g (0.0091 mole) of an 18% solution of dimethylamine in ether. After stirring at ambient temperature for ½ hour, the reaction mixture is poured into a mixture of 500 ml of water and 100 ml of saturated sodium chloride solution. The organic is extracted into ether (4×75 ml). The ether extracts are combined and washed with 200 ml of 10% sodium chloride solution, dried over magnesium sulfate and concentrated. The residue is purified by HPLC using 5% ethyl acetate in cyclohexane as eluent. The desired fraction is concentrated. The residue is kugelrohr distilled at 0.1 torr (pot temperature 120°-130°) to give 1.98 g (84% yield) of a water white oil, $n_D^{25}$ 1.4518. Anal. Calc'd. for $C_{15}H_{17}F_5N_2O_4$: C, 46.88; H, 4.46; N, 7.29; Found: C, 46.70; H, 4.45; N, 7.23.

EXAMPLE 137

Preparation of 5-ethyl-3-methyl 2-(difluoromethyl-4-(N-ethyl-N-methylaminomethyl)-6-(trifluoromethyl)-3,5-pyridinedicarboxylate To a stirred solution of 4.0 g (0.0081 mole) of product of Example 135 in 25 ml of N,N-dimethylformamide cooled to 5° with an ice bath is added 1.84 g (0.012 mole) of sodium iodide. The reaction mixture is stirred at 0°-5° for 1 hour, then allowed to warm to ambient temperature. N-ethyl-N-methylamine (1.05 g, 0.017 mole) is added to the reaction mixture and the reaction mixture is stirred for 2 hours at ambient temperature, then poured into a mixture of 300 ml of water and 100 ml of saturated sodium chloride solution. The organic is extracted into ether (4×100 ml) and the combined ether extracts are washed with 200 ml of 10% sodium chloride solution, dried over magnesium sulfate and concentrated. The residual oil is purified by radially-accelerated preparatory TLC followed by kugelrohr distillation at 0.15 torr (pot temperature 120°-130°) to give 2.49 g (77% yield) of the desired product as a yellow oil, $n_D^{25}$ 1.4534.

Anal. Calc'd. for $C_{16}H_{19}F_5N_2O_4$: C, 48.24; H, 4.81; N, 7.03; Found: C, 48.10; H, 4.83; N, 6.99.

Compounds of this invention may be prepared from corresponding compounds in which the $R_1$ or $R_2$ group contains one more fluorine atom than does the product compound. This scheme, which has been discussed earlier, involves one or more additional sequences of sodium borohydride reduction to the correspondong 1,2-dihydropyridine followed by dehydrofluorination in the presence of a nonaqueous organic base such as DBU or 2,6-lutidine. This reaction pattern may be shown schematically as follows:

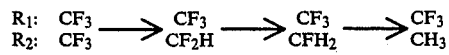

or

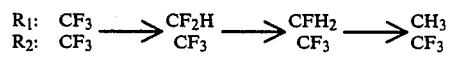

However, this process is not restricted to the situation in which one of $R_1$ and $R_2$ is $CF_3$. The reaction applies equally, for example, when $R_2$ is $CF_2H$, $CFH_2$, or alkyl and $R_1$ is to be dehydrofluorinated. The following Examples 138 and 139 show the pre-paration of compounds of this invention in which one of $R_1$ and $R_2$ is $CF_3$ and the other is selected from $CFH_2$ and $CH_3$.

EXAMPLE 138

Preparation of dimethyl 2-(fluoromethyl)-4-isobutyl-6-(trifluoromethyl)-3,5-pyridinedicarboxylate To a solution of 50.3 g (0.136 mole) of product of example 14 in 200 ml of DMF is added 21.3 g (0.563 mole) of sodium borohydride. The reaction mixture becomes exothermic and the temperature of the reaction mixture rises to 65° C. and subsides to 40° C. after 40 min. of stirring. To the reaction mixture is added 15 ml of water. The exothermic reaction mixture is cooled by an ice-water bath to 40° C. The cooling bath is removed and the reaction mixture is stirred for 20 min. before being poured into 1 L of water. The organic is extracted into 500 ml of methylene chloride. The methylene chloride extract is dried over magnesium sulfate and concentrated. The residual oil (44.5 g) is purified by HPLC using 5% ethyl acetate in cyclohexane as eluent. The first 2.8 L of eluate gives 7.6 g of an oil which contains 56% of the desired product, 22% of the starting material, and 22% of an unidentified material. The second 2.5 L of eluate gives 24.6 g of an oil which contains a mixture of dimethyl 2-(difluoromethyl)-1,2-dihydro-4-isobutyl-6-(trifluoromethyl)-3,5-pyridinedicarboxylate (E) and dimethyl 6-(difluoromethyl)-1,2-dihydro-4-isobutyl-2-(trifluoromethyl)-3,5-pyridinedicarboxylate (F) and other unidentified products. This oil is crystallized from ether-hexane to give 7.4 g (15%) of a solid, mp 82°-85° C., which is a 4.6:1 mixture of above mentioned (E) and (F). The mother liquor is concentrated to an oil (15.6 g) which contains (E), (F), and other unidentified products. A solution of above oil, 9.0 g (0.0568 mole) of DBU and 100 ml of ether is stirred for 18 hours and washed with 100 ml of 3N hydrochloric acid. The ether solution is dried over magnesium sulfate and concentrated. The residual oil (14.5 g) is purified by HPLC using 5% ethyl acetate in cyclohexane as eluent. The first 2.0 L of eluate gives 8.8 g (19%) of the desired product as an oil, $n^{25}D$ 1.4567. Anal. Calc'd. for $C_{15}H_{17}F_4NO_4$: C, 51.28; H, 4.88; N, 3.99; Found: C, 51.39; H, 4.76; N, 385.

EXAMPLE 139

Preparation of dimethyl 4-isobutyl-2-methyl-6-(trifluoromethyl)-3,5-pyridinedicarboxylate To a solution of 8.8 g (0.025 mole) of product of Example 138 in 100 ml of DMF is added 6.0 g (0.16 mole) of sodium borohydride. After 10 min. stirring, the reaction mixture is heated to 65° in 20 min. and maintained at 65° C. for 1½ hours before being poured into 500 ml of water. The organic is extracted into 500 ml of methylene chloride. The methylene chloride extract is dried over magnesium sulfate and concentrated to give 9.9 g of an oil which is purified by HPLC using 10% ethyl acetate in cyclohexane as eluent. The first 2.1 L of eluate gives an oil which is not further identified. The second 1.5 L of eluate gives 2.9 g of an oil which is stirred with 2.0 g of DBU and 50 ml of ether for 4 hours. The ether solution is washed successively with 60 ml of 3N hydrochloric acid and 60 ml of water, dried over magnesium sulfate and concentrated. The residual 2.2 g of an oil is purified by radially accelerated preparatory TLC using 5% ethyl acetate in cyclohexane as eluent. The first fraction gives an oil (1.2 g) which is kugelrohr distilled at 1 torr (pot temperature 140°) to give 1.1 g (13% yield) of the desired product as an oil, $n^{25}D$ 1.4606.

Anal. Calc'd. for $C_{15}H_{18}F_3NO_4$: C, 54.05; H, 5.44; N, 4.20; Found: C, 54.06; H, 5.45; N, 4.20.

EXAMPLE 140

Ethyl 6-(difluoromethyl)-5-[[(1-methylethyl)thio]carbonyl]-4-isobutyl-2-(trifluoromethyl)-3-pyridinecarboxylate A one liter flask was charged with 32 g (0.08 m) of product of Example 16 and 150 ml of ethanol. In a separate flask was stirred 15.84 g (0.24 m) of potassium hydroxide (85%) and 75 ml of water. The aqueous solution was added to the organic layer and stirring proceeded for 48 hours at room temperature. The reaction mixture was concentrated, diluted with water, and extracted with ethyl ether. The aqueous layer was acidified with concentrated HCl, cooled, and extracted with ethyl ether. The product layer was dried over anhydrous $MgSO_4$ filtered, concentrated and dried under vacuum to yield 24.5 g (82.93%) of acid. The acid was stirred with 150–200 ml of thionyl chloride and heated at reflux for 24 hours. The reaction mixture was concentrated to yield the acid chloride in 84.97% yield.

A 250 ml round bottom flask was charged with 6.25 g (0.016 m) of the acid chloride, 1.52 g (0.02 m) of propanethiol and 75–100 ml of tetrahydrofuran. To the magentically stirred mixture was added 2.44 g (0.02 m) of potassium tert-butoxide. The reaction mixture began to evolve heat and was stirred for 30 minutes. The mixture was then poured into ice water and extracted with methylene chloride. The organics were dried over anhydrous magnesium sulfate, filtered, and concentrated. The crude product was kugelrohr distilled to yield 1.95 g (28.55%). $n_D^{25} = 1.4704$.

Anal. Calc'd. for $C_{18}H_{22}F_5N_1O_3S_1$: C, 50.58; H, 5.19; Found: C, 50.73; H, 5.22; N, 3.24; S, 7.42

EXAMPLE 141

S,S-diethyl 2-difluoromethyl)-4-isobutyl-6-(trifluoromethyl)-3,5-pyridinedicarbothioate A one liter flask was charged with 70.91 g (0.1784 mole) of product of Example 16 and 300 ml of methanol. In a separate flask was combined 93.73 g (1.42 mole) of 85% potassium hydroxide and 150 ml of water. The aqueous and organic layers were combined and allowed to reflux for 48 hours. The reaction mixture was concentrated, diluted with water and extracted with ethyl ether. The ether layer was discarded. The aqueous layer was acidified with concentrated HCl and the oil precipitate was extracted with ether. The extract was dried over anhydrous magnesium sulfate, filtered, and concentrated to yield a viscous liquid (which later crystallized) in the amount of 53.7 g (88.22%). To this acid was added 250–300 ml of thionyl chloride. The reaction mixture was refluxed for 24 hours and was concentrated to yield 51.7 g (86.93%) of acid chloride.

A 250 ml flask was charged with 5.66 g (0.0149 mole) of the acid chloride, 75–100 ml of anhydrous tetrahydrofuran, and 5.57 g (0.0898 mol) of ethanethiol. To the magnetically stirred mixture was added 3.34 g (0.0298 mole) of potassium tert-butoxide. The mixture evolved heat and was stirred for 45 minutes. The reaction mixture was poured into ice water and stirred. The organics were extracted two times with methylene chloride, washed with ice water dried over anhydrous magnesium sulfate, concentrated and kugelrohr distilled. The mixture was chromatographed using 3% ethyl acetate in cyclohexane and concentrated to yield 1.1 g (17.21%) of oil, $n_D^{25} = 1.5256$.

Anal. Calc'd. for $C_{17}H_{20}F_5N_1O_2S_2$: C, 47.54; H, 4.69; N, 3.26; S, 14.93; Found: C, 47.40; H, 4.88; N, 3.21; S, 14.77.

Using procedures similar to those of Examples 140 and 141, other thioester and dithioester compounds were prepared. These compounds are shown in the following Table 20.

TABLE 20

| Example | Compound | $n_D^{25}$ | | Analysis Calc'd | Found |
|---|---|---|---|---|---|
| 142 | Ethyl 6-(difluoromethyl)-4-propyl 5-[(propylthio)carbonyl]-2-(trifluoromethyl)-3-pyridine-carboxylate | 1.4754 | C<br>H<br>N<br>S | 49.39<br>4.88<br>3.39<br>7.76 | 48.93<br>4.64<br>3.38<br>7.78 |
| 143 | Ethyl 6-(difluoromethyl)-5-[[(1-methylethyl)thio]carbonyl]-4-propyl-2-(trifluoromethyl)-3-pyridine-carboxylate | 1.4723 | C<br>H<br>N<br>S | 49.39<br>4.88<br>3.39<br>7.76 | 49.48<br>4.93<br>3.34<br>7.85 |
| 144 | Ethyl 6-(difluoromethyl)-5-[[(1,1-dimethylethyl)thio]carbonyl-]-4-propyl-2-(trifluoromethyl)-3-pyridinecarboxylate | 1.4718 | C<br>H<br>N | 50.58<br>5.19<br>3.28 | 50.43<br>5.21<br>3.23 |
| 145 | Methyl-6-(difluoromethyl)-5-[(ethylthio)carbonyl]-4-(2-methyl propyl)-2-(trifluoromethyl)-3-pyridinecarboxylate | 1.4788 | C<br>H<br>N<br>S | 48.12<br>4.54<br>3.51<br>8.03 | 48.39<br>4.77<br>3.32<br>7.73 |
| 146 | S,S—dimethyl 2-(difluoromethyl)-4-isobutyl-6-trifluoromethyl-3,5-pyridinedicarbothioate | 1.4788 | C<br>H<br>N<br>S | 44.88<br>4.02<br>3.49<br>15.98 | 45.44<br>4.10<br>3.47<br>15.99 |
| 147 | S,S—dimethyl 2,6-bis(trifluoromethyl)-4-isobutyl-3,5-pyridinedicarbothioate | m.p. 63–66° C. | C<br>H<br>N<br>S | 42.96<br>3.60<br>3.34<br>15.29 | 43.22<br>3.79<br>3.24<br>15.06 |
| 148 | S,S—dimethyl 2,6-bis(trifluoromethyl)-4-propyl-3,5-pyridine-dicarbothioate | m.p. 96–98° C. | C<br>H<br>N<br>S | 41.48<br>3.23<br>3.46<br>15.82 | 41.30<br>3.23<br>3.46<br>15.88 |
| 149 | S,S—diethyl 2,6-bis(trifluoromethyl)-4-propyl-3,5-pyridine-dicarbothioate | m.p. 66–69° C. | C<br>H<br>N<br>S | 44.34<br>3.95<br>3.23<br>14.79 | 44.29<br>3.99<br>3.22<br>14.87 |

EXAMPLE 150

3-Ethyl 5-methyl 4-methyl-2-isobutyl-6-(trifluoromethyl)-3,5-pyridinedicarboxylate An amount of 52.7 g of ethyl 3-amino-4-methyl-2-pentenoate was prepared from 98 g ethyl(2-methylpriopionyl)acetate using the procedure of Aberhart and Liv, JOC 1981, 3749. The enamino ester had $n_D^{25} = 1.4914$, bp 92°/6 mm. The above enamine (20 g) was mixed in 100 ml THF with 21.6 g methyl 2,2,2-trifluoroacetoacetate and 6 g of acetaldehyde. Upon adding a couple of drops of piperidine, a spontaneous isotherm to 60° was observed. The mixture was then heated with stirring at about 70° (just below reflux) for 1½ hours. While monitoring with $^{19}F$ nmr, the mixture was refluxed for 5 hours, then allowed to stand at room temperature overnight. The mixture was stripped of THF to give 46.1 g yield of crude product, 40 g of which was dehydrated using 25 ml trifluoroacetic anhydride and about 100 ml $CH_2Cl_2$. An exotherm to 40° was observed, and the material was refluxed for about one hour, then stripped to give crude product which was kugelrohr distilled (110°–160°/0.15 mm).

4.5 g of this crude intermediate (0.013 mole) was placed in $CH_2Cl_2$ and 3.4 g of 2,3-dichloro-5,6-dicyanobenzoquinone (DDQ) was added. The reaction was exothermic. The mixture was stirred for 3 hours at room temperature. GLC showed one main peak at the same retention time as starting material. The product was washed with $NaOH/NaHSO_3$ to reduce excess DDQ. The material was stripped of solvent, then kugelrohr distilled to give 3.5 g of crude product, which was further purified by HPLC with 3% ethyl acetate, 97% cyclohexane to give a purified fraction which was then kugelrohr distilled (bp 140°–150° at 0.15 mm) to give the desired product: $n_D^{25}$ 1.4557, 1 g yield.

Anal. Calc'd. for $C_{18}H_{24}F_3NO_4$: C, 54.05; H, 5.44; N, 4.20; Found: C, 53.98; H, 5.48; N, 4.20.

EXAMPLE 151

3-Ethyl 5-methyl 2-ethyl-4-isobutyl-6-(trifluoromethyl)-3,5-pyridinedicarboxylate A stirred mixture of 18.0 g (0.20 mole) isovaleraldehyde, 30.8 g (0.20 mole) methyl trifluoroacetoacetate, 28.6 g (0.20 mole) ethyl 3-amino-2-penteneoate, 60 ml tetrahydrofuran and 3 drops piperidine is heated and held at reflux for 18 hours. The cooled reaction mixture is concentrated and the residue partially crystalllizes on standing at ambient temperature. The solids are filtered from an 8.0 g sample, washed with hexane and recrystallized from tetrahydrofuran/hexane to give 1.72 g (22%) white solid, mp 148°–150° C.

A stirred mixture of 72 g (0.18 mole) crude solid prepared as above, 30 ml (0.21 mole) trifluoroacetic anhydride and 150 ml methylene chloride is heated and held at reflux for 2 hours. The washed reaction mixture is concentrated to give 88.0 g oil. To a stirred solution of 43 g (0.09 mole) oil in 200 ml methylene chloride cooled with a water bath is added in portions 17.5 g (0.077 mole) 2,3-dichloro-5,6-dicyano-1,4-benzoquinone. The reaction mixture is stirred for 1 hour and filtered. The filtrate is washed twice with 200 ml of 20% sodium hydroxide solution. Then with 200 ml 1% hydrochloric acid, dried over magnesium sulfate, filtered and concentrated to give 28.2 g oil. Purification by silica gel HPLC of a 10 g sample affords after kugelrohr distillation 3.07 g (26%) of light yellow oil, bp 105°–110° C./1 mm, $n_D^{25}$ 1.4582.

Anal. Calc'd. for $C_{17}H_{22}NF_3O_4$: C, 56.50; H, 6.14; N, 3.88; Found: C, 56.51; H, 6.17; N, 3.84.

EXAMPLE 152

Methyl 2-(difluoromethyl)-4-isobutyl-6-(trifluoromethyl)-5-carbethoxy-3-pyridine-N-butylimidate A mixture of ethyl 3-butylcarbamyl-2-(difluoromethyl)-4-isobutyl-6-(trifluoromethyl)-5-pyridinecarboxylate prepared in the same manner as the product of Example 89 in thionyl chloride was refluxed overnight. The excess thionyl chloride was removed and the residual oil was kugelrohr distilled at 140° C./0.5 mm to give 4.7 g of light yellow liquid (91% yield); $n_D^{25}$ 1.4668.

To a flame dried 100 ml round bottom flask was placed 30 ml of absolute methanol. It was blanketed by an atmosphere of nitrogen. To this was added 0.63 g (0.0056 mole) of potassium t-butoxide and it was cooled to 0° C. To this was added a solution of yellow liquid prepared above (2.5 g, 0.0056 mole) in anhydrous ether (20 ml) all at once through a double tip needle. The mixture turned white and cloudy immediately. It was stirred at room temperature overnight. The solvent was removed and the residue was extracted with ether. The ether layer was washed with water, dried ($MgSO_4$) and concentrated to give 2.49 g of a light yellow oil. It was purified by chromatograph using 30% $CH_2Cl_2$ in benzene as eluant to give 1.8 g of a light yellow oil (72% yield); $n_D^{25}$ 1.4546.

Further compounds of the present invention were prepared using the various techniques set out in the preceding Examples, sometimes in conjunction with other preparative steps well-known in the art. These compounds are shown in the following Table A, along with certain of their physical properties, where available. In Table A the following abbreviations are used in setting out the various, functional groups substituted on the pyridine ring:

| | |
|---|---|
| Me | Methyl |
| Et | Ethyl |
| Pr | Propyl |
| S(Thiole) |  |
| Cycpr | cyclopropyl |
| 1-Aziridine |  |
| 1,3-Dithiolane |  |

TABLE A

| Ex. No. | R₁ | X | R | Y | R₂ | M.P. | $n_D^{25}$ |
|---|---|---|---|---|---|---|---|
| 153 | CF₃ | C(O)OCH₂CF₃ | Cycpr | C(O)OCH₂CF₃ | CHF₂ | 44–46 | |
| 154 | CF₃ | C(O)SPr | CH₂CHMe₂ | C(O)SPr | CHF₂ | | 1.4978 |
| 155 | CF₃ | C(O)OMe | CH₂CHMe₂ | C(O)O—NH(CH₃)₂ | CHF₂ | 148–150 | |
| 156 | CF₃ | C(O)OMe | CH=CH₂ | C(O)OMe | CHF₂ | b.p. 100–105/0.1 torr | |
| 157 | CF₃ | C(O)OEt | CH₂S(O)Me | C(O)OMe | CHF₂ | 75–76 | |
| 158 | CF₃ | C(O)OEt | CH₂SMe | C(O)OH | CHF₂ | 88–89 | |
| 159 | CF₃ | C(O)OEt | 2(Thiole) | C(O)OEt | CHF₂ | 38–40 | |
| 160 | CF₃ | C(O)OEt | 2(Thiole) | C(O)OH | CHF₂ | 129.5–131 | |
| 161 | CF₃ | C(O)OEt | 2(Thiole) | C(O)OMe | CHF₂ | | 1.4998 |
| 162 | CF₃ | C(O)OEt | CH₂SEt | C(O)OMe | CHF₂ | | 1.4749 |
| 163 | CF₃ | C(O)OEt | CHMeSMe | C(O)OMe | CHF₂ | | 1.4734 |
| 164 | CF₃ | C(O)OEt | 2(Thiole) | C(O)OEt | CH₃ | | 1.5078 |
| 165 | CF₃ | C(O)OEt | CH₃ | C(O)OMe | CH₃ | | 1.4591 |
| 166 | CF₃ | C(O)OEt | CH₂Cypor | C(O)OEt | CHF₂ | b.p. 125–130/0.5 mm | |
| 167 | CF₃ | C(O)OMe | CH₂CHMe₂ | C(O)NHMe | CHF₂ | 185–188 | |
| 168 | CF₃ | C(O)OEt | CH₂CHMe₂ | C(O)NHMe | CHF₂ | 108–110 | |
| 169 | CF₃ | C(O)OEt | CHEtSMe | C(O)OMe | CHF₂ | | 1.4731 |
| 170 | CF₃ | C(O)OEt | CMe₂SMe | C(O)OMe | CHF₂ | | 1.4848 |
| 171 | CF₃ | C(O)OEt | CH₂CHMe₂ | C(O)OEt | CH₃ | | 1.4582 |
| 172 | CF₃ | C(O)OEt | CH₂CHMe₂ | C(O)OMe | CH₃ | | 1.4595 |
| 173 | CF₃ | C(O)OMe | CH₂CHMe₂ | C(O)OEt | CH₃ | | 1.4590 |
| 174 | CF₃ | C(O)OEt | CHMeOMe | C(O)OMe | CHF₂ | | 1.4473 |
| 175 | CF₃ | C(O)OEt | CH₂CH₂CN | C(O)OMe | CHF₂ | 95–96.5 | |
| 176 | CF₃ | C(O)OEt | CH₂—1-Aziridine | C(O)OMe | CHF₂ | 73–74 | |
| 177 | CF₃ | C(O)OEt | CHMe₂ | C(O)OEt | CH₃ | | 1.4588 |
| 178 | CF₃ | C(O)OEt | CHMe₂ | C(O)OMe | CH₃ | | 1.4608 |
| 179 | CF₃ | C(O)OEt | CHMeEt | C(O)OEt | CH₃ | | 1.4586 |
| 180 | CF₃ | C(O)OEt | CHMeEt | C(O)OMe | CH₃ | | 1.4508 |
| 181 | CF₃ | C(O)OEt | CH=CHNMe₂ | C(O)OEt | CHF₂ | b.p. 160–180/0.10–0.15 torr | |
| 182 | CF₃ | C(O)OEt | CMe=CHNMe₂ | C(O)OEt | CHF₂ | b.p. 150/0.5 torr | |
| 183 | CF₃ | C(O)OMe | CH₂C(O)H | C(O)OMe | CHF₂ | 81–82 | |
| 184 | CF₃ | C(O)OMe | CH₂CH(OMe)₂ | C(O)OMe | CHF₂ | 44–45 | |
| 185 | CF₃ | C(O)OEt | CH₂C(O)H | C(O)OEt | CHF₂ | 53–55 | |
| 186 | CF₃ | C(O)OEt | CHMeC(O)OMe | C(O)OMe | CHF₂ | 56.5–58 | |
| 187 | CF₃ | C(O)OEt | CH₂C(O)OH | C(O)OH | CHF₂ | 176–177 | |
| 188 | CF₃ | C(O)OEt | CH₂Me | C(O)OEt | CH₃ | | 1.5020 |
| 189 | CF₃ | C(O)OMe | CH₂CHMe₂ | C(O)OCH₂Cypor | CHF₂ | | 1.4578 |
| 190 | CF₃ | C(O)OMe | CH₂Pr | C(O)OMe | CHF₂ | | 1.4458 |
| 191 | CF₃ | C(O)OEt | CH₂CHMe₂ | C(O)SPr | CHF₂ | | 1.472 |
| 192 | CF₃ | C(O)OEt | CH₂CHMe₂ | C(O)NHBu | CHF₂ | 69–71 | |
| 193 | CF₃ | C(O)OEt | CH₂CHMe₂ | C(O)OCH₂Cycpr | CHF₂ | | 1.4531 |
| 194 | CF₃ | C(O)OEt | CH₂CHMe₂ | C(O)SMe | CHF₂ | | 1.4759 |
| 195 | CF₃ | C(O)OEt | CHMe₂ | C(O)SMe | CHF₂ | | 1.4808 |
| 196 | CF₃ | C(O)OEt | CHMe₂ | C(O)SEt | CHF₂ | | 1.4783 |
| 197 | CF₃ | C(O)OEt | CH₂Cycpr | C(O)OH | CHF₂ | 96–100 | |
| 198 | CF₃ | C(O)OMe | CH₂Cycpr | C(O)OMe | CHF₂ | | 1.4625 |
| 199 | CF₃ | C(O)OEt | CH₂Cycpr | C(O)OMe | CHF₂ | | 1.4595 |
| 200 | CF₃ | C(O)OCH₂CN | CH₂CHMe₂ | C(O)OCH₂CN | CHF₂ | 88–90° C. | |
| 201 | CF₃ | C(O)OEt | CH₂CHMeCF₃ | C(O)OEt | CHF₂ | 30–32 | |
| 202 | CF₃ | C(O)OH | CH₂CHMeCF₃ | C(O)OH | CHF₂ | 205–207 | |
| 203 | CF₃ | C(O)OMe | CH₂CHMeCF₃ | C(O)OMe | CHF₂ | 68–70 | |
| 204 | CF₃ | C(O)OEt | CH₂CHMe₂ | C(NBu)Cl | CHF₂ | | 1.4668 |
| 205 | CF₃ | C(O)OEt | CH₂CHMe₂ | C(NBu)OMe | CHF₂ | | 1.4546 |
| 206 | CF₃ | CN | CH₂CHMe₂ | CN | CHF₂ | 39–41 | |
| 207 | CF₃ | C(O)SMe | CH₂Cycpr | C(O)SMe | CHF₂ | 80–83 | |
| 208 | CF₃ | C(O)OMe | CH₂Cycpr | C(O)SMe | CHF₂ | | 1.4925 |
| 209 | CF₃ | C(O)OMe | CHMeSMe | C(O)OMe | CHF₂ | 59–62 | |
| 210 | CF₃ | C(O)OMe | CMe₂SMe | C(O)OMe | CHF₂ | 56–59 | |
| 211 | CF₃ | C(O)OMe | CHMeSMe | C(O)OEt | CHF₂ | | 1.4730 |
| 212 | CF₃ | C(O)OMe | CMe₂SMe | C(O)OEt | CHF₂ | | 1.4847 |
| 213 | CF₃ | C(O)OMe | CH₂CHMe₂ | C(O)OMe | CF₃ | 80.5–82.5 | |
| 214 | CF₃ | C(O)OEt | CH₃ | C(O)OEt | CH₃ | | 1.4552 |
| 215 | CH₃ | C(O)OEt | CH₂CHMe₂ | C(O)OEt | CHF₂ | | 1.4745 |
| 216 | CHF₂ | C(O)OEt | CH₃ | C(O)OEt | CH₃ | | 1.4752 |
| 217 | CF₃ | C(O)OMe | CH₂CH=CHC(O)OEt (cis) | C(O)OMe | CHF₂ | | 1.4644 |
| 218 | CF₃ | C(O)OMe | CH₃ | C(O)OMe | CHF₂ | 37–40 | |
| 219 | CF₃ | C(O)OMe | CH₂C(O)NH₂ | C(O)OMe | CHF₂ | 160–163 | |
| 220 | CF₃ | C(O)OMe | CH₂C(O)OH | C(O)OMe | CHF₂ | 156–157 | |
| 221 | CF₃ | C(O)OMe | CH₂CN | C(O)OMe | CHF₂ | 137–139 | |
| 222 | CF₃ | C(O)OMe | CH₂-2-(1,3-di-thiolane) | C(O)OMe | CHF₂ | 103–106 | |
| 223 | CF₃ | C(O)OMe | CH₂C(O)NHCMe₂—CH₂OH | C(O)OMe | CHF₂ | 132–133 | |

TABLE A-continued

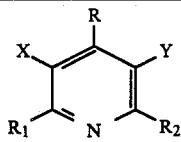

| Ex. No. | R₁ | X | R | Y | R₂ | M.P. | $n_D^{25}$ |
|---|---|---|---|---|---|---|---|
| 224 | CF₃ | C(O)OMe | CH₂C(O)NHCMe₂—CH₂Cl | C(O)OMe | CHF₂ | 136–137 | |
| 225 | CF₃ | C(O))Me | CH₂C(O)SCHMe₂ | C(O)OMe | CHF₂ | 69–70 | |
| 226 | CF₃ | C(O)OMe | CH₂C(O)OEt | C(O)OMe | CHF₂ | 81–82 | |
| 227 | CF₃ | C(O)OMe | CH₂C(O)NMe₂ | C(O)OMe | CHF₂ | 137–138.5 | |
| 228 | CF₃ | C(O)OMe | CH₂CHMe₂ | C(O)SMe | CHF₂ | 36–40 | |
| 229 | CF₃ | C(O)OMe | CH₂CHMe₂ | C(O)SCHMe₂ | CHF₂ | | 1.4752 |
| 230 | CF₃ | C(O)SMe | CH₂Pr | C(O)SMe | CHF₂ | 68–71 | |
| 231 | CF₃ | C(O)SMe | CHMe₂ | C(O)SMe | CHF₂ | 96–98 | |
| 232 | CF₃ | C(O)SEt | CHMe₂ | C(O)SEt | CHF₂ | 58–62 | |
| 233 | CF₃ | C(O)OMe | CH₂CHMe₂ | C(O)OCHMe₂ | CHF₂ | | 1.4467 |
| 234 | CF₃ | C(O)SEt | CH₂Pr | C(O)SEt | CHF₂ | 32–34 | 1.5420 |
| 235 | CF₃ | C(O)OMe | CH₂CHMe₂ | C(O)SPr | CHF₂ | | 1.4780 |
| 236 | CF₃ | C(O)SEt | CH₂CHMe₂ | C(O)SEt | CF₃ | 34–37 | |
| 237 | CF₃ | C(O)OMe | Cycpr | C(O)SMe | CHF₂ | 68–71 | |
| 238 | CF₃ | C(O)OMe | Cycpr | C(O)SEt | CHF₂ | 51–53 | |
| 239 | CH₂F | C(O)OMe | CH₂CHMe₂ | C(O)OMe | CH₃ | | 1.4909 |
| 240 | CH₂F | C(O)OMe | CH₂Me | C(O)OMe | CH₃ | | |
| 241 | CHF₂ | C(O)OMe | CH₂CHMe₂ | C(O)OMe | CH₃ | | 1.4795 |
| 242 | CF₃ | C(O)OEt | CF₃ | C(O)OEt | CHF₂ | | 1.4191 |
| 243 | CF₃ | C(O)OEt | CHF₂ | C(O)OEt | CF₃ | 50.5–52.5 | |
| 244 | CF₃ | C(O)OEt | CH₂SMe | C(O)OMe | CH₃ | | 1.4904 |
| 245 | CF₃ | C(O)OMe | CH₂SMe | C(O)OMe | CH₃ | | 1.4951 |
| 246 | CH₂F | C(O)OEt | CH₂CHMe₂ | C(O)OEt | CH₃ | | 1.4849 |

As noted above, the compounds of this invention have been found to be effective as herbicides, particularly as pre-emergent herbicides. Tables 20 and 21 summarize results of tests conducted to determine the pre-emergent herbicidal activity of the compounds of this invention.

The pre-emergent tests are conducted as follows:

A good grade of top soil is placed in aluminum pans and compacted to a depth of 0.95 to 1.27 cm. from the top of the pan. On the top of the soil is placed a predetermined number of seeds or vegetative propagules of various plant species. The soil required to level fill the pans after seeding or adding vegetative propagules is weighed into a pan. A known amount of the active ingredient applied in acetone as a solvent is thoroughly mixed with the soil, and the herbicide/soil mixture is used as a cover layer for prepared pans. In Table I below the amount of active ingredient is equal to the rate of 11.2 kg/ha. After treatment, the pans are moved into a greenhouse bench where they are watered from below as needed to give adequate moisture for germination and growth.

Approximately 10–14 days (usually 11 days) after treating, the plants are observed and the results recorded. In some instances an additional observation was made 24–28 days (usually 25 days) after treating, and these observations are denoted in the Tables by an asterisk (*) following the "Example" column. Table I below summarizes such results. The herbicidal rating is obtained by means of a fixed scale based on the percent of each plant species.

The ratings are defined as follows:

| % Inhibition | Rating |
|---|---|
| 0–24 | 0 |
| 24–49 | 1 |
| 50–74 | 2 |
| 75–100 | 3 |

The plant species utilized in one set of tests, the data for which are shown in Table 20, are identified by letter in accordance with the following legend:

A - Canada Thistle*
B - Cocklebur
C - Velvetleaf
D - Morning Glory
E - Lambsquarters
F - Smartweed
G - Yellow Nutsedge*
H - Quackgrass*
I - Johnsongrass*
J - Downy Brome
K - Barnyardgrass

*Grown from vegetative propagules

TABLE 21

| Example No. | kg/h | A | B | C | D | E | F | G | H | I | J | K |
|---|---|---|---|---|---|---|---|---|---|---|---|---|
| 6 | 11.2 | 3 | 1 | 3 | 3 | 3 | 3 | 0 | 3 | 1 | 3 | 3 |
| 6* | 11.2 | 3 | 0 | 3 | 3 | 3 | 3 | 0 | 3 | 1 | 3 | 3 |
| 7 | 11.2 | — | 2 | 2 | 3 | 3 | 2 | 0 | 3 | 0 | 3 | 3 |
| 94 | 11.2 | 1 | 0 | 2 | 2 | 3 | 3 | 1 | 3 | 0 | 3 | 3 |
| 95 | 11.2 | 1 | 0 | 2 | 3 | 3 | 2 | 0 | 3 | 0 | 3 | 3 |
| 12 | 11.2 | 3 | 2 | 3 | 3 | 3 | 3 | 3 | 3 | 3 | 3 | 3 |
| 38 | 11.2 | 0 | 0 | 0 | 0 | 0 | 0 | 0 | 0 | 0 | 0 | 0 |
| 32 | 11.2 | 3 | 1 | 3 | 3 | 3 | 3 | 3 | 3 | 3 | 3 | 3 |
| 37 | 11.2 | 3 | 0 | 3 | 3 | 3 | 3 | 1 | 3 | 0 | 3 | 3 |
| 13 | 11.2 | 3 | 1 | 3 | 3 | 3 | 3 | 3 | 3 | 3 | 3 | 3 |
| 39 | 11.2 | 0 | 0 | 0 | 0 | 0 | 0 | 0 | 0 | 0 | 0 | 0 |
| 28 | 11.2 | 0 | 0 | 0 | 0 | 0 | 0 | 0 | 0 | 0 | 0 | 0 |
| 96 | 11.2 | — | 0 | 0 | 1 | 3 | — | 0 | 0 | 0 | 3 | 3 |
| 19 | 11.2 | — | 0 | 0 | 0 | 0 | 0 | 0 | 0 | 0 | 0 | 1 |
| 8 | 11.2 | 0 | 0 | 0 | 0 | 1 | 1 | 0 | 0 | 0 | 0 | 0 |
| 46 | 11.2 | 0 | 0 | 0 | 0 | 3 | 0 | 0 | 0 | 0 | 0 | 3 |
| 61 | 11.2 | 3 | 1 | 3 | 3 | 3 | 3 | 1 | 3 | 1 | 3 | 3 |
| 45 | 11.2 | 0 | 0 | 0 | 0 | 0 | 0 | 0 | 0 | 0 | 0 | 0 |

TABLE 21-continued

| Example No. | kg/h | A | B | C | D | E | F | G | H | I | J | K |
|---|---|---|---|---|---|---|---|---|---|---|---|---|
| 88 | 11.2 | 0 | 0 | 0 | 0 | 0 | — | 0 | 0 | 0 | 0 | 0 |
| 92 | 11.2 | 3 | 0 | 1 | 3 | 2 | — | 0 | 3 | 3 | 3 | 3 |
| 89 | 11.2 | 0 | 0 | 0 | 0 | 3 | — | 0 | 0 | 0 | 0 | 3 |
| 27 | 11.2 | — | 0 | 1 | 3 | 3 | — | 0 | 3 | 3 | 3 | 3 |
| 59 | 11.2 | — | 1 | 3 | 3 | 3 | — | 3 | 3 | 3 | 3 | 3 |
| 59* | 11.2 | — | 1 | 3 | 3 | 3 | — | 3 | 3 | 3 | 3 | 3 |
| 60 | 11.2 | — | 0 | 0 | 1 | 3 | — | 0 | 1 | 1 | 3 | 3 |
| 91 | 11.2 | — | 0 | 0 | 0 | 0 | — | 0 | 0 | 0 | 0 | 1 |
| 52 | 11.2 | — | 3 | 3 | 3 | 3 | — | 3 | 3 | 3 | 3 | 3 |
| 52* | 11.2 | — | 3 | 3 | 3 | 3 | — | 3 | 3 | 3 | 3 | 3 |
| 58 | 11.2 | — | 0 | 0 | 0 | 0 | 0 | 0 | 0 | 0 | 1 | 1 |
| 62 | 11.2 | — | 0 | 2 | 3 | 3 | 3 | 0 | 2 | 0 | 3 | 3 |
| 90 | 11.2 | — | 0 | 1 | 2 | 1 | 1 | 0 | 0 | 0 | 3 | 3 |
| 18 | 11.2 | — | 1 | 3 | 3 | 3 | 3 | 2 | 3 | 3 | 3 | 3 |
| 40 | 11.2 | — | 0 | 0 | 0 | 0 | 0 | 0 | 0 | 0 | 0 | 0 |
| 29 | 11.2 | — | 0 | 0 | 1 | 1 | 1 | 0 | 3 | 0 | 2 | 3 |
| 47 | 11.2 | — | 0 | 1 | 2 | 3 | 2 | 0 | 0 | 0 | 2 | 3 |
| 48 | 11.2 | — | 0 | 0 | 0 | 0 | 0 | 0 | 0 | 0 | 0 | 0 |
| 46 | 11.2 | — | 0 | 2 | 3 | 3 | 3 | 0 | 3 | 3 | 3 | 3 |
| 15 | 11.2 | 3 | 2 | 3 | 3 | 3 | 3 | 3 | 3 | 3 | 3 | 3 |
| 44 | 11.2 | 3 | 0 | 2 | 3 | 3 | 3 | 0 | 1 | 0 | 3 | 3 |
| 31 | 11.2 | 3 | 1 | 2 | 3 | 3 | 3 | 0 | 0 | 0 | 3 | 3 |
| 53 | 11.2 | 3 | 2 | 3 | 3 | 3 | 3 | 3 | 3 | 3 | 3 | 3 |
| 16 | 11.2 | 3 | 2 | 3 | 3 | 3 | 3 | 2 | 3 | 3 | 3 | 3 |
| 21 | 11.2 | 1 | 0 | 0 | 2 | 3 | 3 | 0 | 0 | 3 | 3 | 3 |
| 64 | 11.2 | 3 | 0 | 3 | 3 | 3 | 3 | 1 | 3 | 2 | 3 | 3 |
| 32 | 11.2 | 0 | 0 | 0 | 0 | 0 | 0 | 0 | 0 | 0 | 0 | 1 |
| 54 | 11.2 | 3 | 3 | 3 | 3 | 3 | 3 | 3 | 3 | 3 | 3 | 3 |
| 54* | 11.2 | 3 | 3 | 3 | 3 | 3 | 3 | 3 | 3 | 3 | 3 | 3 |
| 37 | 11.2 | 0 | 0 | 0 | 0 | 0 | 0 | 0 | 0 | 0 | 0 | 0 |
| 11 | 11.2 | 3 | 0 | 3 | 3 | 3 | — | 0 | 3 | 3 | 3 | 3 |
| 87 | 11.2 | 3 | 0 | 3 | 3 | 3 | — | 3 | 3 | 3 | 3 | 3 |
| 97 | 11.2 | 0 | 0 | 1 | 1 | 1 | 2 | 0 | 0 | 1 | 3 | 3 |
| 20 | 11.2 | 3 | 0 | 3 | 2 | 3 | — | 0 | 3 | 1 | 3 | 3 |
| 41 | 11.2 | 0 | 0 | 0 | 0 | 0 | — | 0 | 0 | 0 | 0 | 0 |
| 22 | 11.2 | 0 | 0 | 1 | 2 | 3 | — | 0 | 0 | 0 | 3 | 3 |
| 75 | 11.2 | 0 | 0 | 3 | 3 | 3 | — | 0 | 3 | 1 | 3 | 3 |
| 14 | 11.2 | 3 | 3 | 3 | 3 | 3 | — | 3 | 3 | 3 | 3 | 3 |
| 30 | 11.2 | 0 | 0 | 0 | 0 | 0 | — | 0 | 0 | 0 | 0 | 0 |
| 23 | 11.2 | 0 | 0 | 0 | 2 | 3 | — | 0 | 0 | 0 | 3 | 3 |
| 35 | 11.2 | 1 | 0 | 0 | 0 | 2 | — | 0 | 0 | 0 | 0 | 3 |
| 17 | 11.2 | 3 | 2 | 3 | 3 | 3 | — | 2 | 3 | 3 | 3 | 3 |
| 34 | 11.2 | 1 | 1 | 0 | 1 | 0 | — | 0 | 0 | 0 | 1 | 3 |
| 50 | 11.2 | 0 | 0 | 3 | 3 | 3 | — | 0 | 0 | 0 | 2 | 3 |
| 55 | 11.2 | 3 | 2 | 3 | 3 | 3 | — | 3 | 3 | 3 | 3 | 3 |
| 55* | 11.2 | 3 | 3 | 3 | 3 | 3 | — | 3 | 3 | 3 | 3 | 3 |
| 33 | 11.2 | 0 | 0 | 0 | 0 | 0 | — | 0 | 0 | 0 | 0 | 0 |
| 49 | 11.2 | 0 | 0 | 0 | — | 0 | — | 0 | 0 | 0 | 0 | 0 |
| 65 | 11.2 | 0 | 0 | 3 | 3 | 3 | — | 0 | 3 | 2 | 3 | 3 |
| 51 | 11.2 | 0 | 0 | 0 | 0 | 0 | 0 | 0 | 0 | 0 | 0 | 0 |
| 68 | 11.2 | 0 | 0 | 0 | 0 | 1 | 2 | 0 | 0 | 0 | 3 | 3 |
| 67 | 11.2 | 3 | 2 | 3 | 3 | 3 | 3 | 3 | 3 | 3 | 3 | 3 |
| 76 | 11.2 | 0 | 0 | 0 | 0 | 0 | 0 | 0 | 0 | 0 | 0 | 0 |
| 77 | 11.2 | 0 | 0 | 0 | 1 | 0 | 0 | 0 | 0 | 0 | 0 | 0 |
| 83 | 11.2 | 0 | 0 | 0 | 0 | 0 | 0 | 0 | 0 | 0 | 0 | 0 |
| 82 | 11.2 | 0 | 0 | 0 | 0 | 0 | 0 | 0 | 0 | 0 | 0 | 3 |
| 84 | 11.2 | 3 | 1 | 3 | 3 | 3 | 3 | 0 | 3 | 3 | 3 | 3 |
| 66 | 11.2 | 0 | 0 | 1 | 0 | 0 | 0 | 0 | 0 | 0 | 1 | 1 |
| 85 | 11.2 | 3 | 3 | 3 | 3 | 3 | 3 | 3 | 3 | 3 | 3 | 3 |
| 86 | 11.2 | 3 | 1 | 3 | 3 | 3 | 3 | 3 | 3 | 3 | 3 | 3 |
| 112 | 11.2 | 0 | 0 | 3 | 2 | 3 | 3 | 1 | 0 | 3 | 3 | 3 |
| 70 | 11.2 | 0 | 0 | 1 | 3 | 3 | — | 0 | 2 | 0 | 3 | 3 |
| 24 | 11.2 | 3 | 0 | 3 | 3 | 3 | — | 2 | 3 | 0 | 3 | 3 |
| 36 | 11.2 | 0 | 0 | 0 | 0 | 0 | — | 0 | 0 | 0 | 0 | 0 |
| 71 | 11.2 | 3 | 0 | 3 | 3 | 3 | 3 | 0 | 3 | 1 | 3 | 3 |
| 103 | 11.2 | 1 | 0 | 2 | 3 | 3 | 3 | 0 | 2 | 0 | 3 | 3 |
| 100 | 11.2 | 0 | 0 | 0 | 0 | 0 | 0 | 0 | 0 | 0 | 0 | 0 |
| 69 | 11.2 | 3 | 3 | 3 | 3 | 3 | — | 3 | 3 | 3 | 3 | 3 |
| 72 | 11.2 | 3 | 2 | 3 | 3 | 3 | — | 3 | 3 | 3 | 3 | 3 |
| 99 | 11.2 | 3 | 0 | 3 | 0 | 3 | 3 | 0 | 1 | 0 | 0 | 1 |
| 81 | 11.2 | 3 | 0 | 3 | 3 | 3 | 3 | 2 | 3 | 3 | 3 | 3 |
| 42 | 11.2 | 0 | 1 | 0 | 0 | 3 | 0 | 1 | 0 | 0 | 3 | 3 |
| 74 | 11.2 | 3 | 0 | 3 | 3 | 3 | 3 | 0 | 3 | 0 | 3 | 3 |
| 78 | 11.2 | — | 0 | 0 | 0 | 0 | 0 | 0 | 0 | 0 | 0 | 0 |
| 73 | 11.2 | 3 | 1 | 3 | 3 | 3 | 3 | 1 | 0 | 0 | 3 | 3 |
| 98 | 11.2 | 0 | 0 | 0 | 0 | 0 | 0 | 0 | 0 | 0 | 0 | 0 |
| 10 | 11.2 | 3 | 0 | 2 | 3 | 3 | 3 | 2 | 3 | 1 | 3 | 3 |
| 101 | 11.2 | 3 | 3 | 3 | 3 | 3 | 3 | 3 | 1 | 3 | 3 | 3 |
| 25 | 11.2 | 3 | 3 | 3 | 3 | 3 | 3 | 3 | 3 | 3 | 3 | 3 |
| 102 | 11.2 | 0 | — | 2 | 0 | 3 | 3 | 0 | 0 | 0 | 1 | 1 |
| 134 | 11.2 | 3 | 1 | 3 | 3 | 3 | 3 | 3 | 3 | 3 | 3 | 3 |
| 130 | 11.2 | 1 | 0 | 3 | 0 | 3 | 3 | 1 | 0 | 0 | 1 | 3 |
| 128 | 11.2 | 0 | 0 | 0 | 0 | 3 | 1 | 0 | 0 | 0 | 0 | 1 |
| 104 | 11.2 | 1 | 0 | 3 | 3 | 3 | 3 | 1 | 3 | 0 | 3 | 3 |
| 127 | 11.2 | 0 | 0 | 3 | 3 | 3 | 3 | 1 | 3 | 0 | 3 | 3 |
| 129 | 11.2 | 3 | 2 | 3 | 3 | 3 | 3 | 1 | 3 | 3 | 3 | 3 |
| 131 | 11.2 | 3 | 3 | 3 | 3 | 3 | 3 | 3 | 3 | 3 | 3 | 3 |
| 105 | 11.2 | 3 | 0 | 3 | 3 | 3 | 3 | 2 | 3 | 1 | 3 | 3 |
| 133 | 11.2 | 3 | 3 | 3 | 3 | 3 | 3 | 3 | 3 | 3 | 3 | 3 |
| 80 | 11.2 | 3 | 2 | 3 | 3 | 3 | 3 | 3 | 3 | 3 | 3 | 3 |
| 79 | 11.2 | 0 | 0 | 0 | 0 | 0 | 0 | 0 | 0 | 0 | 0 | 0 |
| 26 | 11.2 | 3 | 0 | 3 | 3 | 3 | 3 | 2 | 3 | 3 | 3 | 3 |
| 27 | 11.2 | 1 | 0 | 2 | 2 | 3 | 3 | 0 | 1 | 0 | 3 | 3 |
| 123 | 11.2 | 3 | 2 | 3 | 3 | 3 | 3 | 3 | 3 | 3 | 3 | 3 |
| 124 | 11.2 | 3 | 0 | 3 | 3 | 3 | 3 | 2 | 3 | 2 | 3 | 3 |
| 119 | 11.2 | 0 | 0 | 0 | 0 | 0 | 0 | 0 | 0 | 0 | 0 | 0 |
| 109 | 11.2 | 0 | 0 | 0 | 0 | 0 | 0 | 0 | 0 | 0 | 3 | 3 |
| 43 | 11.2 | 0 | 0 | 0 | 0 | 0 | 0 | 0 | 0 | 0 | 0 | 0 |
| 107 | 11.2 | 0 | 0 | 0 | 0 | 0 | 0 | 0 | 0 | 0 | 0 | 0 |
| 110 | 11.2 | 3 | 0 | 3 | 0 | 3 | 2 | 3 | 2 | 3 | 3 | 3 |
| 111 | 11.2 | 3 | 1 | 3 | 3 | 3 | 3 | 3 | 3 | 3 | 3 | 3 |
| 106 | 11.2 | 0 | 0 | 0 | 0 | 0 | 0 | 0 | 0 | 0 | 0 | 0 |
| 120 | 11.2 | 0 | 0 | 0 | 0 | 0 | 0 | 0 | 0 | 0 | 0 | 0 |
| 122 | 11.2 | 3 | 1 | 3 | 3 | 3 | 3 | 3 | 3 | 3 | 3 | 3 |
| 117 | 11.2 | 3 | 3 | 3 | 3 | 3 | 3 | 3 | 3 | 3 | 3 | 3 |
| 118 | 11.2 | 0 | 0 | 0 | 0 | 0 | 0 | 0 | 0 | 0 | 0 | 0 |
| 113 | 11.2 | 3 | 1 | 2 | 2 | 3 | 3 | 1 | 0 | 0 | 3 | 3 |
| 121 | 11.2 | 0 | 0 | 0 | 0 | 1 | 0 | 0 | 0 | 0 | 0 | 0 |
| 125 | 11.2 | 3 | 1 | 3 | 3 | 3 | 3 | 3 | 3 | 3 | 3 | 3 |
| 137 | 11.2 | 3 | 0 | 3 | 3 | 3 | 3 | 1 | 3 | 1 | 3 | 3 |
| 136 | 11.2 | 3 | 2 | 3 | 3 | 3 | 3 | 1 | 3 | 3 | 3 | 3 |
| 121 | 11.2 | 0 | 0 | 0 | 0 | 0 | 1 | 0 | 0 | 0 | 0 | 0 |
| 125 | 11.2 | 3 | 1 | 3 | 3 | 3 | 3 | 3 | 3 | 3 | 3 | 3 |
| 137 | 11.2 | 3 | 0 | 3 | 3 | 3 | 3 | 1 | 3 | 1 | 3 | 3 |
| 136 | 11.2 | 3 | 2 | 3 | 3 | 3 | 3 | 1 | 3 | 3 | 3 | 3 |
| 135 | 11.2 | 1 | 0 | 0 | 0 | 0 | 0 | 1 | 0 | 0 | 0 | 3 |
| 138 | 11.2 | 3 | 3 | 3 | 3 | 3 | 3 | 3 | 3 | 3 | 3 | 3 |
| 139 | 11.2 | 3 | 3 | 3 | 3 | 3 | 3 | 3 | 3 | 3 | 3 | 3 |
| 140 | 11.2 | 2 | 0 | 0 | 0 | 3 | 3 | 0 | 1 | 0 | 3 | 3 |
| 141 | 11.2 | 3 | 0 | 3 | 2 | 3 | 3 | 0 | 3 | 3 | 3 | 3 |
| 142 | 11.2 | 3 | 0 | 3 | 3 | 3 | 3 | 3 | 0 | 3 | 3 | 3 |
| 143 | 11.2 | 0 | 0 | 1 | 0 | 2 | 1 | 0 | 1 | 0 | 3 | 3 |
| 144 | 11.2 | 3 | 0 | 1 | 0 | 0 | 0 | 0 | 0 | 3 | 0 | 3 |
| 145 | 11.2 | 3 | 3 | 3 | 3 | 3 | 3 | 1 | 3 | 3 | 3 | 3 |
| 146 | 11.2 | 3 | 3 | 3 | 3 | 3 | 3 | 3 | 3 | 3 | 3 | 3 |
| 147 | 11.2 | 3 | 3 | 3 | 3 | 3 | 3 | 3 | 3 | 3 | 3 | 3 |
| 148 | 11.2 | 3 | 3 | 3 | 3 | 3 | 3 | 3 | 3 | 3 | 3 | 3 |
| 149 | 11.2 | 0 | 0 | 0 | 0 | 3 | 3 | 0 | 0 | 0 | 3 | 3 |
| 150 | 11.2 | 3 | 3 | 3 | 3 | 3 | 3 | 3 | 3 | 3 | 3 | 3 |
| 151 | 11.2 | N | 3 | 3 | 33 | 3 | 3 | 3 | 3 | 3 | 3 | 3 |
| 152 | 11.2 | 0 | N | 0 | 1 | 1 | 3 | 0 | 2 | 0 | 3 | 3 |
| 153 | 11.2 | 0 | 0 | 2 | 2 | 3 | 3 | 0 | 0 | 1 | 3 | 3 |
| 154 | 11.2 | 0 | 0 | 0 | 0 | 3 | 0 | 0 | 0 | 0 | 0 | 0 |
| 155 | 11.2 | 1 | 0 | 0 | 0 | 0 | 0 | 0 | 0 | 0 | 0 | 0 |
| 156 | 11.2 | 0 | 3 | 0 | 1 | 1 | 1 | 0 | 0 | 0 | 0 | 1 |
| 157 | 11.2 | 3 | 0 | 1 | 2 | 3 | 3 | 0 | 3 | 1 | 0 | 3 |
| 158 | 11.2 | 1 | 0 | 0 | 0 | 2 | 0 | 1 | 0 | 0 | 0 | 0 |
| 159 | 11.2 | 0 | 1 | 3 | 3 | 3 | 3 | 0 | 0 | 1 | 3 | 3 |
| 160 | 11.2 | 0 | 0 | 0 | 0 | 0 | 0 | 0 | 0 | 0 | 0 | 1 |
| 161 | 11.2 | 3 | 0 | 3 | 3 | 3 | 3 | 0 | 3 | 1 | 3 | 3 |
| 162 | 11.2 | 3 | 0 | 3 | 3 | 3 | 3 | 2 | 0 | 3 | 3 | 3 |
| 163 | 11.2 | 3 | 1 | 3 | 3 | 3 | 3 | 3 | 3 | 3 | 3 | 3 |
| 164 | 11.2 | 1 | 0 | 1 | 3 | 3 | 3 | 0 | 0 | 0 | 1 | 3 |
| 165 | 11.2 | 0 | 0 | 2 | 3 | 2 | 2 | 0 | 3 | 3 | 3 | 3 |
| 166 | 11.2 | 3 | 3 | 3 | 3 | 3 | 3 | 3 | 3 | — | 3 | 3 |
| 167 | 11.2 | 1 | 2 | 2 | 2 | 3 | 3 | 0 | 1 | 0 | 3 | 3 |
| 168 | 11.2 | 3 | N | 3 | 3 | 3 | 3 | 1 | 2 | 1 | 3 | 3 |
| 169 | 11.2 | 3 | 1 | 3 | 3 | 3 | 3 | 1 | 3 | 0 | 3 | 3 |
| 170 | 11.2 | 3 | 1 | 3 | 3 | 3 | 3 | 1 | 3 | 1 | 3 | 3 |
| 171 | 11.2 | 3 | 2 | 3 | 3 | 3 | 3 | 1 | 3 | 3 | 3 | 3 |
| 172 | 11.2 | 3 | 3 | 3 | 3 | 3 | 3 | 3 | 3 | 3 | 3 | 3 |
| 173 | 11.2 | 3 | 2 | 3 | 3 | 3 | 3 | 3 | 3 | 3 | 3 | 3 |
| 174 | 11.2 | 3 | 0 | 3 | 3 | 3 | 3 | 0 | 3 | 1 | 3 | 3 |
| 175 | 11.2 | 3 | 1 | 3 | 3 | 3 | 3 | 1 | 3 | 0 | 3 | 3 |
| 176 | 11.2 | 0 | 0 | 1 | 1 | 1 | 2 | 0 | 1 | — | 1 | 3 |
| 177 | 11.2 | 3 | 1 | 3 | 3 | 3 | 3 | 0 | 3 | — | 3 | 3 |
| 178 | 11.2 | 3 | 0 | 3 | 3 | 3 | 3 | 1 | 3 | 3 | 3 | 3 |
| 179 | 11.2 | 3 | 0 | 2 | 2 | 3 | 3 | 0 | 2 | 3 | 3 | 3 |
| 180 | 11.2 | 3 | 0 | 3 | 3 | 3 | 3 | 1 | 3 | 3 | 3 | 3 |
| 181 | 11.2 | 0 | 0 | 0 | 0 | 0 | 1 | 0 | 0 | 0 | 1 | 3 |

TABLE 21-continued

| Example No. | kg/h | A | B | C | D | E | F | G | H | I | J | K |
|---|---|---|---|---|---|---|---|---|---|---|---|---|
| 182 | 11.2 | 0 | 0 | 2 | 0 | 0 | 0 | 0 | 0 | 0 | 3 | 2 |
| 183 | 11.2 | 0 | 0 | 0 | 0 | 0 | 0 | 0 | 0 | — | 0 | 0 |
| 184 | 11.2 | 1 | 0 | 2 | 3 | 1 | 2 | 0 | 3 | — | 3 | 3 |
| 185 | 11.2 | 0 | 0 | 0 | 0 | 0 | 0 | 0 | 0 | — | 0 | 0 |
| 186 | 11.2 | 3 | 1 | 3 | 3 | 3 | 3 | 0 | 0 | — | 3 | 3 |
| 187 | 11.2 | N | 0 | 0 | 0 | 3 | 0 | 0 | 1 | N | 3 | 0 |
| 188 | 11.2 | 3 | N | 3 | 3 | 3 | 3 | 3 | 3 | 3 | 3 | 3 |
| 189 | 11.2 | N | 0 | 0 | 0 | 3 | 2 | 0 | 0 | N | 0 | 3 |
| 190 | 11.2 | 3 | 1 | 3 | 3 | 3 | 3 | 2 | 3 | — | 3 | 3 |
| 191 | 11.2 | 0 | 0 | 2 | 0 | 0 | 3 | 0 | 0 | — | 3 | 3 |
| 192 | 11.2 | 1 | 1 | 0 | 0 | 1 | 1 | 0 | 0 | N | 1 | 3 |
| 193 | 11.2 | 0 | 3 | 2 | 3 | 3 | 3 | 0 | 1 | 3 | 3 | 3 |
| 194 | 11.2 | 0 | 3 | 3 | 3 | 3 | 3 | 3 | 3 | 3 | 3 | 3 |
| 195 | 11.2 | 3 | 3 | 3 | 3 | 3 | 3 | 3 | 3 | 3 | 3 | 3 |
| 196 | 11.2 | 3 | 3 | 3 | 3 | 3 | 3 | 1 | 3 | 0 | 3 | 3 |
| 197 | 11.2 | N | 0 | 0 | 0 | 0 | 0 | 0 | 0 | — | 0 | 0 |
| 198 | 11.2 | 3 | 3 | 3 | 3 | 3 | 3 | 3 | 3 | N | 3 | 3 |
| 199 | 11.2 | 3 | 3 | 3 | 3 | 3 | 3 | 3 | 3 | N | 3 | 3 |
| 200 | 11.2 | 1 | 1 | 3 | 3 | 3 | 3 | 0 | 0 | — | 3 | 3 |
| 201 | 11.2 | 3 | 1 | 3 | 3 | 3 | 3 | 0 | 3 | 3 | 3 | 3 |
| 202 | 11.2 | 1 | 0 | 0 | 0 | 0 | 0 | 0 | 0 | N | 0 | 0 |
| 203 | 11.2 | 3 | 1 | 3 | 3 | 3 | 3 | 2 | 3 | 3 | 3 | 3 |
| 204 | 11.2 | 0 | N | 0 | 0 | 0 | 1 | 0 | 0 | 0 | 1 | 3 |
| 205 | 11.2 | 0 | N | 0 | 1 | 1 | 3 | 0 | 2 | 0 | 3 | 3 |
| 206 | 11.2 | 3 | N | 2 | 1 | 1 | 3 | 1 | 0 | 0 | 0 | 0 |
| 207 | 11.2 | 3 | N | 3 | 3 | 3 | 3 | 3 | 3 | 2 | 3 | 3 |
| 208 | 11.2 | 3 | 3 | 3 | 3 | 3 | 3 | 3 | 3 | 3 | 3 | 3 |
| 209 | 11.2 | 3 | 3 | 3 | 3 | 3 | 3 | 2 | 3 | 3 | 3 | 3 |
| 210 | 11.2 | 3 | 3 | 3 | 3 | 3 | 3 | 2 | 3 | 2 | 3 | 3 |
| 211 | 11.2 | 3 | 3 | 3 | 3 | 3 | 3 | 3 | 3 | 3 | 3 | 3 |
| 212 | 11.2 | 3 | N | 3 | 3 | 3 | 3 | 1 | 3 | 1 | 3 | 3 |
| 213 | 11.2 | 3 | 3 | 3 | 3 | 3 | 3 | 3 | 3 | 3 | 3 | 3 |
| 215 | 11.2 | 3 | 1 | 3 | 3 | 3 | 3 | 0 | 3 | 3 | 3 | 3 |
| 216 | 11.2 | 0 | 3 | 1 | 1 | 3 | 1 | 0 | 0 | 0 | 0 | 3 |
| 217 | 11.2 | 0 | 0 | 0 | 0 | 0 | 0 | 0 | 0 | N | 0 | 0 |
| 219 | 11.2 | 0 | 0 | 0 | 0 | 0 | 0 | 0 | 0 | 0 | 0 | 0 |
| 220 | 11.2 | 0 | 1 | 0 | 0 | 0 | 0 | 0 | 0 | 0 | 0 | 0 |
| 221 | 11.2 | 0 | 0 | 0 | 0 | 2 | 1 | 0 | 0 | 0 | 0 | 3 |
| 222 | 11.2 | 0 | 0 | 0 | 0 | 0 | 0 | 0 | 0 | 0 | 0 | 0 |
| 223 | 11.2 | 0 | 0 | 0 | 0 | 0 | 0 | 0 | 0 | 0 | 0 | 0 |
| 224 | 11.2 | 0 | 0 | 0 | 0 | 0 | 0 | 0 | 0 | 0 | 0 | 0 |
| 225 | 11.2 | N | 0 | 0 | 0 | 0 | 0 | 0 | 0 | 0 | 0 | 2 |
| 226 | 11.2 | N | 0 | 0 | 0 | 0 | 0 | 0 | 0 | 0 | 0 | 0 |
| 227 | 11.2 | N | 0 | 0 | 0 | 0 | 0 | 0 | 1 | 0 | 0 | 0 |
| 233 | 11.2 | 3 | 2 | 3 | 3 | 3 | 3 | 2 | 3 | 3 | 3 | 3 |
| 234 | 11.2 | 3 | 1 | 1 | 3 | 3 | 3 | 0 | 0 | 2 | 3 | 3 |
| 235 | 11.2 | 3 | 1 | 3 | 3 | 3 | 3 | 0 | 3 | 3 | 3 | 3 |
| 236 | 11.2 | 3 | 0 | 3 | 3 | 3 | 3 | 0 | 3 | 1 | 3 | 3 |
| 237 | 11.2 | N | 1 | 3 | 3 | 3 | 3 | 3 | 0 | 3 | 3 | 3 |
| 238 | 11.2 | N | 2 | 3 | 3 | 3 | 3 | 0 | 3 | 3 | 3 | 3 |
| 239 | 11.2 | 1 | 1 | 3 | 3 | 3 | 3 | 2 | 3 | 3 | 3 | 3 |
| 240 | 11.2 | 0 | 0 | 0 | 0 | 3 | 2 | 0 | 0 | 1 | 0 | 3 |
| 241 | 11.2 | 3 | 1 | 3 | 3 | 3 | 3 | 3 | 3 | 3 | 3 | 3 |
| 242 | 11.2 | 2 | 1 | 3 | 3 | 3 | 3 | 0 | 3 | 1 | 3 | 3 |
| 243 | 11.2 | 3 | 1 | 3 | 3 | 3 | 3 | 0 | 3 | 1 | 3 | 3 |
| 244 | 11.2 | 3 | 3 | 3 | 3 | 3 | 3 | 3 | 3 | 1 | 3 | 3 |
| 245 | 11.2 | N | 0 | 3 | 3 | 3 | 3 | 3 | 3 | 3 | 3 | 3 |
| 246 | 11.2 | N | 3 | 3 | 3 | 3 | 3 | 2 | 0 | 0 | 3 | 3 |

The compounds were further tested by utilizing the above procedure on the following plant species:

| | |
|---|---|
| L - Soybean | R - Hemp Sesbania |
| M - Sugarbeet | E - Lambsquarters |
| N - Wheat | F - Smartweed |
| O - Rice | C - Velvetleaf |
| P - Sorghum | J - Downy Brome |
| B - Cocklebur | S - Panicum |
| Q - Wild Buckwheat | K - Barnyardgrass |
| D - Morning Glory | T - Crabgrass |

The results are summarized in Table 22.

TABLE 22

| Example No. | kg/h | L | M | N | O | P | B | Q | D | R | E | F | C | J | S | K | T |
|---|---|---|---|---|---|---|---|---|---|---|---|---|---|---|---|---|---|
| 2 | .056 | 0 | 0 | 0 | 0 | 0 | 0 | 0 | 0 | 2 | 0 | 0 | 0 | 0 | 0 | 0 | — |
|  | .28 | 0 | 0 | 0 | 0 | 3 | 0 | 0 | 0 | 0 | 0 | 0 | 0 | 0 | 0 | 0 | — |
|  | 1.12 | 0 | 1 | 0 | 0 | 0 | 0 | 0 | 0 | 3 | 1 | 1 | 3 | 0 | 0 | 0 | — |
|  | 5.6 | 0 | 1 | 3 | 3 | 3 | 1 | 1 | 3 | 3 | 2 | 2 | 2 | 3 | 3 | 3 | — |
|  | 11.2 | 2 | 2 | 3 | 3 | 3 | 0 | 3 | 3 | 3 | 3 | 2 | 1 | 3 | 3 | 3 | — |
| 4 | .28 | — | 0 | 0 | 0 | 0 | 0 | 0 | 0 | 0 | — | 0 | 0 | 0 | 0 | 0 |
|  | 1.12 | — | 0 | 0 | 0 | 0 | 0 | 1 | 0 | 3 | 0 | — | 1 | 0 | 0 | 0 | 3 |
|  | 5.6 | — | 3 | 3 | 2 | 3 | 0 | 2 | 2 | 0 | 3 | — | 3 | 3 | 3 | 3 | 3 |
| 5 | .28 | — | 0 | 0 | 0 | 0 | 0 | 0 | 0 | 3 | 3 | — | 0 | 0 | 0 | 0 | 1 |
|  | 1.12 | — | 0 | 0 | 0 | 0 | 0 | 1 | 0 | 2 | 0 | — | 0 | 0 | 0 | 0 | 1 |
|  | 5.6 | — | 1 | 0 | 0 | 0 | 0 | 0 | 0 | 1 | 2 | — | 0 | 3 | 2 | 3 | 3 |
| 9 | 1.12 | — | 0 | 0 | 0 | 0 | 0 | 2 | 0 | 3 | 0 | — | 0 | 1 | 0 | 0 | 0 |
|  | 5.6 | — | 0 | 0 | 0 | 0 | 0 | 0 | 0 | 2 | — | 0 | 1 | 2 | 3 | 3 |
| 1 | .056 | 0 | 0 | 0 | 0 | 0 | 0 | 0 | 0 | 0 | 0 | 0 | 0 | 0 | 0 | 0 | 0 |
|  | .28 | 0 | 0 | 0 | 0 | 0 | 0 | 0 | 0 | 0 | 0 | 0 | 0 | 0 | 0 | 0 | 0 |
|  | 1.12 | 1 | 1 | 1 | 2 | 1 | 0 | 0 | 1 | 2 | 2 | 0 | 0 | 1 | 2 | 3 | 3 |
|  | 5.6 | 3 | 3 | 3 | 3 | 3 | 0 | 2 | 3 | 2 | 3 | 3 | 1 | 3 | 3 | 3 | 3 |
| 6 | .056 | 0 | 0 | 0 | 0 | 0 | 0 | 0 | 0 | 0 | 0 | 0 | 0 | 0 | 0 | 0 | 0 |
|  | .28 | 0 | 0 | 0 | 0 | 0 | 0 | 0 | 0 | 0 | 0 | 0 | 0 | 0 | 0 | 0 | 0 |
|  | 1.12 | 0 | 1 | 1 | 1 | 1 | 0 | 0 | 0 | 1 | 0 | 0 | 0 | 0 | 2 | 3 | 3 |
|  | 5.6 | 3 | 3 | 3 | 3 | 3 | 1 | 3 | 3 | 3 | 3 | 2 | 1 | 3 | 3 | 3 | 3 |
| 7 | .056 | 0 | 0 | 0 | 0 | 0 | 0 | 0 | 0 | 0 | 0 | 0 | 0 | 0 | 0 | 0 | 3 |
|  | .28 | 0 | 1 | 0 | 0 | 0 | 0 | 0 | 0 | 0 | 0 | 0 | 0 | 0 | 0 | 3 |
|  | 1.12 | 0 | 1 | 3 | 3 | 0 | 0 | 0 | 0 | 1 | 1 | 0 | 1 | 1 | 2 | 3 |
|  |  | 0 | 1 | 3 | 2 | 0 | 0 | 0 | 0 | 3 | 1 | 0 | 1 | 1 | 2 | 3 |
|  | 5.6 | 3 | 3 | 3 | 3 | 3 | 0 | 2 | 3 | 3 | 3 | 1 | 3 | 3 | 3 | 3 |
|  |  | 3 | 3 | 3 | 3 | 3 | 0 | 3 | 3 | 3 | 3 | 1 | 3 | 3 | 3 | 3 |
| 94 | .056 | 0 | 0 | 0 | 0 | 0 | 0 | 0 | 0 | 0 | — | 0 | 0 | 0 | 0 | 1 |
|  | 1.12 | 0 | 1 | 0 | 1 | 0 | 0 | 0 | 0 | 1 | — | 0 | 0 | 0 | 1 | 2 |
|  | 5.6 | 0 | 2 | 3 | 2 | 2 | 0 | 0 | 0 | 1 | 3 | 3 | 1 | 2 | 3 | 3 |
| 95 | .056 | 0 | 0 | 0 | 0 | 0 | 0 | 0 | 0 | 0 | 0 | 0 | 0 | 0 | 0 | 0 |
|  | .28 | 0 | 0 | 0 | 0 | 0 | 0 | 0 | 0 | 0 | 0 | 0 | 0 | 0 | 0 | 0 |
|  | 1.12 | 0 | 0 | 0 | 0 | 0 | 0 | 0 | 0 | 0 | 0 | 0 | 0 | 0 | 0 | 2 |
|  | 5.6 | 0 | 1 | 2 | 1 | 1 | 0 | 0 | 1 | 1 | 1 | 0 | 3 | 3 | 3 | 3 |
| 12 | .056 | 0 | 0 | 0 | 0 | 0 | 0 | 0 | 0 | 0 | 0 | 0 | 0 | 0 | 0 | 0 |
|  | .28 | 0 | 2 | 0 | 0 | 3 | 0 | 3 | 1 | 0 | 0 | 1 | 1 | 3 | 3 | 3 |
|  |  | 0 | 3 | 0 | 0 | 3 | 0 | 0 | 0 | 1 | 3 | 0 | 1 | 3 | 3 | 3 |
|  | 1.12 | 1 | 3 | 2 | 2 | 3 | 0 | 3 | 3 | 1 | 3 | 2 | 3 | 3 | 3 | 3 |

TABLE 22-continued

| Example No. | kg/h | L | M | N | O | P | B | Q | D | R | E | F | C | J | S | K | T |
|---|---|---|---|---|---|---|---|---|---|---|---|---|---|---|---|---|---|
| | | 1 | 3 | 1 | 2 | 3 | 0 | 2 | 3 | 0 | 3 | 2 | 2 | 3 | 3 | 3 | 3 |
| | 5.6 | 3 | 3 | 3 | 3 | 3 | 2 | 3 | 3 | 3 | 3 | 3 | 3 | 3 | 3 | 3 | 3 |
| | | 3 | 3 | 3 | 3 | 3 | 1 | 3 | 3 | 3 | 3 | 3 | 3 | 3 | 3 | 3 | 3 |
| 63 | 5.6 | 3 | 3 | 3 | 3 | 3 | 1 | 3 | 3 | 3 | 3 | 3 | 3 | 3 | 3 | 3 | 3 |
| | | 3 | 3 | 3 | 3 | 3 | 1 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | | 3 | 3 | 3 | 3 | 3 | 0 | 1 | 2 | 3 | 3 | 3 | 3 | 3 | 3 | 3 | 3 |
| | .28 | 0 | 3 | 2 | 2 | 3 | 0 | 2 | 1 | 1 | 3 | 2 | 1 | 3 | 3 | 3 | 3 |
| | | 1 | 3 | 1 | 1 | 2 | 0 | 0 | 1 | 0 | 3 | 2 | 2 | 2 | 3 | 3 | 3 |
| | .056 | 0 | 1 | 0 | 1 | 0 | 0 | 0 | 0 | 0 | 1 | 1 | 1 | 1 | 1 | 3 | 2 |
| | | 0 | 0 | 0 | 0 | 0 | 0 | 0 | 0 | 0 | 0 | 0 | 0 | 0 | 0 | 2 | 1 |
| 57 | 5.6 | 1 | 3 | 3 | 3 | 3 | 1 | 3 | 3 | 2 | 3 | 2 | 2 | 3 | 3 | 3 | 3 |
| | | 1 | 3 | 3 | 3 | 3 | 0 | 2 | 2 | 1 | 3 | 2 | 1 | 3 | 3 | 3 | 3 |
| | 1.12 | 0 | 3 | 0 | 0 | 0 | 0 | 2 | 0 | 1 | 1 | 1 | 0 | 1 | 1 | 3 | 3 |
| | | 0 | 2 | 0 | 0 | 0 | 0 | 0 | 0 | 0 | 1 | 0 | 0 | 1 | 0 | 3 | 3 |
| | .28 | 0 | 3 | 0 | 0 | 0 | 0 | 0 | 0 | 0 | 0 | 0 | 0 | 0 | 0 | 2 | 1 |
| | .056 | 0 | 1 | 0 | 0 | 0 | 0 | 0 | 0 | 0 | 0 | 0 | 0 | 0 | 0 | 0 | 0 |
| 13 | .0112 | 0 | 0 | 0 | 0 | 0 | 0 | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| | .28 | 0 | 2 | 0 | 1 | 3 | 0 | 1 | 0 | 1 | 0 | 0 | 0 | 3 | 3 | 3 | 3 |
| | | 0 | 0 | 0 | 0 | 3 | 0 | 0 | 0 | 0 | 0 | 0 | 0 | 3 | 3 | 3 | 3 |
| | 1.12 | 1 | 3 | 2 | 2 | 3 | 0 | 3 | 3 | 2 | 2 | 3 | 0 | 2 | 3 | 3 | 3 |
| | | 1 | 3 | 1 | 1 | 2 | 0 | 2 | 2 | 2 | 3 | 3 | 1 | 1 | 3 | 3 | 3 |
| | 5.6 | 3 | 3 | 3 | 3 | 3 | 1 | 3 | 3 | 3 | 3 | 3 | 3 | 3 | 3 | 3 | 3 |
| | | 3 | 3 | 3 | 3 | 3 | 0 | 3 | 3 | 3 | 3 | 3 | 3 | 3 | 3 | 3 | 3 |
| 96 | .28 | 0 | 0 | 0 | 0 | 0 | 0 | 0 | 0 | 0 | 0 | — | 0 | 0 | 0 | 0 | 0 |
| | 1.12 | 0 | 0 | 0 | 0 | 0 | 0 | 0 | 0 | 0 | 0 | — | 0 | 0 | 0 | 0 | 0 |
| | 5.6 | 0 | 1 | 0 | 0 | 0 | 0 | 0 | 0 | 1 | 0 | — | 0 | 0 | 1 | 3 | 2 |
| 8 | 5.6 | 0 | 0 | 0 | 0 | 0 | 0 | 0 | 0 | 0 | 0 | 0 | 0 | 0 | 0 | 0 | 0 |
| | 1.12 | 0 | 0 | 0 | 0 | 0 | 0 | 0 | 0 | 0 | 0 | 0 | 0 | 0 | 0 | 0 | 0 |
| 46 | 5.6 | 2 | 3 | 1 | 3 | 3 | 1 | 3 | 2 | 1 | 3 | 1 | 0 | 3 | 3 | 3 | 3 |
| | 1.12 | 0 | 0 | 0 | 0 | 0 | 0 | 0 | 0 | 0 | 0 | 0 | 0 | 0 | 0 | 3 | 2 |
| 61 | 5.6 | 3 | 3 | 3 | 3 | 3 | 0 | 3 | 3 | 3 | 3 | 3 | 3 | 3 | 3 | 3 | 3 |
| | | 3 | 3 | 3 | 3 | 3 | 0 | 3 | 3 | 3 | 3 | 3 | 3 | 3 | 3 | 3 | 3 |
| | .0112 | 0 | 0 | 0 | 0 | 0 | 0 | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| | .28 | 0 | 1 | 0 | 1 | 2 | 0 | 1 | 0 | 1 | 1 | 1 | 0 | 2 | 2 | 3 | 3 |
| | | 0 | 1 | 0 | 0 | 2 | 0 | 0 | 0 | 2 | 0 | 0 | 2 | 3 | 3 | 3 | 3 |
| | 1.12 | 1 | 2 | 0 | 2 | 3 | 0 | 2 | 2 | 2 | 3 | 3 | 0 | 3 | 3 | 3 | 3 |
| | | 0 | 3 | 0 | 2 | 3 | 0 | 1 | 2 | 2 | 3 | 2 | 1 | 3 | 3 | 3 | 3 |
| 92 | 5.6 | 1 | 3 | 3 | 3 | 3 | 1 | 1 | 1 | 2 | 3 | — | 1 | 3 | 3 | 3 | 3 |
| | 1.12 | 1 | 1 | 0 | 0 | 0 | 0 | 0 | 0 | 0 | 2 | — | 0 | 0 | 0 | 1 | 0 |
| | .056 | 0 | 0 | 0 | 0 | 0 | 0 | 0 | 0 | 0 | 0 | — | 0 | 0 | 0 | 0 | 0 |
| | .28 | 0 | 0 | 0 | 0 | 0 | 0 | 0 | 0 | 0 | 0 | — | 0 | 0 | 0 | 0 | 0 |
| 89 | 5.6 | 0 | 0 | 0 | 0 | 0 | 0 | 0 | 0 | 0 | 1 | — | 0 | 0 | 0 | 1 | 1 |
| | 1.12 | 0 | 0 | 0 | 0 | 0 | 0 | 0 | 0 | 0 | 1 | — | 0 | 0 | 0 | 1 | 2 |
| 40 | .056 | 0 | 0 | 0 | 0 | 0 | 0 | 0 | 0 | 0 | 0 | 0 | 0 | 0 | 0 | 0 | 0 |
| | .28 | 0 | 0 | 0 | 0 | 0 | — | 0 | 0 | 0 | 0 | 0 | 0 | 0 | 0 | 0 | 0 |
| | 1.12 | 0 | 1 | 2 | 1 | 3 | 0 | 1 | 0 | 0 | 2 | 1 | 2 | 1 | 3 | 3 | 3 |
| | 5.6 | 2 | 3 | 3 | 3 | 3 | 1 | 2 | 3 | 2 | 3 | 3 | 2 | 3 | 3 | 3 | 3 |
| 59 | 1.12 | 3 | 3 | 3 | 3 | 3 | 0 | 3 | 3 | 2 | 3 | — | 2 | 3 | 3 | 3 | 3 |
| | | 3 | 3 | 3 | 3 | 3 | 0 | 0 | 3 | 2 | 3 | — | 3 | 3 | 3 | 3 | 3 |
| | .28 | 0 | 2 | 0 | 2 | 2 | 0 | 0 | 0 | 0 | 0 | — | 0 | 3 | 3 | 3 | 3 |
| | 5.6 | 3 | 3 | 3 | 3 | 3 | 1 | 3 | 3 | 3 | 3 | — | 3 | 3 | 3 | 3 | 3 |
| | | 3 | 3 | 3 | 3 | 3 | 1 | 3 | 3 | 3 | 3 | — | 3 | 3 | 3 | 3 | 3 |
| | .056 | 0 | 0 | 0 | 0 | 0 | 0 | 0 | 0 | 0 | 0 | — | 0 | 0 | 0 | 0 | 0 |
| 60 | 5.6 | 0 | 1. | 3 | 0 | 0 | 0 | 0 | 0 | 1 | 1 | — | 0 | 1 | 3 | 3 | 3 |
| | 1.12 | 0 | 0 | 0 | 0 | 0 | 0 | 0 | 0 | 0 | 0 | — | 0 | 0 | 0 | 0 | 0 |
| | .28 | 0 | 0 | 0 | 0 | 0 | 0 | 0 | 0 | 0 | 0 | — | 0 | 0 | 0 | 0 | 0 |
| 52 | .0112 | 0 | 0 | 0 | 0 | 0 | 0 | 0 | 0 | 0 | 0 | 0 | 0 | 0 | 0 | 0 | 0 |
| | .056 | 0 | 3 | 1 | 1 | 2 | 0 | 1 | 1 | 0 | 3 | 1 | 1 | 2 | 3 | 3 | 3 |
| | | 0 | 3 | 0 | 0 | 2 | 0 | 0 | 0 | 3 | 3 | 1 | 2 | 2 | 3 | 3 | 3 |
| | .28 | 2 | 3 | 3 | 3 | 3 | 0 | 3 | 2 | 3 | 3 | 2 | 3 | 3 | 3 | 3 | 3 |
| | | 1 | 3 | 3 | 3 | 3 | 0 | 1 | 2 | 3 | 3 | 2 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | | 3 | 3 | 3 | 3 | 3 | 0 | 3 | 2 | 3 | 3 | 2 | 3 | 3 | 3 | 3 | 3 |
| | 5.6 | 3 | 3 | 3 | 3 | 3 | 0 | 3 | 3 | 3 | 3 | 3 | 3 | 3 | 3 | 3 | 3 |
| | | 3 | 3 | 3 | 3 | 3 | 0 | 3 | 3 | 3 | 3 | 3 | 3 | 3 | 3 | 3 | 3 |
| | .056 | 0 | 2 | 1 | 2 | 1 | 0 | 1 | 2 | 1 | 2 | 2 | 1 | 2 | 3 | 2 | 2 |
| | 5.6 | 3 | 3 | 3 | 3 | 2 | 3 | 3 | 3 | 3 | 3 | 3 | 3 | 3 | 3 | 3 | 3 |
| | 1.12 | 2 | 3 | 3 | 3 | 3 | 2 | 3 | 2 | 3 | 3 | 2 | 3 | 3 | 3 | 3 | 3 |
| | .28 | 1 | 3 | 3 | 3 | 3 | 1 | 3 | 3 | 2 | 3 | 2 | 2 | 3 | 3 | 3 | 3 |
| 62 | .056 | 0 | 0 | 0 | 0 | 0 | 0 | 0 | 0 | 0 | 0 | 0 | 0 | 0 | 0 | 0 | 0 |
| | .28 | 0 | 0 | 0 | 0 | 0 | 0 | 0 | 0 | 0 | 0 | 0 | 0 | 0 | 0 | 0 | 2 |
| | 1.12 | 0 | 0 | 0 | 0 | 0 | 0 | 0 | 0 | 0 | 3 | 1 | 0 | 0 | 3 | 3 | 3 |
| | 5.6 | 1 | 3 | 2 | 2 | 3 | 1 | 3 | 2 | 3 | 3 | 3 | 2 | 3 | 3 | 3 | 3 |
| 90 | .28 | 0 | 0 | 0 | 0 | 0 | 0 | 0 | 0 | 0 | 0 | 0 | 0 | 0 | 0 | 0 | 0 |
| | 1.12 | 0 | 0 | 0 | 0 | 0 | 0 | 0 | 0 | 0 | 0 | 0 | 0 | 0 | 0 | 0 | 2 |
| | 5.6 | 0 | 0 | 0 | 0 | 1 | 0 | 0 | 0 | 2 | 0 | 1 | 1 | 2 | 3 | 3 | 3 |
| 18 | .28 | 0 | 0 | 0 | 0 | 0 | 0 | 0 | 0 | 0 | 0 | 0 | 0 | 0 | 0 | 0 | 0 |
| | 1.12 | 1 | 2 | 1 | 2 | 3 | 0 | 0 | 2 | 2 | 3 | 2 | 0 | 3 | 3 | 3 | 3 |

TABLE 22-continued

| Example No. | kg/h | L | M | N | O | P | B | Q | D | R | E | F | C | J | S | K | T |
|---|---|---|---|---|---|---|---|---|---|---|---|---|---|---|---|---|---|
| | 5.6 | 3 | 3 | 3 | 3 | 3 | 0 | 3 | 3 | 3 | 3 | 3 | 3 | 3 | 3 | 3 | 3 |
| | .056 | 0 | 0 | 0 | 0 | 0 | 0 | 0 | 0 | 0 | 0 | 0 | 0 | 0 | 0 | 0 | 0 |
| | .0112 | 0 | 0 | 0 | 0 | 0 | 0 | 0 | 0 | 0 | 0 | 0 | 0 | 0 | 0 | 0 | 0 |
| 29 | 5.6 | 0 | 2 | 2 | 1 | 3 | 0 | 1 | 0 | 1 | 2 | 1 | 0 | 1 | 3 | 3 | 3 |
| | 1.12 | 0 | 0 | 0 | 0 | 0 | 0 | 0 | 0 | 0 | 0 | 0 | 0 | 0 | 0 | 0 | 0 |
| 47 | 5.6 | 1 | 3 | 3 | 3 | 3 | 0 | 2 | 2 | 2 | 3 | 3 | 2 | 3 | 3 | 3 | 3 |
| | 1.12 | 0 | 1 | 0 | 0 | 0 | 0 | 1 | 0 | 0 | 0 | 0 | 1 | 0 | 1 | 1 | 0 |
| | .28 | 0 | 0 | 0 | 0 | 0 | 0 | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| 93 | .28 | 0 | 0 | 0 | 0 | 0 | 0 | 0 | 0 | 0 | 0 | 0 | 0 | 0 | 0 | 0 | 0 |
| | 5.6 | 1 | 3 | 3 | 3 | 3 | 2 | 1 | 3 | 2 | 3 | 3 | 2 | 3 | 3 | 3 | 3 |
| | 1.12 | 0 | 1 | 0 | 0 | 0 | 0 | 0 | 0 | 1 | 1 | 1 | 0 | 2 | 1 | 1 | 2 |
| | .056 | 0 | 1 | 0 | 0 | 0 | 0 | 0 | 0 | 1 | 1 | 0 | 0 | 0 | 0 | 0 | 1 |
| 15 | 5.6 | 3 | 3 | 3 | 3 | 3 | 0 | 3 | 3 | 3 | 3 | 3 | 3 | 3 | 3 | 3 | 3 |
| | 1.12 | 0 | 3 | 2 | 3 | 3 | 0 | 2 | 2 | 2 | 3 | 3 | 2 | 3 | 3 | 3 | 3 |
| | .28 | 0 | 1 | 0 | 0 | 0 | 0 | 0 | 0 | 1 | 1 | 1 | 0 | 0 | 1 | 3 | 3 |
| | .0112 | 0 | 0 | 0 | 0 | 0 | 0 | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| 44 | .056 | 0 | 0 | 0 | 0 | 0 | 0 | 0 | 0 | 0 | 2 | 1 | 0 | 0 | 0 | 0 | 1 |
| | .28 | 0 | 0 | 0 | 0 | 0 | 0 | 0 | 0 | 0 | 0 | 0 | 0 | 0 | 0 | 0 | 1 |
| | 1.12 | 0 | 1 | 0 | 1 | 3 | 0 | 1 | 0 | 2 | 2 | 2 | 0 | 1 | 3 | 3 | 3 |
| | 5.6 | 1 | 3 | 3 | 3 | 3 | 0 | 2 | 2 | 3 | 3 | 3 | 2 | 3 | 3 | 3 | 3 |
| 31 | 5.6 | 0 | 2 | 0 | 1 | 3 | 0 | 2 | 2 | 2 | 3 | 1 | 0 | 3 | 3 | 3 | 3 |
| | .28 | 0 | 0 | 0 | 0 | 0 | 0 | 0 | 0 | 0 | 0 | 0 | 0 | 0 | 0 | 0 | 1 |
| | 1.12 | 0 | 2 | 0 | 0 | 0 | 0 | 0 | 0 | 0 | 2 | 0 | 0 | 2 | 1 | 2 | 1 |
| | .056 | 0 | 0 | 0 | 0 | 0 | 0 | 0 | 0 | 0 | 0 | 0 | 0 | 0 | 0 | 0 | 0 |
| 53 | 1.12 | 3 | 3 | 3 | 3 | 3 | 1 | 3 | 3 | 3 | 3 | 3 | 3 | 3 | 3 | 3 | 3 |
| | | 3 | 3 | 3 | 3 | 3 | 0 | 2 | 3 | 3 | 3 | 3 | 3 | 3 | 3 | 3 | 3 |
| | 5.6 | 3 | 3 | 3 | 3 | 3 | 3 | 3 | 3 | 3 | 3 | 3 | 3 | 3 | 3 | 3 | 3 |
| | | 3 | 3 | 3 | 3 | 3 | 2 | 3 | 3 | 3 | 3 | 3 | 3 | 3 | 3 | 3 | 3 |
| | .28 | 0 | 3 | 3 | 3 | 3 | 0 | 2 | 2 | 3 | 3 | 2 | 3 | 3 | 3 | 3 | 3 |
| | | 0 | 3 | 3 | 3 | 3 | 0 | 0 | 1 | 1 | 3 | 2 | 2 | 3 | 3 | 3 | 3 |
| | .056 | 2 | 3 | 3 | 3 | 1 | 0 | 1 | 3 | 3 | 3 | 3 | 2 | 0 | 3 | 3 | 3 |
| | | 1 | 3 | 2 | 3 | 0 | 0 | 0 | 2 | 2 | 3 | 3 | 1 | 0 | 3 | 3 | 3 |
| | .0112 | 0 | 3 | 0 | 2 | 1 | 0 | 2 | 1 | 2 | 3 | 2 | 2 | 0 | 2 | 2 | 3 |
| | | 0 | 2 | 0 | 1 | 0 | 0 | 0 | 0 | 0 | 0 | 0 | 0 | 0 | 1 | 2 | 3 |
| 16 | 5.6 | 3 | 3 | 3 | 3 | 3 | 3 | 3 | 3 | 3 | 3 | 3 | 3 | 3 | 3 | 3 | 3 |
| | 1.12 | 2 | 3 | 3 | 3 | 3 | 2 | 3 | 3 | 3 | 3 | 3 | 2 | 3 | 3 | 3 | 3 |
| | .28 | 0 | 1 | 0 | 2 | 2 | 0 | 1 | 2 | 2 | 2 | 2 | 1 | 3 | 3 | 3 | 3 |
| | .056 | 0 | 0 | 0 | 0 | 0 | 0 | 0 | 0 | 0 | 0 | 0 | 0 | 0 | 0 | 2 | 3 |
| | .0112 | 0 | 0 | 0 | 0 | 0 | 0 | 0 | 1 | 0 | 1 | 0 | 0 | 0 | 0 | 1 | 0 |
| 21 | 5.6 | 0 | 2 | 1 | 1 | 1 | 0 | 0 | 1 | 2 | 3 | 3 | 2 | 3 | 3 | 3 | 3 |
| | 1.12 | 0 | 0 | 0 | 0 | 0 | 0 | 0 | 0 | 2 | 2 | 0 | 0 | 0 | 2 | 2 | 2 |
| | .28 | 0 | 0 | 0 | 0 | 0 | 0 | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| 64 | .056 | 0 | 0 | 0 | 0 | 0 | 0 | 0 | 0 | 0 | 0 | 0 | 0 | 0 | 0 | 0 | 1 |
| | 5.6 | 2 | 3 | 3 | 3 | 3 | 0 | 3 | 3 | 3 | 3 | 3 | 3 | 3 | 3 | 3 | 3 |
| | 1.12 | 1 | 3 | 0 | 2 | 3 | 0 | 3 | 3 | 3 | 3 | 2 | 3 | 3 | 3 | 3 | 3 |
| | .28 | 0 | 0 | 0 | 0 | 0 | 0 | 0 | 0 | 0 | 0 | 0 | 0 | 0 | 2 | 2 | 2 |
| 54 | .0112 | 0 | 0 | 0 | 0 | 0 | 0 | 0 | 0 | 0 | — | 0 | 0 | 0 | 1 | 1 | 1 |
| | 5.6 | 3 | 3 | 3 | 3 | 3 | 3 | 3 | 3 | 3 | — | 3 | 3 | 3 | 3 | 3 | 3 |
| | .056 | 2 | 2 | 0 | 2 | 2 | 0 | 0 | 0 | 1 | 2 | — | 0 | 3 | 3 | 3 | 3 |
| | 1.12 | 3 | 3 | 3 | 3 | 3 | 0 | 3 | 3 | 3 | 3 | — | 3 | 3 | 3 | 3 | 3 |
| | .28 | 2 | 3 | 3 | 3 | 3 | 0 | 3 | 3 | 2 | 3 | — | 2 | 3 | 3 | 3 | 3 |
| 11 | 5.6 | 2 | 3 | 3 | 3 | 3 | 0 | 3 | 3 | 3 | 3 | — | 3 | 3 | 3 | 3 | 3 |
| | 1.12 | L | 3 | 1 | 3 | 3 | 0 | 3 | 3 | 3 | 3 | — | 3 | 3 | 3 | 3 | 3 |
| | .28 | 0 | 2 | 0 | 3 | 1 | 0 | 1 | 0 | 1 | 1 | — | 1 | 0 | 2 | 2 | 3 |
| | .056 | 0 | 0 | 0 | 0 | 0 | 0 | 0 | 0 | 0 | 0 | — | 0 | 0 | 0 | 1 | 0 |
| | .0112 | 0 | 0 | 0 | 0 | 0 | 0 | 0 | 0 | 0 | 0 | — | 0 | 0 | 0 | 0 | 0 |
| 87 | 5.6 | 3 | 3 | 3 | 3 | 3 | 0 | 3 | 3 | 3 | 3 | — | 3 | 3 | 3 | 3 | 3 |
| | 1.12 | 2 | 3 | 2 | 3 | 3 | 0 | 3 | 3 | 2 | 3 | — | 2 | 3 | 3 | 3 | 3 |
| | .0112 | 0 | 0 | 0 | 0 | 0 | 0 | 0 | 0 | 0 | 0 | — | 0 | 0 | 0 | 0 | 0 |
| | .056 | 0 | 0 | 0 | 0 | 0 | 0 | 0 | 0 | 0 | 0 | — | 0 | 0 | 0 | 1 | 0 |
| | .28 | 1 | 2 | 0 | 0 | 3 | 0 | 1 | 0 | 0 | 0 | — | 1 | 1 | 3 | 3 | 3 |
| 97 | 5.6 | 1 | 3 | 0 | 0 | 0 | 0 | 0 | 0 | 2 | 2 | 1 | 0 | 0 | 3 | 3 | 3 |
| | .28 | 0 | 0 | 0 | 0 | 0 | 0 | 0 | 0 | 0 | 0 | 0 | 0 | 0 | 0 | 0 | 0 |
| | 1.12 | 0 | 0 | 0 | 0 | 0 | 0 | 0 | 0 | 1 | 1 | 0 | 0 | 0 | 1 | 1 | 1 |
| 20 | 5.6 | 1 | 3 | 3 | 1 | 3 | 0 | 2 | 3 | 2 | 3 | — | 2 | 3 | 3 | 3 | 3 |
| | 1.12 | 0 | 0 | 0 | 0 | 0 | 0 | 0 | 0 | 1 | — | 1 | 0 | 0 | 1 | 2 | |
| | .28 | 0 | 0 | 0 | 0 | 0 | 0 | 0 | 0 | 0 | 0 | — | 0 | 0 | 0 | 0 | 0 |
| | .056 | 0 | 0 | 0 | 0 | 0 | 0 | 0 | 0 | 0 | — | 0 | 0 | 0 | 0 | 0 | |
| 22 | 5.6 | 0 | 2 | 1 | 1 | 3 | 1 | 3 | 2 | 2 | 3 | — | 2 | 3 | 3 | 3 | 3 |
| | 1.12 | 0 | 0 | 0 | 0 | 0 | 0 | 0 | 0 | 0 | 0 | — | 0 | 1 | 2 | 2 | 2 |
| | .28 | 0 | 0 | 0 | 0 | 0 | 0 | 0 | 0 | 0 | 0 | — | 0 | 0 | 0 | 0 | 0 |
| 75 | .28 | 0 | 2 | 1 | 2 | 1 | 0 | 3 | 2 | 1 | 2 | — | 1 | 3 | 1 | 3 | 3 |
| | .056 | 1 | 2 | 0 | 2 | 0 | 0 | 0 | 0 | 0 | 0 | — | 0 | 0 | 0 | 2 | 2 |
| | 5.6 | 0 | 3 | 3 | 3 | 3 | 1 | 3 | 3 | 3 | 3 | — | 3 | 3 | 3 | 3 | 3 |
| | 1.12 | 0 | 2 | 2 | 2 | 3 | 0 | 2 | 1 | 1 | 3 | — | 1 | 3 | 2 | 3 | 3 |
| 14 | .0112 | 0 | 0 | 0 | 0 | 0 | 0 | 0 | 0 | 0 | — | 0 | 0 | 0 | 0 | 2 | |
| | 1.12 | 3 | 3 | 3 | 3 | 3 | 1 | 3 | 3 | 3 | 3 | — | 3 | 3 | 3 | 3 | 3 |
| | 5.6 | 3 | 3 | 3 | 3 | 3 | 2 | 3 | 3 | 3 | 3 | — | 3 | 3 | 3 | 3 | 3 |

TABLE 22-continued

| Example No. | kg/h | L | M | N | O | P | B | Q | D | R | E | F | C | J | S | K | T |
|---|---|---|---|---|---|---|---|---|---|---|---|---|---|---|---|---|---|
| | .056 | 0 | 2 | 2 | 2 | 3 | 0 | 3 | 1 | 1 | 2 | — | 1 | 3 | 3 | 3 | 3 |
| | .28 | 2 | 3 | 3 | 3 | 3 | 1 | 3 | 3 | 3 | 3 | — | 3 | 3 | 3 | 3 | 3 |
| 23 | 5.6 | 1 | 2 | 0 | 0 | 1 | 0 | 1 | 2 | 0 | 3 | — | 1 | 2 | 1 | 2 | 3 |
| | 1.12 | 0 | 0 | 0 | 0 | 0 | 0 | 0 | 0 | 0 | 0 | — | 0 | 1 | 0 | 0 | 1 |
| | .28 | 0 | 0 | 0 | 0 | 0 | 0 | 0 | 0 | 0 | 0 | — | 0 | 0 | 0 | 0 | 0 |
| 35 | 5.6 | 0 | 0 | 0 | 0 | 0 | 0 | 0 | 0 | 0 | 0 | — | 0 | 0 | 0 | 0 | 0 |
| | 1.12 | 0 | 0 | 0 | 0 | 0 | 0 | 0 | 0 | 0 | 0 | — | 0 | 0 | 0 | 0 | 0 |
| 17 | 5.6 | 3 | 3 | 3 | 3 | 3 | 3 | 3 | 3 | 3 | 3 | — | 3 | 3 | 3 | 3 | 3 |
| | 1.12 | 3 | 3 | 3 | 3 | 3 | 2 | 3 | 3 | 3 | 3 | — | 3 | 3 | 3 | 3 | 3 |
| | .0112 | 0 | 0 | 0 | 0 | 0 | 0 | 0 | 0 | 0 | 0 | — | 0 | 0 | 0 | 0 | 0 |
| | .056 | 0 | 0 | 0 | 0 | 0 | 0 | 0 | 0 | 0 | 0 | — | 0 | 2 | 2 | 2 | 3 |
| | .28 | 0 | 1 | 0 | 0 | 2 | 0 | 0 | 2 | 0 | 0 | — | 0 | 2 | 3 | 3 | 3 |
| 34 | 5.6 | 0 | 0 | 0 | 0 | 0 | 0 | 0 | 0 | 0 | 0 | — | 0 | 0 | 0 | 0 | 2 |
| | 1.12 | 0 | 0 | 0 | 0 | 0 | 0 | 0 | 0 | 0 | 0 | — | 0 | 1 | 0 | 1 | 0 |
| 50 | 5.6 | 0 | 2 | 0 | 2 | 3 | 0 | 3 | 2 | 2 | 3 | — | 0 | 2 | 3 | 3 | 3 |
| | 1.12 | 0 | 1 | 0 | 0 | 0 | 0 | 0 | 1 | 0 | 1 | — | 0 | 0 | 0 | 1 | 1 |
| | .28 | 0 | 0 | 0 | 0 | 0 | 0 | 0 | 0 | 0 | 0 | — | 0 | 0 | 0 | 0 | 1 |
| 55 | 5.6 | 3 | 3 | 3 | 3 | 3 | 1 | 3 | 3 | 3 | 3 | — | 3 | 3 | 3 | 3 | 3 |
| | 1.12 | 3 | 3 | 3 | 3 | 3 | 0 | 3 | 3 | 3 | 3 | — | 3 | 3 | 3 | 3 | 3 |
| | .28 | 2 | 3 | 2 | 3 | 3 | 0 | 3 | 3 | 3 | 3 | — | 2 | 3 | 3 | 3 | 3 |
| | .056 | 0 | 2 | 0 | 1 | 3 | 0 | 2 | 2 | 2 | 3 | — | 2 | 3 | 3 | 3 | 3 |
| | .0112 | 0 | 0 | 0 | 0 | 0 | 0 | 0 | 0 | 0 | 0 | — | 0 | 0 | 0 | 0 | 2 |
| 65 | .28 | 0 | 0 | 0 | 0 | 1 | 0 | 0 | 0 | 0 | 0 | — | 0 | 2 | 2 | 2 | 2 |
| | .056 | 0 | 0 | 0 | 0 | 0 | 0 | 0 | 0 | 0 | 0 | — | 0 | 0 | 1 | 2 | 1 |
| | 5.6 | 1 | 3 | 3 | 3 | 3 | 0 | 3 | 3 | 3 | 3 | — | 2 | 3 | 3 | 3 | 3 |
| | 1.12 | 0 | 1 | 3 | 2 | 3 | 0 | 3 | 0 | 1 | 2 | — | 0 | 3 | 3 | 3 | 3 |
| 68 | .28 | 0 | 0 | 0 | 0 | 0 | 0 | 0 | 0 | 0 | 0 | 0 | 0 | 0 | 0 | 0 | 0 |
| | 1.12 | 0 | 0 | 0 | 0 | 0 | 0 | 0 | 0 | 0 | 0 | 0 | 0 | 0 | 0 | 0 | 0 |
| | 5.6 | 0 | 0 | 0 | 0 | 1 | 0 | 0 | 2 | 0 | 0 | 0 | 0 | 3 | 1 | 1 | 3 |
| 67 | 5.6 | 3 | 3 | 3 | 3 | 3 | 3 | 3 | 3 | 3 | 3 | 3 | 3 | 3 | 3 | 3 | 3 |
| | 1.12 | 3 | 3 | 3 | 3 | 3 | 2 | 3 | 3 | 3 | 3 | 3 | 3 | 3 | 3 | 3 | 3 |
| | .28 | 1 | 3 | 3 | 3 | 3 | 0 | 3 | 2 | 2 | 3 | 3 | 1 | 3 | 3 | 3 | 3 |
| | .056 | 0 | 0 | 0 | 0 | 3 | 0 | 2 | 1 | 0 | 1 | 0 | 0 | 1 | 1 | 1 | 2 |
| | .0112 | 0 | 0 | 0 | 0 | 0 | 0 | 0 | 0 | 0 | 0 | 0 | 0 | 0 | 0 | 1 | 2 |
| 82 | 5.6 | 0 | 0 | 0 | 0 | 3 | 0 | 0 | 1 | 0 | 1 | 1 | 1 | 1 | 1 | 2 | 3 |
| | 1.12 | 0 | 0 | 0 | 0 | 0 | 0 | 0 | 0 | 0 | 0 | 0 | 0 | 0 | 0 | 0 | 0 |
| 84 | 5.6 | 1 | 3 | 3 | 3 | 3 | 1 | 3 | 3 | 3 | 3 | 3 | 2 | 3 | 3 | 3 | 3 |
| | 1.12 | 0 | 2 | 0 | 2 | 3 | 0 | 2 | 2 | 1 | 0 | 0 | 0 | 3 | 3 | 3 | 3 |
| | .28 | 0 | 0 | 0 | 0 | 0 | 0 | 0 | 0 | 0 | 0 | 0 | 0 | 0 | 0 | 0 | 2 |
| | .056 | 0 | 0 | 0 | 0 | 0 | 0 | 0 | 0 | 0 | 0 | 0 | 0 | 0 | 0 | 0 | 0 |
| 85 | 5.6 | 3 | 3 | 3 | 3 | 3 | 2 | 3 | 3 | 3 | 3 | 3 | 3 | 3 | 3 | 3 | 3 |
| | 1.12 | 1 | 3 | 3 | 3 | 3 | 0 | 2 | 2 | 2 | 3 | 3 | 2 | 3 | 3 | 3 | 3 |
| | .28 | 0 | 2 | 0 | 1 | 1 | 0 | 1 | 2 | 0 | 2 | 1 | 0 | 2 | 2 | 2 | 2 |
| | .056 | 0 | 0 | 0 | 0 | 0 | 0 | 0 | 0 | 0 | 0 | 0 | 0 | 0 | 1 | 1 | 2 |
| 86 | .0112 | 0 | 0 | 0 | 0 | 0 | 0 | 0 | 0 | 0 | 0 | 0 | 0 | 0 | 0 | 0 | 0 |
| | 5.6 | 3 | 3 | 3 | 3 | 3 | 0 | 3 | 3 | 3 | 3 | 3 | 3 | 3 | 3 | 3 | 3 |
| | 1.12 | 2 | 3 | 3 | 3 | 3 | 0 | 3 | 3 | 3 | 3 | 3 | 3 | 3 | 3 | 3 | 3 |
| | .28 | 1 | 2 | 3 | 3 | 3 | 0 | 3 | 1 | 2 | 2 | 2 | 1 | 3 | 3 | 3 | 3 |
| | .056 | 0 | 2 | 0 | 1 | 3 | 0 | 2 | 0 | 1 | 2 | 1 | 0 | 2 | 2 | 2 | 3 |
| 112 | .28 | 0 | 0 | 0 | 0 | 0 | 0 | 0 | 0 | 0 | 0 | 0 | 0 | 0 | 0 | 0 | 1 |
| | 1.12 | 0 | 2 | 1 | 0 | 3 | 0 | 2 | 1 | 1 | 1 | 2 | 2 | 2 | 2 | 2 | 2 |
| | 5.6 | 0 | 3 | 3 | 2 | 3 | 3 | 3 | 3 | 3 | 3 | 3 | 2 | 3 | 3 | 3 | 3 |
| 70 | 5.6 | 0 | 2 | 2 | 2 | 2 | 0 | 2 | 2 | 3 | 3 | — | 1 | 3 | 3 | 3 | 3 |
| | .28 | 0 | 0 | 0 | 0 | 0 | 0 | 0 | 0 | 0 | 0 | — | 0 | 0 | 0 | 0 | 0 |
| | 1.12 | 0 | 1 | 0 | 0 | 0 | 0 | 0 | 0 | 0 | 0 | — | 0 | 0 | 1 | 2 | 3 |
| | .056 | 0 | 0 | 0 | 0 | 0 | 0 | 0 | 0 | 0 | 0 | — | 0 | 0 | 0 | 0 | 0 |
| 24 | 1.12 | 0 | 3 | 3 | 2 | 2 | 0 | 2 | 2 | 2 | 3 | 2 | 2 | 3 | 3 | 3 | 3 |
| | 5.6 | 3 | 3 | 3 | 3 | 3 | 0 | 3 | 3 | 3 | 3 | 3 | 3 | 3 | 3 | 3 | 3 |
| | .28 | 0 | 0 | 0 | 0 | 0 | 0 | 0 | 0 | 0 | 0 | 0 | 0 | 0 | 0 | 1 | 2 |
| 71 | 5.6 | 3 | 3 | 3 | 3 | 3 | 0 | 3 | 3 | 3 | 3 | 3 | 3 | 3 | 3 | 3 | 3 |
| | .056 | 0 | 0 | 0 | 0 | 0 | 0 | 0 | 0 | 0 | 0 | 0 | 0 | 0 | 0 | 0 | 0 |
| | 1.12 | 1 | 2 | 3 | 2 | 3 | 0 | 2 | 2 | 2 | 3 | 3 | 2 | 2 | 3 | 3 | 3 |
| | .28 | 0 | 1 | 0 | 0 | 1 | 0 | 0 | 0 | 0 | 0 | 0 | 0 | 0 | 2 | 2 | 2 |
| 103 | .28 | 0 | 0 | 0 | 0 | 1 | 0 | 0 | 0 | 0 | 0 | 0 | 0 | 0 | 0 | 0 | 0 |
| | 1.12 | 0 | 0 | 0 | 0 | 0 | 0 | 0 | 0 | 0 | 0 | 0 | 0 | 0 | 0 | 0 | 0 |
| | 5.6 | 1 | 2 | 3 | 2 | 3 | 0 | 3 | 3 | 1 | 3 | 2 | 1 | 3 | 3 | 3 | 3 |
| 69 | 1.12 | 3 | 3 | 3 | 3 | 3 | 0 | 3 | 3 | 3 | 3 | — | 3 | 3 | 3 | 3 | 3 |
| | .28 | 0 | 3 | 3 | 3 | 3 | 0 | 3 | 3 | 2 | 3 | — | 1 | 3 | 3 | 3 | 3 |
| | .056 | 0 | 0 | 0 | 0 | 2 | 0 | 3 | 1 | 0 | 0 | — | 1 | 2 | 3 | 3 | 3 |
| | .0112 | 0 | 0 | 0 | 0 | 0 | 0 | 0 | 0 | 0 | 0 | — | 0 | 0 | 1 | 1 | 2 |
| | 5.6 | 3 | 3 | 3 | 3 | 3 | 2 | 3 | 3 | 3 | 3 | — | 3 | 3 | 3 | 3 | 3 |
| 72 | 5.6 | 3 | 3 | 3 | 3 | 3 | 0 | 3 | 3 | 3 | 3 | — | 3 | 3 | 3 | 3 | 3 |
| | 1.12 | 2 | 3 | 3 | 3 | 3 | 0 | 3 | 3 | 3 | 3 | — | 2 | 3 | 3 | 3 | 3 |
| | .28 | 0 | 1 | 3 | 2 | 3 | 0 | 3 | 3 | 2 | 3 | — | 1 | 1 | 3 | 3 | 3 |
| | .056 | 0 | 0 | 0 | 0 | 0 | 0 | 0 | 0 | 0 | 0 | — | 0 | 0 | 0 | 1 | 2 |
| | .0112 | 0 | 0 | 0 | 0 | 0 | 0 | 0 | 0 | 0 | 0 | — | 0 | 0 | 0 | 0 | 0 |
| 99 | 5.6 | 0 | 0 | 0 | 0 | 0 | 0 | 0 | 0 | 1 | 1 | 0 | 0 | 0 | 0 | 0 | 1 |
| | 1.12 | 0 | 0 | 0 | 0 | 0 | 0 | 0 | 0 | 0 | 0 | 0 | 0 | 0 | 0 | 0 | 0 |
| 81 | 5.6 | 2 | 3 | 3 | 3 | 3 | 2 | 3 | 3 | 3 | 3 | 3 | 3 | 3 | 3 | 3 | 3 |
| | 1.12 | 0 | 3 | 0 | 1 | 3 | 0 | 2 | 1 | 1 | 3 | 3 | 1 | 3 | 3 | 3 | 3 |
| | .28 | 0 | 0 | 0 | 0 | 0 | 0 | 0 | 0 | 0 | 0 | 0 | 0 | 0 | 0 | 0 | 2 |

TABLE 22-continued

| Example No. | kg/h | L | M | N | O | P | B | Q | D | R | E | F | C | J | S | K | T |
|---|---|---|---|---|---|---|---|---|---|---|---|---|---|---|---|---|---|
| | .056 | 0 | 0 | 0 | 0 | 0 | 0 | 0 | 0 | 0 | 0 | 0 | 0 | 0 | 0 | 0 | 0 |
| 42 | 1.12 | 1 | 0 | 0 | 0 | 0 | 0 | 0 | 0 | 0 | 0 | 0 | 0 | 0 | 0 | 0 | 0 |
| | 5.6 | 1 | 0 | 0 | 0 | 0 | 0 | 0 | 0 | 0 | 0 | 0 | 0 | 0 | 0 | 0 | 0 |
| 74 | .056 | 0 | 0 | 0 | 0 | 0 | 0 | 0 | 0 | 0 | 0 | 0 | 0 | 0 | 0 | 0 | 0 |
| | .28 | 0 | 0 | 0 | 0 | 0 | 0 | 0 | 0 | 0 | 0 | 0 | 0 | 0 | 0 | 0 | 1 |
| | 1.12 | 0 | 3 | 0 | 1 | 3 | — | 0 | 2 | 1 | 2 | 2 | 0 | 1 | 3 | 3 | 3 |
| | 5.6 | 1 | 3 | 3 | 3 | 3 | 0 | 3 | 3 | 2 | 3 | 3 | 2 | 3 | 3 | 3 | 3 |
| 73 | 5.6 | 2 | 3 | 3 | 3 | 3 | 2 | 3 | 3 | 3 | 3 | 3 | 3 | 3 | 3 | 3 | 3 |
| | 1.12 | 2 | 3 | 2 | 2 | 3 | 0 | 3 | 1 | 2 | 3 | 3 | 2 | 3 | 3 | 3 | 3 |
| | .28 | 0 | 1 | 1 | 1 | 2 | 0 | 0 | 0 | 0 | 1 | 0 | 0 | 0 | 0 | 2 | 3 |
| | .056 | 0 | 0 | 0 | 0 | 0 | 0 | 0 | 0 | 0 | 0 | 0 | 0 | 0 | 0 | 0 | 2 |
| 10 | .28 | 0 | 0 | 0 | 0 | 0 | 0 | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| | 1.12 | 0 | 2 | 0 | 1 | 1 | 0 | 2 | 1 | 0 | 1 | 1 | 0 | 1 | 2 | 2 | 3 |
| | 5.6 | 1 | 3 | 3 | 3 | 3 | 0 | 3 | 3 | 3 | 3 | 3 | 1 | 3 | 3 | 3 | 3 |
| 101 | .056 | 0 | 2 | 0 | 0 | 3 | 0 | 2 | 0 | 1 | 3 | 2 | 0 | 2 | 3 | 3 | 3 |
| | .28 | 0 | 3 | 2 | 0 | 3 | 0 | 3 | 2 | 3 | 3 | 3 | 3 | 3 | 3 | 3 | 3 |
| | 1.12 | 1 | 3 | 3 | 1 | 3 | 3 | 3 | 3 | 3 | 3 | 3 | 3 | 3 | 3 | 3 | 3 |
| | 5.6 | 3 | 3 | 3 | 2 | 3 | 3 | 3 | 3 | 3 | 3 | 3 | 3 | 3 | 3 | 3 | 3 |
| | .056 | 0 | 1 | 0 | 0 | 3 | 1 | 2 | 2 | 2 | 3 | 2 | 1 | 2 | 3 | 3 | 3 |
| | .0112 | 0 | 0 | 0 | 0 | 0 | 0 | 0 | 0 | 0 | 0 | 0 | 0 | 1 | 1 | 2 |
| | .28 | 1 | 3 | 2 | 0 | 3 | 1 | 3 | 1 | 3 | 3 | 3 | 2 | 3 | 3 | 3 | 3 |
| | .056 | 0 | 2 | 0 | 0 | 3 | 0 | 1 | 0 | 0 | 0 | 2 | 1 | 2 | 3 | 3 |
| 25 | .0112 | 0 | 0 | 0 | 0 | 0 | 0 | 0 | 0 | 0 | 0 | 0 | 0 | 0 | 0 | 0 | 0 |
| | 5.6 | 3 | 3 | 3 | 3 | 3 | 3 | 3 | 3 | 3 | 3 | 3 | 3 | 3 | 3 | 3 | 3 |
| | 1.12 | 3 | 3 | 3 | 3 | 3 | 2 | 3 | 3 | 3 | 3 | 3 | 3 | 3 | 3 | 3 | 3 |
| | .28 | 0 | 3 | 3 | 2 | 3 | 0 | 3 | 1 | 2 | 3 | 3 | 3 | 3 | 3 | 3 | 3 |
| | .056 | 0 | 2 | 1 | 0 | 1 | 0 | 0 | 0 | 0 | 0 | 0 | 1 | 2 | 3 | 3 |
| 102 | 5.6 | 1 | 2 | 0 | 0 | 0 | 0 | 0 | 0 | 0 | 2 | 2 | 1 | 1 | 1 | 1 | 3 |
| | 1.12 | 0 | 0 | 0 | 0 | 0 | 0 | 0 | 0 | 0 | 0 | 0 | 0 | 0 | 0 | 0 | 2 |
| | .28 | 0 | 0 | 0 | 0 | 0 | 0 | 0 | 0 | 0 | 0 | 0 | 0 | 0 | 0 | 0 | 0 |
| 134 | 5.6 | 3 | 3 | 3 | 3 | 3 | 3 | 3 | 3 | 3 | 3 | 3 | 3 | 3 | 3 | 3 | 3 |
| | 1.12 | 1 | 2 | 2 | 2 | 3 | 2 | 2 | 2 | 2 | 2 | 2 | 1 | 3 | 3 | 3 | 3 |
| | .28 | 1 | 0 | 0 | 0 | 1 | 0 | 0 | 0 | 0 | 0 | 0 | 0 | 0 | 0 | 0 | 2 |
| | .0112 | 0 | 0 | 0 | 0 | 0 | — | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| 130 | 5.6 | 0 | 0 | 0 | 3 | 3 | 0 | 2 | 1 | 1 | 3 | 2 | 0 | 0 | 1 | 1 | 3 |
| | 1.12 | 0 | 0 | 0 | 0 | 0 | 0 | 0 | 0 | 1 | 0 | 0 | 0 | 0 | 0 | 0 | 2 |
| | .28 | 0 | 0 | 0 | 0 | 0 | 0 | 0 | 0 | 0 | 0 | 0 | 0 | 0 | 1 | 1 |
| 104 | .28 | 0 | 0 | 0 | 0 | 2 | 0 | 0 | 0 | 0 | 1 | 0 | 0 | 0 | 0 | 0 | 1 |
| | 5.6 | 1 | 3 | 3 | 3 | 3 | 1 | 3 | 3 | 3 | 3 | 3 | 3 | 3 | 3 | 3 | 3 |
| | 1.12 | 0 | 2 | 0 | 1 | 3 | 0 | 2 | 2 | 1 | 2 | 1 | 1 | 2 | 2 | 2 | 2 |
| 127 | .28 | 0 | 0 | 0 | 0 | 0 | 0 | 0 | 0 | 0 | 0 | 0 | 0 | 0 | 0 | 0 | 0 |
| | 1.12 | 0 | 1 | 0 | 0 | 0 | 0 | 0 | 0 | 0 | 0 | 0 | 0 | 0 | 1 | 2 | 1 |
| | 5.6 | 0 | 3 | 1 | 1 | 3 | 0 | 1 | 2 | 2 | 3 | 2 | 3 | 2 | 3 | 3 | 3 |
| 129 | 5.6 | 2 | 3 | 2 | 3 | 3 | 0 | 3 | 3 | 3 | 3 | 3 | 3 | 3 | 3 | 3 | 3 |
| | .056 | 0 | 0 | 0 | 0 | 0 | 0 | 0 | 0 | 0 | 0 | 0 | 0 | 0 | 0 | 0 | 0 |
| | 1.12 | 0 | 2 | 0 | 2 | 3 | — | 0 | 0 | 2 | 3 | 3 | 3 | 1 | 3 | 3 | 3 |
| | .28 | 0 | 0 | 0 | 0 | 1 | 0 | 0 | 0 | 0 | 0 | 0 | 0 | 0 | 0 | 1 | 1 |
| 131 | .056 | 0 | 0 | 0 | 0 | 3 | 0 | 0 | 0 | 0 | 2 | 2 | 1 | 0 | 3 | 3 | 3 |
| | 5.6 | 3 | 3 | 3 | 3 | 3 | 1 | 3 | 3 | 3 | 3 | 3 | 3 | 3 | 3 | 3 | 3 |
| | 1.12 | 2 | 3 | 3 | 0 | 3 | — | 3 | 3 | 3 | 3 | 3 | 3 | 3 | 3 | 3 | 3 |
| | .28 | 0 | 3 | 1 | 0 | 3 | 0 | 3 | 3 | 3 | 3 | 3 | 3 | 3 | 3 | 3 | 3 |
| | .0112 | 0 | 0 | 0 | 0 | 0 | — | 0 | 0 | 0 | 0 | 0 | 0 | 0 | 0 | 0 | 0 |
| 133 | 5.6 | 3 | 3 | 3 | 3 | 3 | 3 | 3 | 3 | 3 | 3 | 3 | 3 | 3 | 3 | 3 | 3 |
| | 1.12 | 2 | 3 | 3 | 2 | 3 | 0 | 3 | 3 | 3 | 3 | 3 | 3 | 3 | 3 | 3 | 3 |
| | .28 | 2 | 3 | 0 | 0 | 3 | 1 | 3 | 3 | 3 | 3 | 3 | 3 | 3 | 3 | 3 | 3 |
| | .056 | 0 | 2 | 0 | 0 | 3 | 0 | 2 | 1 | 1 | 1 | 1 | 2 | 1 | 3 | 3 | 3 |
| | .0112 | 0 | 0 | 0 | 0 | 0 | 0 | 0 | 0 | 0 | 0 | 0 | 0 | 0 | 0 | 1 | 2 |
| 80 | .0112 | 0 | 0 | 0 | 0 | 0 | 0 | 0 | 0 | 0 | 0 | 0 | 0 | 0 | 0 | 0 | 2 |
| | 5.6 | 3 | 3 | 3 | 3 | 3 | 3 | 3 | 3 | 3 | 3 | 3 | 3 | 3 | 3 | 3 | 3 |
| | .056 | 0 | 1 | 0 | 0 | 2 | 0 | 0 | 0 | 2 | 1 | 0 | 0 | 1 | 1 | 3 |
| | .28 | 1 | 3 | 3 | 3 | 3 | 3 | 3 | 3 | 3 | 3 | 3 | 2 | 3 | 3 | 3 | 3 |
| | 1.12 | 2 | 3 | 3 | 3 | 3 | 3 | 3 | 3 | 3 | 3 | 3 | 3 | 3 | 3 | 3 | 3 |
| 26 | 5.6 | 3 | 3 | 3 | 3 | 3 | 0 | 3 | 3 | 3 | 3 | 3 | 3 | 3 | 3 | 3 | 3 |
| | 1.12 | 1 | 2 | 2 | 2 | 3 | 0 | 3 | 2 | 1 | 1 | 0 | 1 | 3 | 3 | 3 | 3 |
| | .28 | 0 | 2 | 0 | 0 | 0 | 0 | 0 | 0 | 0 | 0 | 0 | 2 | 2 | 3 | 1 |
| | .056 | 0 | 0 | 0 | 0 | 0 | 0 | 0 | 0 | 0 | 0 | 0 | 0 | 0 | 0 | 0 | 0 |
| 27 | 5.6 | 2 | 3 | 3 | 3 | 3 | 0 | 3 | 1 | 2 | 3 | 2 | 1 | 3 | 3 | 3 | 3 |
| | 1.12 | 1 | 0 | 0 | 0 | 3 | 0 | 1 | 0 | 0 | 1 | 0 | 1 | 2 | 1 | 2 | 3 |
| | .28 | 0 | 0 | 0 | 0 | 0 | 0 | 0 | 0 | 0 | 0 | 0 | 0 | 0 | 0 | 0 |
| 123 | .056 | 0 | 0 | 0 | 0 | 0 | 0 | 0 | 0 | 0 | 0 | 0 | 0 | 0 | 0 | 0 | 0 |
| | .0112 | 0 | 0 | 0 | 0 | 0 | — | 0 | 0 | 0 | 0 | 0 | 0 | 0 | 0 | 0 | 0 |
| | 1.12 | 0 | 3 | 3 | 3 | 3 | 0 | 3 | 1 | 2 | 3 | 3 | 3 | 3 | 3 | 3 | 3 |
| | .28 | 0 | 2 | 1 | 0 | 3 | 0 | 2 | 0 | 1 | 2 | 1 | 1 | 3 | 3 | 3 | 3 |
| | 5.6 | 3 | 3 | 3 | 3 | 3 | 3 | 3 | 3 | 3 | 3 | 3 | 3 | 3 | 3 | 3 | 3 |
| 124 | .28 | 0 | 0 | 0 | 0 | 0 | 0 | 0 | 0 | 0 | 0 | 0 | 0 | 0 | 2 | 3 | 3 |
| | .056 | 0 | 0 | 0 | 0 | 0 | — | 0 | 0 | 0 | 0 | 0 | 0 | 0 | 0 | 0 | 1 |
| | 1.12 | 0 | 1 | 3 | 2 | 3 | 0 | 2 | 2 | 2 | 2 | 1 | 1 | 3 | 3 | 3 | 3 |
| | 5.6 | 1 | 2 | 3 | 3 | 3 | 0 | 3 | 2 | 2 | 3 | 3 | 3 | 3 | 3 | 3 | 3 |
| 109 | 1.12 | 0 | 0 | 0 | 0 | 0 | 0 | 3 | 0 | 0 | 0 | 0 | 0 | 0 | 0 | 0 | 0 |

TABLE 22-continued

| Example No. | kg/h | L | M | N | O | P | B | Q | D | R | E | F | C | J | S | K | T |
|---|---|---|---|---|---|---|---|---|---|---|---|---|---|---|---|---|---|
| | 5.6 | 0 | 0 | 0 | 0 | 0 | — | 1 | 0 | 0 | 0 | 0 | 0 | 1 | 2 | 2 | 3 |
| 110 | .28 | 0 | 1 | 0 | 0 | 2 | 0 | 1 | 0 | 0 | 1 | 0 | 0 | 3 | 2 | 1 | 1 |
| | 1.12 | 0 | 3 | 2 | 3 | 3 | 0 | 3 | 0 | 1 | 3 | 2 | 0 | 3 | 3 | 3 | 3 |
| | 5.6 | 0 | 3 | 3 | 3 | 3 | 0 | 3 | 3 | 3 | 3 | 3 | 3 | 3 | 3 | 3 | 3 |
| | .056 | 0 | 0 | 0 | 0 | 0 | 0 | 0 | 0 | 0 | 0 | 0 | 0 | 0 | 0 | 0 | 0 |
| 111 | 1.12 | 1 | 3 | 3 | 3 | 3 | 0 | 3 | 3 | 3 | 3 | 3 | 3 | 3 | 3 | 3 | 3 |
| | .28 | 1 | 2 | 3 | 3 | 3 | 0 | 2 | 0 | 1 | 1 | 1 | 1 | 3 | 3 | 3 | 3 |
| | 5.6 | 3 | 3 | 3 | 3 | 3 | 3 | 3 | 3 | 3 | 3 | 3 | 3 | 3 | 3 | 3 | 3 |
| | .056 | 1 | 0 | 0 | 0 | 0 | 0 | 0 | 0 | 0 | 0 | 0 | 0 | 0 | 0 | 0 | 2 |
| | .0112 | 0 | 0 | 0 | 0 | 0 | — | 0 | 0 | 0 | 0 | 0 | 0 | 0 | 0 | 0 | 0 |
| 122 | 5.6 | 3 | 3 | 3 | 3 | 3 | 1 | 3 | 3 | 3 | 3 | 3 | 3 | 3 | 3 | 3 | 3 |
| | .0112 | 0 | 0 | 0 | 0 | 0 | 0 | 0 | 0 | 0 | 0 | 0 | 0 | 0 | 0 | 0 | 0 |
| | 1.12 | 1 | 3 | 2 | 2 | 3 | 0 | 3 | 2 | 2 | 3 | 3 | 3 | 3 | 3 | 3 | 3 |
| | .28 | 0 | 2 | 0 | 0 | 2 | 0 | 1 | 0 | 0 | 1 | 1 | 1 | 2 | 2 | 2 | 3 |
| | .056 | 0 | 0 | 0 | 0 | 1 | 0 | 0 | 0 | 0 | 0 | 0 | 0 | 0 | 0 | 0 | 0 |
| 117 | .0112 | 0 | 0 | 0 | 0 | 0 | 0 | 0 | 0 | 0 | 0 | 0 | 0 | 0 | 0 | 0 | 0 |
| | 5.6 | 3 | 3 | 3 | 3 | 3 | 3 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | .28 | 1 | 3 | 2 | 3 | 3 | 0 | 3 | 2 | 3 | 3 | 3 | 2 | 3 | 3 | 3 | 3 |
| | .056 | 0 | 2 | 0 | 0 | 3 | 0 | 3 | 0 | 1 | 1 | 1 | 0 | 3 | 3 | 3 | 3 |
| 113 | .056 | 0 | 0 | 0 | 0 | 0 | 0 | 0 | 0 | 0 | 0 | 0 | 0 | 0 | 0 | 0 | 0 |
| | .28 | 0 | 0 | 0 | 0 | 0 | 0 | 0 | 0 | 0 | 0 | 0 | 0 | 0 | 1 | 1 | 2 |
| | 1.12 | 0 | 3 | 2 | 0 | 3 | 0 | 3 | 1 | 2 | 3 | 3 | 2 | 3 | 3 | 3 | 3 |
| | 5.6 | 0 | 3 | 3 | 3 | 3 | 0 | 3 | 3 | 3 | 3 | 3 | 3 | 3 | 3 | 3 | 3 |
| 125 | .056 | 0 | 0 | 0 | 0 | 0 | 0 | 0 | 0 | 0 | 0 | 0 | 0 | 0 | 0 | 0 | 0 |
| | .0112 | 0 | 0 | 0 | 0 | 0 | 0 | 0 | 0 | 0 | 0 | 0 | 0 | 0 | 0 | 0 | 0 |
| | 5.6 | 3 | 3 | 3 | 3 | 3 | 0 | 3 | 3 | 3 | 3 | 3 | 3 | 3 | 3 | 3 | 3 |
| | 1.12 | 0 | 2 | 2 | 3 | 3 | 2 | 3 | 3 | 3 | 3 | 3 | 2 | 3 | 3 | 3 | 3 |
| | .28 | 0 | 2 | 0 | 0 | 3 | 0 | 2 | 0 | 1 | 2 | 2 | 1 | 3 | 3 | 3 | 3 |
| 152 | 5.6 | 1 | 2 | 0 | 2 | 3 | 0 | 0 | 0 | 1 | 2 | 2 | 0 | 3 | 3 | 3 | 3 |
| | 1.12 | 0 | 0 | 0 | 0 | 0 | 0 | 0 | 0 | 0 | 0 | 0 | 0 | N | 2 | 3 | 3 |
| | 0.28 | 0 | 0 | 0 | 0 | 0 | 0 | 0 | 0 | 0 | 0 | 0 | 0 | N | 0 | 0 | 0 |
| 153 | 5.6 | 0 | 2 | 1 | 0 | 1 | 0 | 1 | 1 | 1 | 2 | 2 | 1 | 1 | 2 | 3 | 3 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 156' | 5.6 | 1 | 2 | 0 | 0 | 0 | 0 | 1 | 1 | 2 | 2 | 0 | 0 | 0 | 1 | 3 |
| | 1.12 | 1 | 1 | 0 | 0 | 0 | 0 | 0 | 0 | 2 | 2 | 0 | 0 | 0 | 1 | 2 |
| 157 | 5.6 | 0 | 2 | 0 | 0 | 0 | 0 | 0 | 0 | 3 | 3 | 0 | 0 | 2 | 3 | 3 |
| | 1.12 | 0 | 3 | 0 | N | 0 | 0 | 0 | 1 | 2 | 3 | 3 | 0 | 0 | 2 | 3 | 3 |
| | 0.28 | 0 | 2 | 0 | 0 | 0 | 0 | 0 | 0 | 3 | 2 | 0 | 0 | 0 | 1 | 2 |
| 158 | 5.6 | 0 | 0 | 0 | 0 | 0 | 0 | 0 | 0 | 0 | 0 | 0 | 0 | 0 | 0 | 0 | 0 |
| | 1.12 | 0 | 0 | 0 | 0 | 0 | 0 | 0 | 0 | 0 | 0 | 0 | 0 | 0 | 0 | 0 | 0 |
| 159 | 5.6 | 0 | 2 | 3 | 3 | 3 | 0 | 3 | 2 | 2 | 3 | 3 | 3 | 3 | 3 | 3 | 3 |
| | 1.12 | 0 | 2 | 0 | 1 | 3 | 0 | 2 | 1 | 0 | 0 | 0 | 0 | 2 | 3 | 3 | 3 |
| | 0.28 | 0 | 0 | 0 | 0 | 0 | 0 | 0 | 0 | 0 | 0 | 0 | 0 | 0 | 0 | 0 | 2 |
| 161 | 5.6 | 0 | 3 | 3 | 2 | 3 | 0 | 3 | 3 | 3 | 3 | 3 | 3 | 3 | 3 | 3 | 3 |
| | 1.12 | 1 | 3 | 0 | 1 | 3 | 0 | 2 | 2 | 2 | 3 | 3 | 2 | 3 | 3 | 3 | 3 |
| | 0.28 | 0 | 0 | 0 | 0 | 0 | 0 | 0 | 1 | 1 | 1 | 1 | 1 | 1 | 2 | 3 |
| | .056 | 0 | 0 | 0 | 0 | 0 | 0 | 0 | 0 | 0 | 0 | 0 | 0 | 0 | 0 | 0 | 0 |
| 162 | 5.6 | 1 | 3 | 3 | 3 | 3 | 0 | 2 | 3 | 3 | 3 | 3 | 3 | 3 | 3 | 3 | 3 |
| | 1.12 | 0 | 2 | 0 | 2 | 2 | 1 | 2 | 2 | 1 | 2 | 2 | 1 | 2 | 3 | 3 | 3 |
| | 0.28 | 0 | 0 | 0 | 0 | 0 | 0 | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| 163 | 5.6 | 3 | 3 | 3 | 3 | 3 | 0 | 3 | 3 | 3 | 3 | 3 | 3 | 3 | 3 | 3 | 3 |
| | 1.12 | 0 | 2 | 3 | 1 | 3 | 0 | 2 | 1 | 2 | 3 | 3 | 3 | 3 | 3 | 3 | 3 |
| | 0.28 | 0 | 0 | 2 | 0 | 1 | 0 | 0 | 0 | 1 | 1 | 1 | 0 | 0 | 1 | 1 | 2 |
| | .056 | 0 | 0 | 0 | 0 | 0 | 0 | 0 | 0 | 0 | 0 | 0 | 0 | 0 | 0 | 1 | 1 |
| | 0.0112 | 0 | 0 | 0 | 0 | 0 | 0 | 0 | 0 | 0 | 0 | 0 | 0 | 0 | 0 | 0 | 0 |
| 164 | 5.6 | 0 | 3 | 1 | 0 | 3 | 1 | 3 | 2 | 2 | 2 | 2 | 2 | 3 | 2 | 3 | 3 |
| | 1.12 | 1 | 2 | 0 | 0 | 0 | 0 | 0 | 0 | 2 | 2 | 2 | 1 | 2 | 0 | 0 |
| | 0.28 | 0 | 0 | 0 | 0 | 0 | 0 | 0 | 0 | 0 | 0 | 0 | 0 | 0 | 0 | 0 | 0 |
| 165 | 5.6 | 0 | 0 | 0 | 0 | 2 | 0 | 0 | 1 | 0 | 0 | 0 | 1 | 0 | 3 | 3 | 3 |
| | 1.12 | 0 | 0 | 0 | 0 | 0 | 0 | 0 | 0 | 0 | 0 | 0 | 0 | 0 | 2 | 1 | 2 |
| | 0.28 | 0 | 0 | 0 | 0 | 0 | 0 | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| 166 | 5.6 | 3 | 3 | 3 | 3 | 3 | 0 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | 0.28 | 0 | 2 | 2 | 2 | 3 | 0 | 3 | 2 | 2 | 3 | 3 | 2 | 3 | 3 | 3 | 3 |
| | .056 | 0 | 0 | 0 | 0 | 0 | 0 | 0 | 0 | 0 | 0 | 0 | 0 | 0 | 2 | 3 | 3 |
| | 0.0112 | 0 | 0 | 0 | 0 | 0 | 0 | 0 | 0 | 0 | 0 | 0 | 0 | 0 | 0 | 0 | 0 |
| 167 | 5.6 | 0 | 2 | 2 | 3 | 3 | 0 | 2 | 3 | 3 | 3 | 3 | 2 | 3 | 3 | 3 | 3 |
| | 1.12 | 0 | 0 | 0 | 1 | 1 | 0 | 2 | 1 | 2 | 2 | 1 | .1 | N | 1 | 1 | 2 |
| | 0.28 | 0 | 0 | 0 | 0 | 0 | 0 | 0 | 0 | 0 | 0 | 0 | 0 | N | 0 | 0 | 0 |
| 169 | 5.6 | 0 | 3 | 3 | 3 | 3 | 0 | 1 | 2 | 3 | 3 | 3 | 3 | 3 | 3 | 3 | 3 |
| | 1.12 | 0 | 2 | 0 | 0 | 3 | 0 | 2 | 1 | 0 | 2 | 2 | 0 | 3 | 3 | 3 | 3 |
| | 0.28 | 0 | 0 | 0 | 0 | 0 | 0 | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 170 | 5.6 | 2 | 3 | 3 | 3 | 3 | 0 | 3 | 3 | 3 | 3 | 3 | 3 | 3 | 3 | 3 | 3 |
| | 1.12 | 0 | 3 | 3 | 3 | 2 | 0 | 2 | 0 | 1 | 3 | 3 | 3 | 2 | 3 | 3 |
| | 0.28 | 0 | 0 | 0 | 0 | 2 | 0 | 0 | 0 | 0 | 2 | 1 | 1 | 1 | 2 | 2 | 3 |

TABLE 22-continued

| Example No. | kg/h | L | M | N | O | P | B | Q | D | R | E | F | C | J | S | K | T |
|---|---|---|---|---|---|---|---|---|---|---|---|---|---|---|---|---|---|
| | .056 | 0 | 0 | 0 | 0 | 0 | 0 | 0 | 0 | 0 | 0 | 0 | 0 | 0 | 0 | 0 | 2 |
| | 0.0112 | 0 | 0 | 0 | 0 | 0 | 0 | 0 | 0 | 0 | 0 | 0 | 0 | 0 | 0 | 0 | 0 |
| 171 | 5.6 | 3 | 3 | 3 | 3 | 3 | 0 | 3 | 3 | 3 | 3 | 3 | 3 | 3 | 3 | 3 | 3 |
| | 1.12 | 0 | 3 | 3 | 2 | 3 | 0 | 3 | 3 | 3 | 3 | 3 | 3 | 3 | 3 | 3 | 3 |
| | 0.28 | 0 | 2 | 0 | 0 | 3 | 0 | 0 | 1 | 0 | 0 | 0 | 0 | 3 | 3 | 3 | 3 |
| | .056 | 0 | 1 | 0 | 0 | 1 | 0 | 0 | 0 | 0 | 0 | 0 | 0 | 0 | 1 | 2 | 0 |
| | 0.0112 | 0 | 0 | 0 | 0 | 0 | 0 | 0 | 0 | 0 | 0 | 0 | 0 | 0 | 0 | 0 | 0 |
| 172 | 5.6 | 3 | 3 | 3 | 3 | 3 | 0 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | 0.28 | 0 | 3 | 3 | 3 | 3 | 0 | 1 | 2 | 1 | 3 | 3 | 2 | 3 | 3 | 3 | 3 |
| | .056 | 0 | 1 | 1 | 0 | 3 | 0 | 0 | 0 | 0 | 0 | 0 | 0 | 0 | 3 | 3 | 3 |
| | 0.0112 | 0 | 0 | 0 | 0 | 1 | 0 | 0 | 0 | 0 | 0 | 0 | 0 | 0 | 0 | 1 | 0 |
| 173 | 5.6 | 3 | 3 | 3 | 3 | 3 | 0 | 3 | 3 | 3 | 3 | 3 | 3 | 3 | 3 | 3 | 3 |
| | 1.12 | 2 | 3 | 3 | 3 | 3 | 0 | 3 | 3 | 3 | 3 | 3 | 3 | 3 | 3 | 3 | 3 |
| | 0.28 | 0 | 2 | 1 | 0 | 3 | 0 | 2 | 0 | 0 | 1 | 1 | 0 | 3 | 3 | 3 | 3 |
| | .056 | 0 | 1 | 0 | 0 | 0 | 0 | 0 | 0 | 0 | 0 | 0 | 0 | 0 | 1 | 3 | 3 |
| | 0.0112 | 0 | 0 | 0 | 0 | 0 | 0 | 0 | 0 | 0 | 0 | 0 | 0 | 0 | 0 | 0 | 0 |
| 174 | 5.6 | 1 | 3 | 3 | 3 | 3 | 0 | 3 | 3 | 3 | 3 | 3 | 3 | 3 | 3 | 3 | 3 |
| | 1.12 | 0 | 0 | 0 | 0 | 3 | 0 | 0 | 0 | 0 | 0 | 0 | 0 | 1 | 2 | 3 | 3 |
| | 0.28 | 0 | 0 | 0 | 0 | 0 | 0 | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| 175 | 5.6 | 0 | 3 | 2 | 1 | 3 | 0 | 3 | 3 | 1 | 3 | 2 | 2 | 3 | 3 | 3 | 3 |
| | 1.12 | 0 | 2 | 0 | 0 | 1 | 0 | 2 | 0 | 0 | 2 | 0 | 0 | 3 | 2 | 3 | 3 |
| | 0.28 | 0 | 0 | 0 | 0 | 0 | 0 | 0 | 0 | 0 | 0 | 0 | 0 | 0 | 0 | 0 | 0 |
| | .056 | 0 | 0 | 0 | 0 | 0 | 0 | 0 | 0 | 0 | 0 | 0 | 0 | 0 | 0 | 0 | 0 |
| 176 | 5.6 | 0 | 3 | 3 | 0 | 3 | 0 | 3 | 3 | 1 | 3 | 3 | 2 | 3 | 3 | 3 | 3 |
| | 1.12 | 0 | 1 | 0 | 0 | 3 | 0 | 0 | 0 | 0 | 0 | 0 | 0 | 3 | 3 | 3 | 1 |
| | 0.28 | 0 | 0 | 0 | 0 | 0 | 0 | 0 | 0 | 0 | 0 | 0 | 0 | 0 | 0 | 0 | 0 |
| 177 | 5.6 | 1 | 3 | 3 | 3 | 3 | 0 | 3 | 3 | 3 | 3 | 3 | 2 | 3 | 3 | 3 | 3 |
| | 1.12 | 0 | 1 | 1 | 1 | 0 | 0 | 0 | 0 | 0 | 2 | 1 | 1 | 2 | 2 | 2 | 2 |
| | 0.28 | 0 | 1 | 0 | 0 | 0 | 0 | 0 | 0 | 0 | 2 | 1 | 0 | 0 | 0 | 1 | 1 |
| | .056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 178 | 5.6 | 3 | 3 | 3 | 3 | 3 | 1 | 3 | 3 | 3 | 3 | 3 | 3 | 3 | 3 | 3 | 3 |
| | 1.12 | 1 | 3 | 3 | 2 | 3 | 0 | 3 | 2 | 2 | 3 | 2 | 2 | 3 | 3 | 3 | 3 |
| | 0.28 | 0 | 2 | 1 | 1 | 3 | 0 | 1 | 0 | 1 | 1 | 0 | 0 | 1 | 2 | 3 | 3 |
| | .056 | 0 | 0 | 0 | 0 | 0 | 0 | 0 | 0 | 0 | 0 | 0 | 0 | 0 | 0 | 0 | 0 |
| 179 | 5.6 | 0 | 3 | 3 | 2 | 3 | 0 | 3 | 1 | 2 | 3 | 3 | 2 | 3 | 3 | 3 | 3 |
| | 1.12 | 0 | 0 | 0 | 0 | 2 | 0 | 3 | 0 | 0 | 0 | 0 | 3 | 3 | 3 | 3 | 3 |
| | 0.28 | 0 | 0 | 0 | 0 | 0 | 0 | 0 | 0 | 0 | 0 | 0 | 0 | 0 | 0 | 0 | 0 |
| 180 | 5.6 | 2 | 3 | 3 | 3 | 3 | 0 | 3 | 3 | 3 | 3 | 3 | 3 | 3 | 3 | 3 | 3 |
| | 1.12 | 0 | 3 | 1 | 2 | 3 | 0 | 3 | 0 | 2 | 2 | 2 | 1 | 3 | 3 | 3 | 3 |
| | 0.28 | 0 | 1 | 0 | 0 | 2 | 0 | 0 | 0 | 1 | 2 | 0 | 1 | 2 | 1 | 3 | 3 |
| | .056 | 0 | 0 | 0 | 0 | 0 | 0 | 0 | 0 | 0 | 0 | 0 | 0 | 0 | 0 | 0 | 0 |
| 181 | 5.6 | 0 | 0 | 0 | 0 | 1 | 0 | 0 | 0 | 0 | 0 | 0 | 0 | 0 | 0 | 3 | 2 |
| | 1.12 | 0 | 0 | 0 | 0 | 0 | 0 | 0 | 0 | 0 | 0 | 0 | 0 | 0 | 0 | 0 | 0 |
| 182 | 5.6 | 0 | 0 | 0 | 0 | 0 | 0 | 0 | 0 | 1 | 0 | 0 | 0 | 0 | 0 | 0 | 0 |
| | 1.12 | 0 | 0 | 0 | 0 | 0 | 0 | 0 | 0 | 0 | 0 | 0 | 0 | 0 | 0 | 0 | 0 |
| 184 | 5.6 | 1 | 3 | 3 | 1 | 3 | 1 | 3 | 2 | 2 | 3 | 3 | 3 | 3 | 3 | 2 | 3 |
| | 1.12 | 0 | 0 | 1 | 0 | 0 | 0 | 0 | 0 | 0 | 2 | 2 | 1 | 0 | 1 | 2 | 3 |
| | 0.28 | 0 | 0 | 0 | 0 | 0 | 0 | 0 | 0 | 0 | 0 | 0 | 0 | 0 | 0 | 1 | 1 |
| | .056 | 0 | 0 | 0 | 0 | 0 | 0 | 0 | 0 | 0 | 0 | 0 | 0 | 0 | 0 | 0 | 0 |
| 186 | 5.6 | 1 | 3 | 3 | 2 | 3 | 1 | 2 | 2 | 2 | 3 | 3 | 3 | 3 | 3 | 3 | 3 |
| | 1.12 | 0 | 2 | 0 | 0 | 0 | 0 | 0 | 0 | 2 | 1 | 1 | 0 | 2 | 2 | 2 | 3 |
| | 0.28 | 0 | 1 | 0 | 0 | 0 | N | 1 | 0 | 0 | 0 | 0 | 2 | 2 | 1 | 2 | 2 |
| | .056 | 0 | 0 | 0 | 0 | 0 | 0 | 0 | 0 | 1 | 1 | 0 | 0 | 0 | 0 | 0 | 0 |
| 187 | 5.6 | 0 | 0 | 0 | 0 | 0 | 0 | 0 | 0 | 0 | 0 | 0 | 0 | 0 | 0 | 0 | 1 |
| | 1.12 | 0 | 0 | 0 | 0 | 0 | 0 | 0 | 0 | 0 | 0 | 0 | 0 | 0 | 0 | 0 | 0 |
| 189 | 5.6 | 1 | 2 | 3 | 1 | 3 | 0 | 3 | 1 | 2 | 3 | 3 | 2 | 3 | 3 | 3 | 3 |
| | 1.12 | 0 | 0 | 0 | 0 | 0 | 0 | 0 | 0 | 1 | 0 | 0 | 0 | 1 | 2 | 3 | 3 |
| 190 | 5.6 | 3 | 3 | 3 | 3 | 3 | 0 | 3 | 3 | 3 | 3 | 3 | 3 | 3 | 3 | 3 | 3 |
| | 1.12 | 2 | 2 | 3 | 1 | 3 | 0 | 2 | 2 | 2 | 3 | 2 | 1 | 3 | 3 | 3 | 3 |
| | 0.28 | 2 | 3 | 3 | 1 | 1 | 0 | 2 | 2 | 2 | 2 | 2 | 1 | 1 | 3 | 3 | 3 |
| | .056 | 0 | 1 | 0 | 0 | 0 | 0 | 0 | 0 | 2 | 2 | 1 | 1 | 1 | 0 | 0 | 2 |
| | 0.0112 | 0 | 0 | 0 | 0 | 0 | 0 | 0 | 0 | 0 | 0 | 0 | 0 | 0 | 0 | 0 | 0 |
| 191 | 5.6 | 0 | 2 | 1 | 1 | 2 | 0 | 1 | 0 | 2 | 3 | 3 | 2 | 2 | 3 | 3 | 3 |
| | 1.12 | 1 | 1 | 0 | 0 | 0 | N | 0 | 1 | 2 | 2 | 2 | N | 1 | 1 | 2 | 3 |
| | 0.28 | 0 | 0 | 0 | 0 | 0 | 0 | 0 | 0 | 0 | 0 | 0 | 0 | 0 | 0 | 0 | 0 |
| 192 | 5.6 | 0 | 1 | 0 | 0 | 0 | N | 0 | 0 | 0 | 0 | 0 | 0 | 0 | 1 | 3 | 3 |
| | 1.12 | 0 | 0 | 0 | 0 | 0 | N | 0 | 0 | 0 | 0 | 0 | 0 | 0 | 0 | 0 | 0 |
| 198 | 5.6 | 3 | 3 | 3 | 3 | 3 | 3 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | 0.28 | 3 | 3 | 3 | 3 | 3 | 0 | 3 | 3 | 3 | 3 | 3 | 3 | 3 | 3 | 3 | 3 |
| | .056 | 1 | 2 | 2 | 3 | 3 | 0 | 3 | 3 | 3 | 3 | 2 | 2 | 3 | 3 | 3 | 3 |
| | .056 | 0 | 3 | 2 | 3 | 3 | N | 3 | 2 | 2 | 3 | 3 | 2 | 3 | 3 | 3 | 3 |
| | 0.0112 | 0 | 0 | 0 | 0 | 1 | 0 | 0 | 0 | 1 | 2 | 1 | 2 | 1 | 2 | 2 | 3 |
| | 0.0112 | 0 | 0 | 0 | 0 | 1 | N | 1 | 0 | 0 | 0 | 1 | 0 | 0 | 0 | 1 | 2 |
| | .0056 | 0 | 0 | 0 | 0 | 0 | N | 0 | 0 | 1 | 1 | 1 | 0 | 0 | 1 | 1 | 2 |
| 199 | 5.6 | 3 | 3 | 3 | 3 | 3 | 2 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | 0.28 | 2 | 3 | 3 | 3 | 3 | 0 | 3 | 3 | 3 | 3 | 3 | 3 | 3 | 3 | 3 | 3 |

TABLE 22-continued

| Example No. | kg/h | L | M | N | O | P | B | Q | D | R | E | F | C | J | S | K | T |
|---|---|---|---|---|---|---|---|---|---|---|---|---|---|---|---|---|---|
| | .056 | 1 | 2 | 1 | 2 | 3 | 0 | 2 | 1 | 2 | 3 | 2 | 1 | 3 | 3 | 3 | 3 |
| | .056 | 0 | 3 | 1 | 2 | 3 | N | 2 | 2 | 3 | 3 | 3 | 1 | 3 | 3 | 3 | 3 |
| | 0.0112 | 0 | 0 | 1 | 1 | 3 | 0 | 1 | 0 | 0 | 0 | 0 | 1 | 3 | 3 | 3 | 3 |
| | 0.0112 | 0 | 0 | 0 | 0 | 2 | N | 2 | 0 | 0 | 0 | 0 | 0 | 1 | 0 | 2 | 2 |
| | .0056 | 0 | 0 | 0 | 0 | 0 | N | 0 | 0 | 0 | 0 | 0 | 0 | 0 | 0 | 1 | 1 |
| 200 | 5.6 | 2 | 3 | 2 | 1 | 3 | 0 | 3 | 3 | 3 | 3 | 3 | 3 | 3 | 3 | 3 | 3 |
| | 1.12 | 0 | 2 | 0 | 0 | 0 | N | 3 | 1 | 2 | 3 | 3 | 1 | 1 | 2 | 3 | 3 |
| | 0.28 | 0 | 2 | 0 | 0 | 0 | 0 | 1 | 0 | 0 | 1 | 1 | 0 | 1 | 2 | 2 | 3 |
| | .056 | 0 | 0 | 0 | 0 | 0 | 0 | 0 | 0 | 0 | 0 | 0 | 0 | 0 | 0 | 0 | 0 |
| 204 | 5.6 | 0 | 0 | 0 | 0 | 0 | 0 | 0 | 0 | 0 | 0 | 0 | 0 | 3 | 3 | 3 | 3 |
| | 1.12 | 0 | 0 | 0 | 0 | 0 | 0 | 0 | 0 | 0 | 0 | 0 | 0 | N | 0 | 0 | 2 |
| 208 | 5.6 | 3 | 3 | 3 | 3 | 3 | 0 | 3 | 3 | 3 | 3 | 3 | 3 | 3 | 3 | 3 | 3 |
| | 1.12 | 1 | 3 | 3 | 3 | 3 | 0 | 3 | 3 | 2 | 3 | 3 | 3 | 3 | 3 | 3 | 3 |
| | 0.28 | 0 | 1 | 0 | 1 | 3 | 0 | 0 | 0 | 0 | 1 | 1 | 1 | 3 | 3 | 3 | 3 |
| | .056 | 0 | 0 | 0 | 0 | 0 | 0 | 0 | 0 | 0 | 0 | 0 | 0 | N | 1 | 2 | 3 |
| | 0.0112 | 0 | 0 | 0 | 0 | 0 | 0 | 0 | 0 | 0 | 0 | 0 | 0 | N | 0 | 0 | 0 |
| 209 | 5.6 | 3 | 3 | 3 | 3 | 3 | 0 | 3 | 3 | 3 | 3 | 3 | 3 | 3 | 3 | 3 | 3 |
| | 1.12 | 0 | 3 | 3 | 3 | 3 | 0 | 3 | 3 | 3 | 3 | 3 | 2 | 3 | 3 | 3 | 3 |
| | 0.28 | 0 | 1 | 0 | 1 | 3 | 0 | 0 | 0 | 0 | 0 | 0 | 0 | 3 | 3 | 3 | 3 |
| | .056 | 0 | 0 | 0 | 0 | 0 | 0 | 0 | 0 | 0 | 0 | 0 | 0 | N | 1 | 1 | 2 |
| | 0.0112 | 0 | 0 | 0 | 0 | 0 | 0 | 0 | 0 | 0 | 0 | 0 | 0 | N | 0 | 0 | 0 |

The post-emergence herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan, except for the control pans, is removed individually to a spraying chamber and sprayed by means of an atomizer at the rate noted. In the spray solution is an amount of an emulsifying agent mixture to give a spray solution or suspension which contains about 0.4% by weight of the emulsifier. The spray solution or suspension contains a sufficient amount of the candidate chemical in order to give application rates corresponding to those set forth in the tables. The pans were returned to the greenhouse and watered as before and the injury to the plants as compared to the control is observed at approximately 10-14 days (usually 11 days) and in some instances observed again at 24-28 days (usually 25 days) after spraying.

The post-emergent herbicidal activity index used in Table II is as follows:

| Plant Response | Index |
|---|---|
| 0-24% Inhibition | 0 |
| 25-49% Inhibition | 1 |
| 50-74% Inhibition | 2 |
| 75-99% Inhibition | 3 |
| 100% Inhibition | 4 |

The letter identifying plants used in the following tests are identical to those used for corresponding tests in the pre-emergence tests in Table I above.

TABLE 23

| Example No. | kg/ha | A | B | C | D | E | F | G | H | I | J | K |
|---|---|---|---|---|---|---|---|---|---|---|---|---|
| 6 | 11.2 | 0 | 0 | 0 | 0 | 0 | 0 | 0 | 0 | 0 | 0 | 0 |
| 7 | 11.2 | — | 0 | 0 | 0 | 0 | 0 | 0 | 0 | 0 | 0 | 0 |
| 94 | 11.2 | — | 0 | 0 | 0 | 0 | 0 | 0 | 0 | 0 | 0 | 0 |
| 95 | 11.2 | — | 0 | 0 | 0 | 0 | 0 | 0 | 0 | 0 | 0 | 1 |
| 12 | 11.2 | 0 | 0 | 1 | 1 | 0 | 0 | 0 | 0 | 0 | 0 | 2 |
| 38 | 11.2 | 0 | 0 | 0 | 0 | 0 | 0 | 0 | 0 | 0 | 0 | 0 |
| 32 | 11.2 | 2 | 0 | 0 | 0 | 0 | 0 | 0 | 0 | 0 | 0 | 0 |
| 37 | 11.2 | 0 | 0 | 0 | 1 | 0 | 0 | 0 | 0 | 0 | 0 | 0 |
| 13 | 11.2 | 0 | 1 | 0 | 2 | 0 | 0 | 0 | 0 | 0 | 0 | 2 |
| 39 | 11.2 | 0 | 0 | 0 | 0 | 0 | 0 | 0 | 0 | 0 | 0 | 0 |
| 28 | 11.2 | 0 | 1 | 0 | 0 | 0 | 0 | 0 | 0 | 0 | 0 | 0 |
| 96 | 11.2 | 0 | 0 | 0 | 0 | 0 | — | 0 | 0 | 0 | 0 | 0 |
| 19 | 11.2 | — | 0 | 0 | 0 | 0 | 0 | 0 | 0 | 0 | 0 | 0 |
| 8 | 11.2 | 0 | 0 | 0 | 0 | 0 | 0 | 0 | 0 | 0 | 0 | 0 |
| 46 | 11.2 | 0 | 0 | 0 | 0 | 0 | 0 | 0 | 0 | 0 | 0 | 0 |
| 61 | 11.2 | 0 | 0 | 0 | 0 | 0 | 0 | 0 | 0 | 0 | 0 | 0 |
| 45 | 11.2 | 0 | 0 | 0 | 0 | 0 | 0 | 0 | 0 | 0 | 0 | 0 |
| 88 | 11.2 | 0 | 0 | 0 | 0 | 0 | — | 0 | 0 | 0 | 0 | 0 |
| 92 | 11.2 | 0 | 0 | 0 | 0 | 0 | — | 0 | 0 | 0 | 0 | 0 |
| 89 | 11.2 | 0 | 0 | 0 | 0 | 0 | — | 0 | 0 | 0 | 0 | 0 |
| 27 | 11.2 | 3 | 0 | 0 | 0 | 0 | — | 0 | 0 | 0 | 0 | 0 |
| 59 | 11.2 | — | 0 | 0 | 0 | 0 | — | 0 | 0 | 0 | 0 | 0 |
| 60 | 11.2 | 0 | 0 | 0 | 0 | 0 | — | 0 | 0 | 0 | 0 | 0 |
| 91 | 11.2 | — | 0 | 0 | 0 | 0 | — | 0 | 0 | 0 | 0 | 0 |
| 52 | 11.2 | — | 0 | 0 | 0 | 0 | — | 0 | 0 | 0 | 0 | 0 |
| 58 | 11.2 | — | 0 | 0 | 0 | 0 | — | 0 | 0 | 0 | 0 | 0 |
| 62 | 11.2 | — | 0 | 1 | 0 | 0 | — | 0 | 0 | 0 | 0 | 0 |
| 90 | 11.2 | — | 0 | 0 | 0 | 0 | — | 0 | 0 | 0 | 0 | 0 |

TABLE 23-continued

| | | | | | | | | | | | | |
|---|---|---|---|---|---|---|---|---|---|---|---|---|
| 18 | 11.2 | — | 0 | 0 | 0 | 0 | — | 0 | 0 | 0 | 0 | 0 |
| 40 | 11.2 | — | 1 | 0 | 0 | 0 | 0 | 0 | 0 | 0 | 0 | 0 |
| 29 | 11.2 | — | 1 | 0 | 1 | 0 | 0 | 0 | 0 | 0 | 0 | 0 |
| 47 | 11.2 | — | 1 | 0 | 1 | 0 | — | 0 | 0 | 0 | 0 | 0 |
| 48 | 11.2 | — | 0 | 0 | 0 | 0 | 0 | 0 | 0 | 0 | 0 | 0 |
| 46 | 11.2 | — | 0 | 0 | 0 | 0 | 0 | 0 | 0 | 0 | 0 | 0 |
| 15 | 11.2 | 0 | 1 | 1 | 1 | 0 | 0 | 0 | 0 | 0 | 0 | 0 |
| 44 | 11.2 | 0 | 0 | 0 | 1 | 0 | 0 | 0 | 0 | 0 | 0 | 0 |
| 31 | 11.2 | 0 | 0 | 0 | 0 | 0 | 0 | 0 | 0 | 0 | 0 | 0 |
| 53 | 11.2 | 0 | 1 | 0 | 1 | 0 | 0 | 0 | 0 | 0 | 0 | 1 |
| 16 | 11.2 | 0 | 1 | 1 | 1 | 1 | 0 | 0 | 0 | 0 | 0 | 1 |
| 21 | 11.2 | 0 | 1 | 1 | 2 | 0 | 0 | 0 | 0 | 0 | 0 | 0 |
| 64 | 11.2 | 0 | 1 | 1 | 2 | 0 | 0 | 0 | 0 | 0 | 0 | 0 |
| 32 | 11.2 | 0 | 0 | 0 | 1 | 1 | 0 | 0 | 0 | 0 | 0 | 0 |
| 54 | 11.2 | 0 | 1 | 1 | 2 | 0 | 1 | 0 | 0 | 0 | 0 | 2 |
| 37 | 11.2 | 0 | 1 | 0 | 0 | 0 | 0 | 0 | 0 | 0 | 0 | 0 |
| 11 | 11.2 | 0 | 0 | 0 | 1 | 0 | — | 0 | 0 | 0 | 0 | 0 |
| 87 | 11.2 | 0 | 1 | 0 | 1 | 0 | — | 0 | 0 | 0 | 0 | 0 |
| 97 | 11.2 | 0 | 0 | 0 | 0 | — | 0 | 0 | 0 | 0 | 0 | 0 |
| 20 | 11.2 | — | 1 | 0 | 1 | 0 | — | 0 | 0 | 0 | 0 | 0 |
| 41 | 11.2 | — | 0 | 0 | 0 | 0 | — | 0 | 0 | 0 | 0 | 0 |
| 22 | 11.2 | 0 | 0 | 0 | 0 | 0 | — | 0 | 0 | 0 | 0 | 0 |
| 75 | 11.2 | 0 | 0 | 1 | 0 | 0 | — | 0 | 0 | 0 | 0 | 0 |
| 14 | 11.2 | 0 | 0 | 0 | 0 | 0 | — | 0 | 0 | 0 | 0 | 0 |
| 30 | 11.2 | 0 | 0 | 0 | 0 | 0 | — | 0 | 0 | 0 | 0 | 0 |
| 23 | 11.2 | 0 | 0 | 0 | 0 | 0 | — | 0 | 0 | 0 | 0 | 0 |
| 35 | 11.2 | 0 | 0 | 0 | 0 | 0 | — | 0 | 0 | 0 | 0 | 0 |
| 17 | 11.2 | 0 | — | 1 | 2 | 0 | 0 | 0 | 0 | 1 | 0 | 2 |
| 34 | 11.2 | 0 | 0 | 0 | 0 | 0 | 0 | 0 | 0 | — | 0 | 0 |
| 50 | 11.2 | 0 | 0 | 0 | 0 | 0 | — | 0 | 0 | 0 | 0 | 0 |
| 55 | 11.2 | 0 | 2 | 1 | 2 | 2 | — | 2 | 0 | 0 | 1 | 2 |
| 55* | 11.2 | 0 | 2 | 2 | 2 | 3 | — | 2 | 1 | 0 | 2 | 2 |
| 33 | 11.2 | 0 | 1 | 0 | 1 | 1 | — | 0 | 0 | 0 | 0 | 0 |
| 49 | 11.2 | 0 | 0 | 0 | 1 | 0 | — | 0 | 0 | 0 | 0 | 0 |
| 65 | 11.2 | 0 | 0 | 0 | 0 | 0 | — | 0 | 0 | 0 | 0 | 0 |
| 51 | 11.2 | 0 | 0 | 0 | 0 | 0 | 0 | 0 | 0 | 0 | 0 | 0 |
| 68 | 11.2 | 0 | 0 | 0 | 0 | 0 | 0 | 0 | 0 | 0 | 0 | 0 |
| 67 | 11.2 | 0 | 0 | 0 | 0 | 0 | 0 | 0 | 0 | 0 | 0 | 1 |
| 76 | 11.2 | 0 | 1 | 0 | 1 | 2 | 0 | 1 | 0 | 1 | 0 | 1 |
| 77 | 11.2 | 0 | 1 | 1 | 1 | 1 | 1 | 0 | 0 | 0 | 0 | 0 |
| 83 | 11.2 | 0 | 0 | 1 | 0 | 0 | 0 | 0 | 0 | 0 | 0 | 0 |
| 82 | 11.2 | 0 | 0 | 1 | 1 | 0 | 0 | 0 | 0 | 0 | 0 | 0 |
| 84 | 11.2 | 0 | 0 | 0 | 0 | 0 | 0 | 0 | 0 | 0 | 0 | 0 |
| 66 | 11.2 | 0 | 0 | 0 | 0 | 0 | 0 | 0 | 0 | 0 | 0 | 0 |
| 85 | 11.2 | 1 | 0 | 0 | 0 | 0 | 0 | 2 | 0 | 0 | 0 | 2 |
| 86 | 11.2 | 0 | 0 | 0 | 0 | 0 | 0 | 0 | 0 | 0 | 0 | 0 |
| 112 | 11.2 | 2 | — | 1 | 1 | 0 | 0 | 0 | 0 | 0 | 0 | 0 |
| 70 | 11.2 | 0 | 0 | 0 | 0 | 0 | — | 0 | 0 | 0 | 0 | 0 |
| 24 | 11.2 | 0 | 0 | 0 | 0 | 0 | — | 0 | 0 | 0 | 0 | 0 |
| 36 | 11.2 | 0 | 0 | 0 | 0 | 0 | 0 | 0 | 0 | 0 | 0 | 0 |
| 71 | 11.2 | 0 | 0 | 0 | 0 | 0 | 0 | 0 | 0 | 0 | 0 | 0 |
| 103 | 11.2 | 0 | 0 | 0 | 0 | 0 | 0 | 0 | 0 | 0 | 0 | 0 |
| 100 | 11.2 | 0 | 0 | 0 | 0 | 0 | 0 | 0 | 0 | 0 | 0 | 0 |
| 69 | 11.2 | 0 | 1 | 0 | 0 | 0 | — | 0 | 0 | 0 | 0 | 1 |
| 72 | 11.2 | 0 | 0 | 0 | 0 | 0 | — | 0 | 0 | 0 | 0 | 0 |
| 99 | 11.2 | 0 | — | 0 | 0 | 0 | 0 | 0 | 0 | 0 | 0 | 0 |
| 81 | 11.2 | 0 | 0 | 0 | 1 | 0 | 0 | 0 | 0 | 0 | 0 | 0 |
| 42 | 11.2 | — | 0 | 0 | 0 | 0 | 0 | 0 | 0 | 0 | 0 | 0 |
| 74 | 11.2 | 0 | 1 | 0 | 1 | 0 | 0 | 0 | 0 | 0 | 0 | 1 |
| 78 | 11.2 | — | 0 | 0 | 0 | 0 | 0 | 0 | 0 | 0 | 0 | 1 |
| 73 | 11.2 | 0 | 1 | 1 | 1 | 0 | 0 | 0 | 0 | 0 | 0 | 0 |
| 98 | 11.2 | 0 | 0 | 0 | 0 | 0 | 0 | — | 0 | 0 | 0 | 0 |
| 10 | 11.2 | 0 | — | 0 | 0 | 0 | 0 | 0 | 0 | 0 | 0 | 0 |
| 101 | 11.2 | — | 0 | 0 | 0 | 0 | 1 | 0 | 0 | 0 | 0 | 2 |
| 25 | 11.2 | 0 | 0 | 0 | 1 | 0 | 0 | 0 | 0 | 0 | 0 | 0 |
| 102 | 11.2 | 0 | 0 | 0 | 0 | 0 | 0 | 0 | 0 | 0 | 0 | 0 |
| 134 | 11.2 | 0 | 0 | 0 | 0 | 0 | 0 | 0 | 0 | 0 | 0 | 0 |
| 130 | 11.2 | 0 | 0 | 0 | 0 | 0 | 0 | 0 | 0 | 0 | 0 | 0 |
| 128 | 11.2 | 0 | 0 | 0 | 0 | 0 | 0 | 0 | 0 | 0 | 0 | 0 |
| 104 | 11.2 | 0 | 0 | 0 | 0 | 2 | 0 | 0 | 0 | 0 | 0 | 0 |
| 127 | 11.2 | 0 | 0 | 0 | 1 | 0 | 0 | 0 | 0 | 0 | 0 | 0 |
| 129 | 11.2 | 0 | 1 | 1 | 2 | 3 | 0 | 0 | 0 | 0 | 0 | 0 |
| 131 | 11.2 | 0 | 1 | 0 | 1 | 0 | 0 | 0 | 0 | 0 | 0 | 2 |
| 105 | 11.2 | 0 | 0 | 1 | 1 | 0 | 0 | 0 | 0 | 0 | 0 | 1 |
| 133 | 11.2 | 0 | 1 | 1 | 1 | 1 | 1 | 0 | 0 | 0 | 0 | 2 |
| 80 | 11.2 | 0 | 1 | 1 | 1 | 1 | 0 | 0 | 0 | 0 | 0 | 1 |
| 79 | 11.2 | — | 0 | 0 | 0 | 0 | 0 | 0 | 0 | 0 | 0 | 0 |
| 26 | 11.2 | — | 0 | 0 | 0 | 0 | 0 | 0 | 0 | 0 | 0 | 0 |
| 27 | 11.2 | — | 0 | 0 | 0 | 0 | 0 | 0 | 0 | 0 | 0 | 0 |
| 123 | 11.2 | 0 | 0 | 0 | 1 | 0 | 0 | 0 | 0 | 0 | 0 | 0 |
| 124 | 11.2 | 0 | 0 | 0 | 1 | 0 | 0 | 0 | 0 | 0 | 0 | 0 |
| 119 | 11.2 | 0 | 1 | 0 | 0 | 0 | 0 | 0 | 0 | 0 | 0 | 0 |

TABLE 23-continued

| | | | | | | | | | | | | |
|---|---|---|---|---|---|---|---|---|---|---|---|---|
| 109 | 11.2 | 0 | 0 | 0 | 1 | 0 | 0 | 0 | 0 | 0 | 0 | 0 |
| 43 | 11.2 | 0 | 0 | 0 | 0 | 0 | 0 | 0 | 0 | 0 | 0 | 0 |
| 107 | 11.2 | 0 | — | 0 | 0 | 0 | 0 | 0 | 0 | 0 | 0 | 0 |
| 110 | 11.2 | 0 | 0 | 0 | 1 | 0 | 0 | 0 | 0 | 0 | 0 | 1 |
| 111 | 11.2 | 0 | — | 1 | 2 | 0 | 0 | 0 | 0 | 0 | 0 | 1 |
| 106 | 11.2 | 0 | — | 0 | 0 | 0 | 0 | 0 | 0 | 0 | 0 | 0 |
| 120 | 11.2 | 0 | — | 0 | 1 | 0 | 0 | 0 | 0 | 0 | 0 | 0 |
| 122 | 11.2 | 0 | 1 | 1 | 1 | 0 | 0 | 0 | 0 | 0 | 0 | 0 |
| 117 | 11.2 | 0 | 1 | 1 | 2 | 1 | 0 | 0 | 0 | 0 | 0 | 0 |
| 118 | 11.2 | 0 | 0 | 0 | 0 | 0 | 0 | 0 | 0 | 0 | 0 | 0 |
| 113 | 11.2 | 0 | 1 | 1 | 2 | 0 | 0 | 0 | 0 | 0 | 0 | 0 |
| 121 | 11.2 | 0 | 0 | 0 | 1 | 0 | 0 | 0 | 0 | 0 | 0 | 0 |
| 125 | 11.2 | 1 | 1 | 0 | 1 | 1 | 0 | 0 | 0 | 0 | 0 | 1 |
| 137 | 11.2 | 0 | 0 | 0 | 0 | 0 | 0 | 0 | 0 | 0 | 0 | 0 |
| 136 | 11.2 | 0 | 1 | 1 | 2 | 1 | 0 | 0 | 0 | 0 | 0 | 0 |
| 135 | 11.2 | 0 | 0 | 0 | 0 | 0 | 0 | 0 | 0 | 0 | 0 | 0 |
| 138 | 11.2 | 0 | 0 | 1 | 1 | 0 | 0 | 1 | 0 | 1 | 1 | 2 |
| 138 | 11.2 | 0 | 1 | 1 | 1 | 0 | 0 | 0 | 0 | 0 | 0 | 1 |
| 139 | 11.2 | 0 | 1 | 0 | 1 | 0 | 0 | 0 | 0 | 0 | 0 | 0 |
| 140 | 11.2 | 0 | 0 | 0 | 0 | 0 | 0 | 0 | 0 | 0 | 0 | 0 |
| 141 | 11.2 | 0 | 0 | 1 | 1 | 0 | 1 | 0 | 0 | N | 0 | 0 |
| 142 | 11.2 | 0 | 0 | 0 | 0 | 0 | 0 | 0 | 0 | 0 | 0 | 0 |
| 143 | 11.2 | 0 | 0 | 0 | 0 | 0 | 0 | 0 | 0 | 0 | 0 | 0 |
| 144 | 11.2 | 0 | 0 | 0 | 0 | 0 | 0 | 0 | 0 | 0 | 0 | 0 |
| 146 | 11.2 | 1 | 0 | 2 | 1 | 2 | 1 | 0 | 0 | N | 0 | 0 |
| 147 | 11.2 | 0 | 1 | 1 | 1 | 1 | 0 | 0 | 0 | N | 0 | 0 |
| 148 | 11.2 | 1 | 1 | 1 | 1 | 2 | 0 | 0 | 0 | 0 | 0 | 1 |
| 149 | 11.2 | N | 0 | 1 | 1 | 0 | 0 | 0 | 0 | 0 | 0 | 0 |
| 150 | 11.2 | 0 | 0 | 0 | 0 | 0 | 0 | 0 | 0 | 0 | 0 | 0 |
| 152 | 11.2 | 0 | 0 | 0 | 0 | 1 | 0 | 0 | 0 | N | 0 | 0 |
| 153 | 11.2 | 0 | 1 | 0 | 0 | 0 | 0 | 0 | 0 | 0 | 0 | 0 |
| 154 | 11.2 | 0 | 0 | 0 | 0 | 0 | 0 | 0 | 0 | — | 0 | 0 |
| 155 | 11.2 | 0 | 0 | 0 | 0 | 0 | 0 | 0 | 0 | 0 | 0 | 0 |
| 156 | 11.2 | 0 | 0 | 0 | 0 | 0 | 0 | 0 | 0 | 0 | 0 | 0 |
| 157 | 11.2 | 0 | 2 | 1 | 2 | 0 | 0 | 0 | 0 | 0 | 0 | 1 |
| 158 | 11.2 | 0 | 0 | 0 | 0 | 0 | 0 | 0 | 0 | 0 | 0 | 0 |
| 159 | 11.2 | 0 | 0 | 0 | 1 | 0 | 0 | 0 | 0 | 0 | 0 | 0 |
| 160 | 11.2 | 0 | 0 | 0 | 0 | 0 | 0 | 0 | 0 | 0 | 0 | 0 |
| 161 | 11.2 | 0 | 0 | 0 | 1 | 0 | 0 | 0 | 0 | 0 | 0 | 0 |
| 162 | 11.2 | 0 | 0 | 0 | 1 | 0 | 0 | 0 | 0 | 0 | 0 | 0 |
| 163 | 11.2 | 0 | 0 | 0 | 0 | 0 | 0 | 0 | 0 | 0 | 0 | 0 |
| 164 | 11.2 | 0 | 0 | 0 | 0 | 0 | 0 | 0 | 0 | 0 | 0 | 0 |
| 165 | 11.2 | 0 | 0 | 0 | 1 | 1 | 0 | 0 | 0 | 0 | 0 | 0 |
| 166 | 11.2 | 0 | 0 | 0 | 0 | 0 | 0 | 0 | 0 | 0 | 0 | 0 |
| 167 | 11.2 | 0 | 1 | 0 | 1 | 0 | 0 | 0 | 0 | 0 | 0 | 0 |
| 170 | 11.2 | 0 | 1 | 1 | 1 | 0 | 0 | 1 | 0 | 0 | 0 | 0 |
| 171 | 11.2 | 1 | 1 | 1 | 1 | 0 | 0 | 0 | 0 | 0 | 0 | 0 |
| 172 | 11.2 | 0 | 0 | 0 | 1 | 0 | 0 | 0 | 0 | 0 | 0 | 0 |
| 173 | 11.2 | 0 | 1 | 0 | 1 | 0 | 0 | 0 | 0 | 0 | 0 | 0 |
| 174 | 11.2 | 0 | 0 | 0 | 0 | 0 | 0 | 0 | 0 | 0 | 0 | 0 |
| 175 | 11.2 | 0 | 0 | 1 | 1 | 0 | 0 | 0 | 0 | 0 | 0 | 0 |
| 176 | 11.2 | 0 | 1 | 0 | 0 | 0 | 0 | 0 | 0 | 0 | 0 | 0 |
| 177 | 11.2 | 0 | 0 | 0 | 0 | 0 | 0 | 0 | 0 | 0 | 0 | 0 |
| 178 | 11.2 | 0 | 0 | 0 | 0 | 0 | 0 | 0 | 0 | 0 | 0 | 0 |
| 179 | 11.2 | 0 | 0 | 0 | 0 | 0 | 0 | 0 | 0 | 0 | 0 | 0 |
| 180 | 11.2 | 0 | 0 | 0 | 0 | 0 | 0 | 0 | 0 | 0 | 0 | 0 |
| 181 | 11.2 | 0 | 0 | 0 | 0 | 0 | 0 | 0 | 0 | 0 | 0 | 0 |
| 182 | 11.2 | 0 | 0 | 0 | 0 | 0 | 0 | 0 | 0 | 0 | 0 | 0 |
| 183 | 11.2 | 0 | 0 | 0 | 0 | 2 | 0 | 0 | 0 | 0 | 0 | 0 |
| 184 | 11.2 | N | 0 | 0 | 0 | 0 | 0 | 0 | 0 | 0 | 0 | 0 |
| 185 | 11.2 | N | 0 | 0 | 0 | 0 | 0 | 0 | 0 | 0 | 0 | 0 |
| 186 | 11.2 | 0 | 1 | 0 | 0 | 0 | 0 | 0 | 0 | — | 0 | 0 |
| 187 | 11.2 | 0 | 0 | 0 | 0 | 0 | 0 | 0 | 0 | — | 0 | 0 |
| 189 | 11.2 | 0 | 1 | 1 | 0 | 0 | 0 | 0 | 0 | N | 0 | 0 |
| 190 | 11.2 | 0 | 0 | 0 | 0 | 0 | 0 | 0 | 0 | — | 0 | 0 |
| 191 | 11.2 | N | 0 | 1 | 1 | 0 | 0 | 0 | 0 | — | 0 | 0 |
| 192 | 11.2 | 0 | 0 | 0 | 0 | 0 | 0 | 0 | 0 | — | 0 | 0 |
| 193 | 11.2 | N | 0 | 1 | 0 | 0 | 0 | 0 | 0 | N | 0 | 0 |
| 194 | 11.2 | 0 | 1 | 0 | 1 | 0 | 0 | 0 | 0 | N | 0 | 0 |
| 195 | 11.2 | 0 | 1 | 1 | 1 | 0 | 0 | 0 | 0 | N | 0 | 0 |
| 196 | 11.2 | 0 | 1 | 1 | 1 | 0 | 0 | 0 | 0 | N | 0 | 0 |
| 197 | 11.2 | 0 | 0 | 0 | 0 | 0 | 0 | 0 | 0 | N | 0 | 0 |
| 198 | 11.2 | 0 | 0 | 0 | 1 | 0 | 0 | 0 | 0 | N | 0 | 0 |
| 199 | 11.2 | 0 | 0 | 0 | 0 | 0 | 0 | 0 | 0 | N | 0 | 0 |
| 200 | 11.2 | 0 | 1 | 0 | 1 | 1 | 0 | 0 | 0 | — | 0 | 0 |
| 201 | 11.2 | 1 | 0 | 0 | 0 | 0 | 0 | 0 | N | N | 0 | 1 |
| 202 | 11.2 | 0 | 0 | 0 | 0 | 0 | 0 | 0 | 0 | 0 | 0 | 0 |
| 203 | 11.2 | 0 | 0 | 0 | 0 | 0 | 0 | 0 | 0 | N | 0 | 0 |
| 204 | 11.2 | 0 | 0 | 0 | 0 | 1 | 0 | 0 | 0 | N | 0 | 0 |
| 209 | 11.2 | 0 | 0 | 1 | 0 | 1 | 0 | 0 | 0 | N | 0 | 0 |
| 210 | 11.2 | 0 | 0 | 0 | 1 | 0 | 0 | 0 | 0 | N | 0 | 0 |
| 213 | 11.2 | 0 | 0 | 0 | 1 | 0 | 0 | 0 | 0 | N | 0 | 1 |

TABLE 23-continued

| | kg/ha | L | M | N | O | P | B | Q | D | R | E | F | C | J | S | K | T |
|---|---|---|---|---|---|---|---|---|---|---|---|---|---|---|---|---|---|
| 215 | 11.2 | N | 0 | 0 | 1 | 3 | 0 | 0 | 0 | 0 | 0 | 0 | | | | | 1 |
| 216 | 11.2 | 0 | 0 | 0 | 0 | 0 | 0 | 0 | 0 | 0 | 0 | 0 | | | | | |
| 217 | 11.2 | 0 | 0 | 0 | 0 | 0 | 0 | 0 | 0 | N | 0 | 0 | | | | | |
| 219 | 11.2 | N | 0 | 0 | 0 | 0 | 0 | 0 | 0 | 0 | 0 | 0 | | | | | |
| 220 | 11.2 | N | 0 | 0 | 0 | 0 | 0 | 0 | 0 | 0 | 0 | 0 | | | | | |
| 221 | 11.2 | N | 0 | 0 | 0 | 0 | 0 | 0 | 0 | 0 | 0 | 0 | | | | | |
| 222 | 11.2 | 0 | 0 | 0 | 0 | 0 | 0 | 0 | 0 | 0 | 0 | 0 | | | | | |
| 223 | 11.2 | 0 | 0 | 0 | 0 | 0 | 0 | 0 | 0 | 0 | 0 | 0 | | | | | |
| 224 | 11.2 | 0 | 0 | 0 | 0 | 0 | 0 | 0 | 0 | 0 | 0 | 0 | | | | | |
| 225 | 11.2 | N | 0 | 0 | 0 | 0 | 0 | 0 | 0 | 0 | 0 | 0 | | | | | |
| 226 | 11.2 | N | 0 | 0 | 0 | 0 | 0 | 0 | 0 | 0 | 0 | 0 | | | | | |
| 227 | 11.2 | N | 0 | 1 | 0 | 0 | 0 | 0 | 0 | 0 | 0 | 0 | | | | | |
| 233 | 11.2 | N | 0 | 1 | 0 | 0 | 0 | 0 | 0 | 0 | 0 | 0 | | | | | |
| 234 | 11.2 | N | 0 | 1 | 1 | 0 | 0 | 0 | 0 | 0 | 0 | 0 | | | | | |
| 235 | 11.2 | 0 | 0 | 1 | 1 | 0 | 0 | 0 | 0 | 0 | 0 | 0 | | | | | |
| 236 | 11.2 | 0 | 0 | 0 | 1 | 0 | 0 | 0 | 0 | 0 | 0 | 0 | | | | | |
| 237 | 11.2 | N | 0 | 1 | 1 | 0 | 0 | 0 | 0 | 0 | 0 | 0 | | | | | |
| 238 | 11.2 | N | 1 | 1 | 1 | 0 | 1 | 0 | 0 | 0 | 0 | 1 | | | | | |
| 240 | 11.2 | 2 | 0 | 0 | 0 | 1 | 0 | 0 | 0 | 0 | 0 | 0 | | | | | |
| 241 | 11.2 | N | 0 | 0 | 0 | 0 | 0 | 0 | 0 | 0 | 0 | 0 | | | | | |
| 242 | 11.2 | 0 | 0 | 0 | 0 | 0 | 0 | 0 | 0 | — | 0 | 0 | | | | | |
| 243 | 11.2 | 0 | 0 | 0 | 0 | 0 | 0 | 0 | 0 | — | 0 | 0 | | | | | |
| 244 | 11.2 | 0 | 1 | 1 | 1 | 0 | 0 | 0 | 0 | — | 0 | 0 | | | | | |
| 245 | 11.2 | 0 | 0 | 1 | 1 | 1 | 0 | 0 | 0 | 0 | 0 | 1 | | | | | |
| 246 | 11.2 | N | 0 | 1 | 2 | 1 | 0 | 0 | 0 | 0 | 0 | 0 | | | | | |
| Example No. | kg/ha | L | M | N | O | P | B | Q | D | R | E | F | C | J | S | K | T |
| 5 | 1.12 | 0 | 0 | 0 | 0 | 0 | 0 | 0 | 0 | 0 | 3 | — | 0 | 0 | 0 | 0 | 0 |
| | 5.6 | 0 | 1 | 0 | 0 | 0 | 0 | 0 | 0 | 0 | 0 | — | 0 | 0 | 0 | 0 | 0 |
| 16 | 11.2 | 2 | 0 | 3 | 0 | 1 | 2 | 0 | 1 | 1 | 2 | 1 | 2 | 1 | 1 | 1 | 2 |
| | .056 | 0 | 0 | 0 | 0 | 0 | 0 | 0 | 0 | 0 | 0 | 0 | 0 | 0 | 0 | 0 | 0 |
| | .28 | 1 | 0 | 0 | 0 | 0 | 0 | 0 | 0 | 0 | 0 | 0 | 0 | 0 | 0 | 0 | 0 |
| | 1.12 | 0 | 0 | 0 | 0 | 0 | 1 | 0 | 0 | 0 | 2 | — | 2 | 0 | 0 | 0 | 0 |
| | 5.6 | 2 | 1 | 2 | 1 | 1 | 2 | 0 | 0 | 0 | 2 | — | 2 | 0 | 1 | 1 | 1 |

*4-week observation

Compounds of this invention have been found to be extremely efficacious as herbicides, in various crops, including cotton, rice, sugarcane, sunflower, peanuts, wheat, barley, coffee, and citrus. Some of the compounds of this invention are also particularly useful in rice. In Table 23 below, data are presented showing the effect of various compounds of the invention on weed species in the presence of the above-mentioned crops.

The plant species identified by abbreviation in Table 23 are as follows:

Sobe — soybean
Cotz — cotton
Rrpw — redroot pigweed
Shca — shattercane
Sejg — seedling johnsongrass
Reri — redrice
Wipm — wild prosso millet
Bygr — barnyardgrass
Yens — yellownutsedge The procedure utilized is that described above with respect to Tables 20 and 21. Observations were made about 3 weeks after planting. Below each plant species designation in Table 23 is listed the percent inhibition of growth observed. As above, 100 means complete control and 0 means no control.

TABLE 24

| Compound | kg/ha | Sobe | Cotz | Rrpw | Shca | Sejg | Reri | Wipm | Bygr | Yens | Rice |
|---|---|---|---|---|---|---|---|---|---|---|---|
| Ex. 67 | 0.56 | 60 | 0 | 100 | 100 | 100 | 98 | 100 | 100 | 0 | 100 |
| | 0.28 | 40 | 0 | 40 | 100 | 100 | 98 | 100 | 100 | 0 | 100 |
| | 0.14 | 0 | 0 | 20 | 95 | 95 | 70 | 80 | 100 | 0 | 100 |
| | 0.07 | 0 | 0 | 0 | 90 | 80 | 0 | 70 | 90 | 0 | 50 |
| Ex. 72 | 0.56 | 60 | 0 | 90 | 100 | 100 | 98 | 95 | 100 | 0 | 100 |
| | 0.28 | 30 | 0 | 20 | 98 | 95 | 70 | 90 | 95 | 0 | 95 |
| | 0.14 | 0 | 0 | 0 | 90 | 90 | 0 | 60 | 90 | 0 | 60 |
| | 0.07 | 0 | 0 | 0 | 80 | 70 | 0 | 40 | 50 | 0 | 40 |
| Ex. 14 | 0.56 | 95 | 15 | 95 | 100 | 100 | 100 | 100 | 100 | 90 | 100 |
| | 0.28 | 90 | 0 | 80 | 100 | 100 | 100 | 100 | 100 | 80 | 100 |
| | 0.14 | 80 | 0 | 50 | 100 | 100 | 98 | 100 | 100 | 0 | 100 |
| | 0.07 | 10 | 0 | 20 | 100 | 98 | 80 | 95 | 100 | 0 | 98 |
| Ex. 111 | 0.56 | 0 | 0 | 80 | 98 | 98 | 30 | 90 | 95 | 0 | 98 |
| | 0.28 | 0 | 0 | 20 | 95 | 95 | 30 | 90 | 95 | 0 | 90 |
| | 0.14 | 0 | 0 | 0 | 80 | 80 | 0 | 50 | 80 | 0 | 30 |
| | 0.07 | 0 | 0 | 0 | 20 | 30 | 0 | 0 | 30 | 0 | 0 |
| Ex. 110 | 0.56 | 0 | 0 | 60 | 98 | 98 | 40 | 99 | 98 | 0 | 90 |
| | 0.28 | 0 | 0 | 0 | 90 | 90 | 0 | 80 | 85 | 0 | 50 |
| | 0.14 | 0 | 0 | 0 | 80 | 80 | 0 | 40 | 70 | 0 | 30 |
| | 0.07 | 0 | 0 | 0 | 40 | 50 | 0 | 0 | 20 | 0 | 0 |
| Ex. 26 | 0.56 | 0 | 0 | 40 | 95 | 95 | 0 | 80 | 90 | 0 | 50 |
| | 0.28 | 0 | 0 | 0 | 80 | 80 | 0 | 50 | 70 | 0 | 30 |
| | 0.14 | 0 | 0 | 0 | 30 | 40 | 0 | 0 | 0 | 0 | 0 |
| | 0.07 | 0 | 0 | 0 | 0 | 0 | 0 | 0 | 0 | 0 | 0 |
| Ex. 25 | 0.56 | 40 | 0 | 90 | 100 | 100 | 30 | 100 | 100 | 0 | 98 |

TABLE 24-continued

| Compound | kg/ha | Sobe | Cotz | Rrpw | Shca | Sejg | Reri | Wipm | Bygr | Yens | Rice |
|---|---|---|---|---|---|---|---|---|---|---|---|
| | 0.28 | 0 | 0 | 20 | 100 | 98 | 0 | 98 | 100 | 0 | 80 |
| | 0.14 | 0 | 0 | 0 | 95 | 95 | 0 | 90 | 90 | 0 | 40 |
| | 0.07 | 0 | 0 | 0 | 80 | 70 | 0 | 80 | 85 | 0 | 30 |
| Ex. 52 | 0.56 | 70 | 0 | 95 | 100 | 100 | 100 | 100 | 100 | 0 | 100 |
| | 0.28 | 30 | 0 | 20 | 100 | 100 | 70 | 100 | 100 | 0 | 95 |
| | 0.14 | 10 | 0 | 20 | 100 | 98 | 20 | 95 | 100 | 0 | 95 |
| | 0.07 | 0 | 0 | 0 | 90 | 90 | 0 | 80 | 90 | 0 | 60 |
| Ex. 53 | 0.56 | 30 | 0 | 100 | 100 | 98 | 80 | 100 | 100 | 0 | 100 |
| | 0.28 | 10 | 0 | 30 | 100 | 100 | 60 | 98 | 100 | 0 | 98 |
| | 0.14 | 0 | 0 | 0 | 85 | 90 | 0 | 80 | 80 | 0 | 50 |
| | 0.07 | 0 | 0 | 0 | 80 | 70 | 0 | 50 | 70 | 0 | 30 |
| Ex. 55 | 0.56 | 90 | 0 | 100 | 100 | 100 | 95 | 100 | 100 | 0 | 100 |
| | 0.28 | 80 | 0 | 98 | 100 | 100 | 70 | 100 | 100 | 0 | 95 |
| | 0.14 | 40 | 0 | 60 | 98 | 98 | 40 | 98 | 100 | 0 | 95 |
| | 0.07 | 0 | 0 | 0 | 90 | 85 | 0 | 90 | 85 | 0 | 70 |
| Ex. 54 | 0.56 | 90 | 0 | 95 | 100 | 100 | 90 | 100 | 100 | 0 | 100 |
| | 0.28 | 90 | 0 | 70 | 100 | 100 | 90 | 100 | 100 | 0 | 100 |
| | 0.14 | 60 | 0 | 20 | 100 | 100 | 40 | 100 | 100 | 0 | 99 |
| | 0.07 | 0 | 0 | 0 | 95 | 90 | 20 | 95 | 98 | 9 | 60 |
| Ex. 123 | 0.56 | 0 | 0 | 0 | 100 | 98 | 80 | 95 | 100 | 0 | 98 |
| | 0.28 | 0 | 0 | 0 | 95 | 95 | 20 | 95 | 95 | 0 | 80 |
| | 0.14 | 0 | 0 | 0 | 95 | 85 | 0 | 60 | 85 | 0 | 20 |
| | 0.07 | 0 | 0 | 0 | 30 | 40 | 0 | 0 | 30 | 0 | 0 |
| Ex. 124 | 0.56 | 0 | 0 | 0 | 85 | 70 | 0 | 90 | 50 | 0 | 40 |
| | 0.28 | 0 | 0 | 0 | 80 | 80 | 0 | 70 | 80 | 0 | 20 |
| | 0.14 | 0 | 0 | 0 | 20 | 40 | 0 | 0 | 40 | 0 | 0 |
| | 0.07 | 0 | 0 | 0 | 0 | 0 | 0 | 0 | 0 | 0 | 0 |
| Ex. 101 | 0.56 | 50 | 0 | 95 | 100 | 100 | 20 | 100 | 100 | 0 | 20 |
| | 0.28 | 30 | 0 | 60 | 100 | 100 | 0 | 100 | 100 | 0 | 20 |
| | 0.14 | 0 | 0 | 40 | 100 | 95 | 0 | 90 | 100 | 0 | 15 |
| | 0.07 | 0 | 0 | 0 | 95 | 95 | 0 | 70 | 95 | 0 | 0 |
| Ex. 86 | 0.56 | 30 | 0 | 100 | 100 | 100 | 70 | 100 | 100 | 0 | 98 |
| | 0.28 | 0 | 0 | 60 | 100 | 98 | 20 | 100 | 95 | 0 | 95 |
| | 0.14 | 0 | 0 | 0 | 95 | 95 | 0 | 90 | 95 | 0 | 80 |
| | 0.07 | 0 | 0 | 0 | 80 | 70 | 0 | 60 | 80 | 0 | 30 |
| Ex. 69 | 0.56 | 90 | 0 | 100 | 100 | 100 | 100 | 100 | 100 | 0 | 100 |
| | 0.28 | 80 | 0 | 80 | 100 | 100 | 98 | 100 | 100 | 0 | 100 |
| | 0.14 | 20 | 0 | 0 | 100 | 100 | 70 | 100 | 100 | 0 | 98 |
| | 0.07 | 0 | 0 | 0 | 90 | 80 | 20 | 90 | 90 | 0 | 90 |
| Ex. 80 | 0.56 | 40 | 0 | 100 | 100 | 100 | 70 | 100 | 100 | 20 | 98 |
| | 0.28 | 10 | 0 | 100 | 100 | 100 | 30 | 100 | 100 | 0 | 95 |
| | 0.14 | 0 | 0 | 90 | 98 | 95 | 0 | 95 | 98 | 0 | 60 |
| | 0.07 | 0 | 0 | 0 | 80 | 70 | 0 | 80 | 90 | 0 | 20 |

The preemergent herbicidal activity of dimethyl 2-(difluoromethyl)-6-(trifluoromethyl)-4-isobutyl-3,5-pyridinedicarboxylate with respect to various crop species is set forth below in Table 24. Utilizing the same procedure as described with respect to Tables 20 and 21, the herbicidal effect on the crops noted in Table 24 were observed at various rates of application. The data in Table 24 indicate that cotton has a high tolerance and peanut and sunflower have some tolerance for this compound in that these crops were relatively unaffected by the herbicide. The herbicidal activity is noted as in Table 24 wherein 100 indicates total control and 0 indicates no control. The crops listed by abbreviation are soybean (Sobe), cotton (Cotz), sugarbeet (Sube), alfalfa (Alfz), sunflower (Sufl), and peanut (Penu).

TABLE 25

| Rate k/ha | Sobe | Cotz | Sube | Rape | Flax | Alfz | Sufl | Penu |
|---|---|---|---|---|---|---|---|---|
| 2.4 | 98 | 50 | 100 | 100 | 100 | 100 | 50 | 80 |
| 1.2 | 90 | 20 | 100 | 100 | 100 | 100 | 20 | 50 |
| .6 | 90 | 0 | 100 | 100 | 100 | 100 | 0 | 20 |
| .3 | 90 | 0 | 95 | 100 | 100 | 100 | 0 | 10 |
| .15 | 50 | 0 | 90 | 90 | 90 | 95 | 0 | 0 |

The above tables illustrate one aspect of the present invention, that is, the use of the compounds of the invention to kill or injure undesirable plants, e.g., weeds.

As can be seen from the data above, some of the compounds appear to be quite safe on many crops such as cotton and can thus be used for selective control of weeds in such crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan) and polyoxyethylene derivatives of castor oil. Preferred dispersants are methyl cellulose, polyoxyethylene-/polyoxypropylene block copolymers, polyvinyl alcohol, sodium lignin sulfonates, polymeric alkyl naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, bentonite, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formu-lations contain from about 0.1–60% preferably 5–50% by weight of active ingredient, the upper limit being determined by the solubility limit of active ingredient in the solvent.

Concentrates are usually solutions of acitve ingredient in water-immiscible or partially water-immiscible solvents together with a surface active agent. Suitable solvents for the active ingredient of this invention include dimethylformamide, chlorinated solvents, dimethylsulfoxide, N-methylpyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivaties, thiolcabamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium
3-methyl-4-amino-6-phenyl-1,2,4-triazin-5-(4H)one
2-(4-chloro-6-ethylamino-1,3,5-sym-2-triazinylamino)-2-methylpropionitrile
3-cyclohexyl-6-dimethylamino-1-methyl-1,3,5-triazine-2,4(1H,3H)-dione
4-amino-6-(tert-butyl)-3-methylthio-as-triazin-5(4H)one
5-amino-4-chloro-2-phenyl-3(1H)-pyridazinone
5-methylamino-4-chloro-2-($\delta,\delta,\delta,\delta$-trifluoro-m-tolyl)-3(2H)-pyridazinone
5-bromo-3-(sec-butyl)-6-methyluracil Ureas N-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3(2-benzothiazolyl)urea
3-(p-Chlorophenyl)-1,1-dimethylurea
1-Butyl-3-(3,4-dichlorophenyl)-1-methylurea
N-(3-trifluoromethylphenyl)-N,N'-dimethylurea
3-(3,4-dichlorophenyl)-1-methoxy-1-methylurea
2-Chloro-N-([(4-methoxy-6-methyl-1,3,5-triazin-2-yl)amino]carbonyl)benzenesulfonamide
Methyl 2-((([(4,6-dimethyl-2-pyrimidinyl)amino]carbonyl)amino)sulfonyl)benzoate Carbamates/Thiolcarbamates 2-Chloroallyl diethyldithiocarbamate
S-(4-chlorobenzyl)N,N-diethylthiocarbamate
Isopropyl N-(3-chlorophenyl)carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate
Ethyl dipropylthiolcarbamate Acetamides/Acetanilides/Anilines/Amides 2-Chloro-N,N-diallylacetamide
N,N-dimethyl-2,2-diphenylacetamide N-(2,4-dimethyl-5-[[(trifluoromethyl)sulfonyl]amino]-phenyl]acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
δ,δ,δ-Trifluoro-2,6-dinitro-N,N-dipropyl-p-toluidine
N-(1,1-dimethylpropynyl)-3,5-dichlorobenzamide
α,α,α-Trifluoro-2,6-dinitro-N-propyl-N-(2-chloroethyl)-p-toluidine
3,5-Dinitro-4-dipropylamino-benzenesulfonamide
N-(1-ethylpropyl)-3,4-dimethyl-2,6-dinitro-benzenamine

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycerine and its salts
Potassium 4-amino-3,5,6-trichloropicolinate
2,3-Dihydro-3,3-dimethyl-2-ethoxy-5-benzofuranyl methanesulfonate

Ethers 2,4-Dichlorophenyl-4-nitrophenyl ether
2-Chloro-δ,δ,δ-trifluoro-p-tolyl-3-ethoxy-4-nitrodiphenyl ether
2-Chloro-1-(3-ethoxy-4-nitrophenoxy)-4-trifluoromethyl benzene

Miscellaneous 2,6-Dichlorobenzonitrile
Monosodium acid methanearsonate
Disodium methanearsonate Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above, which include compounds of this invention, are exemplified in several illustrative embodiments below.

| | Weight Percent |
|---|---|
| I. Emulsifiable Concentrates | |
| A. Compound of Example No. 14 | 45.6 |
| Monochlorobenzene | 26.6 |
| C9 Aromatics | 17.8 |
| Calcium sulfonyl benzene sulfonate | 5.0 |
| Castor oil ethoxylated with 54 moles | 5.0 |
| | 100.0 |
| B. Compound of Example No. 101 | 33.7 |
| Monochlorobenzene | 56.3 |
| Calcium sulfonyl benzene sulfonate | 4.3 |
| Castor oil ethoxylated with 54 mols | 5.7 |
| | 100.0 |
| C. Compound of Example No. 5 | 11.0 |
| Free acid of complex organic phosphate of aromatic or aliphatic hydrophobe base (e.g., GAFAC RE-610, registered trademark of GAF Corp.) | 5.59 |
| Polyoxyethylene/polyoxypropylene block copolymer with butanol (e.g., Tergitol XH, registered trademark of Union Carbide Corp.) | 1.11 |
| C9 aromatics | 5.34 |
| Monochlorobenzene | 76.96 |
| | 100.00 |
| D. Compound of Example No. 16 | 25.00 |
| Free acid of complex organic phosphate of aromatic or aliphatic hydrophobe base (e.g., GAFAC RE-610) | 5.00 |
| Polyoxyethylene/polyoxypropylene block copolymer with butanol (e.g., Tergitol XH) | 1.60 |
| Phenol | 4.75 |
| Monochlorobenzene | 63.65 |
| | 100.00 |
| II. Flowables | |
| A. Compound of Example No. 6 | 25.00 |
| Methyl cellulose | 0.3 |
| Silica Aerogel | 1.5 |
| Sodium lignosulfonate | 3.5 |
| Sodium N—methyl-N—oleyl taurate | 2.0 |
| Water | 67.7 |
| | 100.00 |
| B. Compound of Example No. 17 | 45.0 |
| Methyl cellulose | .3 |
| Silica aerogel | 1.5 |
| Sodium lignosulfonate | 3.5 |
| Sodium N—methyl-N—oleyl taurate | 2.0 |
| Water | 47.7 |
| | 100.00 |
| III. Wettable Powders | |
| A. Compound of Example No. 5 | 25.0 |
| Sodium lignosulfonate | 3.0 |
| Sodium N—methyl-N—oleyl-taurate | 1.0 |
| Amorphous silica (synthetic) | 71.0 |
| | 100.00 |
| B. Compound of Example No. 21 | 80.00 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 6 | 10.0 |
| Sodium lignosulfonate | 3.0 |
| Sodium N—methyl-N—oleyl-taurate | 1.0 |
| Kaolinite clay | 86.0 |
| | 100.00 |
| V. Dusts | |
| A. Compound of Example No. 2 | 2.0 |
| Attapulgite | 98.0 |
| | 100.00 |
| B. Compound of Example No. 9 | 60.0 |
| Montmorillonite | 40.0 |
| | 100.00 |
| C. Compound of Example No. 15 | 30.0 |
| Ethylene glycol | 1.0 |
| Bentonite | 69.0 |
| | 100.00 |
| D. Compound of Example No. 16 | 1.0 |
| Diatomaceous earth | 99.0 |
| | 100.00 |
| VI. Granules | |
| A. Compound of Example No. 8 | 15.0 |
| Granular attapulgite (20/40 mesh) | 85.0 |
| | 100.00 |
| B. Compound of Example No. 9 | 30.0 |
| Diatomaceous earth (20/40) | 70.0 |
| | 100.00 |
| C. Compound of Example No. 18 | 1.0 |
| Ethylene glycol | 5.0 |
| Methylene blue | 0.1 |
| Pyrophyllite | 93.9 |
| | 100.00 |
| D. Compound of Example No. 19 | 5.0 |

| | Weight Percent |
|---|---|
| Pyrophyllite (20/40) | 95.0 |
| | 100.00 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., powers dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from 0.02 to 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "solids" as defined in *Webster's New International Dictionary*, Second Edition, Unabridged (1961). Thus, the term refers to any substance or media in which vegetation may take root and grow, and includes not only earth but also compost, manure, muck, humus, sand and the like, adapted to support plant growth.

Although the invention is described with respect to specific modifications, the details thereof are not to be construed as limitations.

What is claimed is:

1. A compound represented by the structural formula

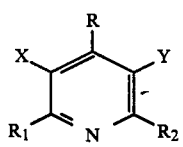

wherein:

R is selected from the group consisting of lower alkyl, lower alkenyl, lower alkynyl, lower alkenylalkyl, haloalkyl, haloalkenyl, $C_{3-7}$ cycloalkyl, $C_{3-6}$ cycloalkanylalkyl, phenyl, alkoxyalkyl, benzyloxymethyl, alkylthioalkyl, dialkoxyalkyl, (1-alkoxy-1-alkylthio)alkyl, aminoalkyl, alkylaminoalkyl, dialkylaminoalkyl, alkylsulfonylalkyl, alkylsulfinylalkyl, alkyl substituted with a dialkylsulfonium salt, cyanoalkyl, carbanylalkyl, carbalkoxyalkyl, carbalkoxyalkenyl, formylalkyl, dialkylaminoalkenyl, saturated and unsaturated heterocyclic radicals, selected from the group consisting of furyl, pyridyl, thienyl, thiiranyl, oxiranyl and aziridinyl and lower alkyl substituted with a saturated or unsaturated heterocyclic radical selected from the group consisting of furyl, pyridyl, thienyl, thiiranyl, oxiranyl and aziridinyl;

$R_1$ and $R_2$ are independently selected from alkyl, fluorinated methyl, and chlorofluorinated methyl radicals, provided that one of $R_1$ and $R_2$ must be a fluorinated methyl or chlorofluorinated methyl radical;

X is

where $R_3$ is as defined below; and Y is selected from the group consisting of

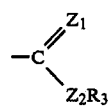

wherein $Z_1$ is selected from O and $NR_7$ where $R_7$ is selected from hydrogen and lower alkyl and wherein $Z_2$ is selected from O and S, and wherein $R_3$ in each occurrence is independently selected from hydrogen, alkyl $C_{1-4}$, alkenylalkyl $C_{3-4}$, haloalkyl $C_{1-4}$, cyanoalkyl, cyanoalkanykalkyl, alkynylalkyl $C_{3-4}$ provided that when $Z_1$ is O, $Z_2$ cannot be S;

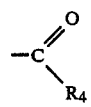

wherein $R_4$ is selected from hydrogen and halogen;

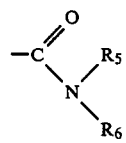

wherein $R_5$ and $R_6$ are independently selected from hydrogen, lower alkyl, and phenyl;

—$CH_2OH$; and

—C≡N.

2. A compound according to claim 1 wherein one of $R_1$ and $R_2$ is a trifluoromethyl radical and the other is a fluorinated methyl radical.

3. A compound according to claim 2 wherein Y is

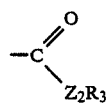

4. A compound according to claim 3 wherein R is selected from lower alkyl, lower alkenyl, lower alkenylalkyl, lower alkynyl, $C_{3-7}$ cycloalkyl, haloalkyl, and $C_{3-6}$ cycloalkanylalkyl.

5. A compound according to claim 3 wherein R is selected from alkoxyalkyl, benzyloxymethyl, dialkoxyalkyl, alkylthioalkyl, (1-alkoxy-1-alkylthio)-alkyl, and dialkylaminoalkyl.

6. A compound according to claim 2 wherein Y is —C≡N.

7. A compound according to claim 6 wherein R is selected from lower alkyl, lower alkenyl, lower alkenylalkyl, lower alkynyl, C$_{3-7}$ cycloalkyl, haloalkyl, and C$_{3-6}$ cycloalkanylalkyl.

8. A compound according to claim 6 wherein R is selected from alkoxyalkyl, benzyloxymethyl, dialkoxyalkyl, alkylthioalkyl, (1-alkoxy-1-alkylthio)-alkyl, and dialkylaminoalkyl.

9. A compound according to claim 1 wherein one of R$_1$ and R$_2$ is a trifluoromethyl radical and the other is an alkyl radical.

10. A compound according to claim 9 wherein Y is

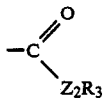

11. A compound according to claim 10 wherein R is selected from lower alkyl, lower alkenyl, lower alkenylalkyl, lower alkynyl, C$_{3-7}$ cycloalkyl, haloalkyl, and C$_{3-6}$ cycloalkanylalkyl.

12. A compound according to claim 10 wherein R is selected from alkoxyalkyl, benzyloxymethyl, dialkoxyalkyl, alkylthioalkyl, (1-alkoxy-1-alkylthio)-alkyl, and dialkylaminoalkyl.

13. A compound according to claim 9 wherein Y is —C≡N.

14. A compound according to claim 13 wherein R is selected from lower alkyl, lower alkenyl, lower alkenylalkyl, lower alkynyl, C$_{3-7}$ cycloalkyl, haloalkyl, and C$_{3-6}$ cycloalkanylalkyl.

15. A compound according to claim 13 wherein R is selected from alkoxyalkyl, benzyloxymethyl, dialkoxyalkyl, alkylthioalkyl, (1-alkoxy-1-alkylthio)-alkyl, and dialkylaminoalkyl.

16. A compound according to claim 1 wherein R$_1$ is trifluoromethyl, R$_2$ is selected from methyl, monofluoromethyl, and difluoromethyl, R is selected from isopropyl, cyclopropylmethyl, isobutyl, propyl, and Y is

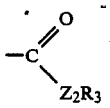

where Z$_2$ is O and R$_3$ is methyl or ethyl.

17. A compound according to claim 1 wherein R$_1$ is trifluoromethyl, R$_2$ is difluoromethyl, R is methylthiomethyl, and X and Y are

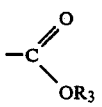

wherein R$_3$ in each occurrence is independently methyl or ethyl.

18. A herbicidal composition containing a carrier and a herbicidally effective amount of a compound represented by the structural formula

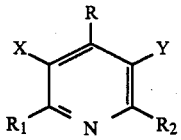

wherein:

R is selected from the group consisting of lower alkyl, lower alkenyl, lower alkynyl, lower alkenylalkyl, haloalkyl, haloalkenyl, C$_{3-7}$ cycloalkyl, C$_{3-6}$ cycloalkanylalkyl, phenyl, alkoxyalkyl, benzyloxymethyl, alkylthioalkyl, dialkoxyalkyl, (1-alkoxy-1-alkylthio)alkyl, aminoalkyl, alkylaminoalkyl, dialkylaminoalkyl, alkylsulfonylalkyl, alkylsulfinylalkyl, alkyl substituted with a dialkylsulfonium salt, cyanoalkyl, carbamylalkyl, carbalkoxyalkyl, carbalkoxyalkenyl, formylalkyl, dialkylaminoalkenyl, saturated and unsaturated heterocyclic radicals, selected from the group consisting of furyl, pyridyl, thienyl, thiiranyl, oxiranyl and aziridinyl and lower alkyl substituted with a saturated or unsaturated heterocyclic radical selected from the group consisting of furyl, pyridyl, thienyl, thiiranyl, oxiranyl and aziridinyl;

R$_1$ and R$_2$ are independently selected from alkyl, fluorinated methyl, and chlorofluorinated methyl radicals, provided that one of R$_1$ and R$_2$ must be fluorinated methyl or chlorofluorinated methyl radical;

X is

where R$_3$ is as defined below; and Y is selected from the group consisting of

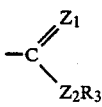

wherein Z$_1$ is selected from O and NR$_7$ where R$_7$ is selected from hydrogen and lower alkyl and wherein Z$_2$ is selected from O and S, wherein R$_3$ in each occurrence is independently selected from hydrogen, alkyl C$_{1-4}$, alkenylalkyl C$_{3-4}$, haloalkyl C$_{1-4}$, cyanoalkyl, cyanoalkanykalkyl, alkynylalkyl C$_{3-4}$ provided that when Z$_1$ is O, Z$_2$ cannot be S;

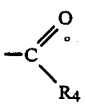

wherein R$_4$ is selected from hydrogen and halogen;

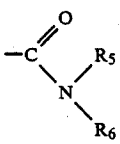

wherein R$_5$ and R$_6$ are independently selected from hydrogen, lower alkyl, and phenyl;

—CH$_2$OH; and

—C≡N.

19. A composition according to claim 18 wherein one of R$_1$ and R$_2$ is a trifluoromethyl radical and the other is a fluorinated methyl radical.

20. A composition according to claim 19 wherein Y is

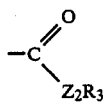

21. A composition according to claim 20 wherein R is selected from lower alkyl, lower alkenyl, lower alkenylalkyl, lower alkynyl, C$_{3-7}$ cycloalkyl, haloalkyl, and C$_{3-6}$ cycloalkanylalkyl.

22. A composition according to claim 20 wherein R is selected from alkoxyalkyl, benzyloxymethyl, dialkoxyalkyl, alkylthioalkyl, (1-alkoxy-1-alkylthio)-alkyl, and dialkylaminoalkyl.

23. A composition according to claim 19 wherein Y is —C≡N.

24. A composition according to claim 23 wherein R is selected from lower alkyl lower alkenyl, lower alkenylalkyl, lower alkynyl, C$_{3-7}$ cycloalkyl, haloalkyl, and C$_{3-6}$ cycloalkanylalkyl.

25. A composition according to claim 23 wherein R is selected from alkoxyalkyl, benzyloxymethyl, dialkoxyalkyl, alkylthioalkyl, (1-alkoxy-1-alkylthio)-alkyl, and dialkylaminoalkyl.

26. A composition according to claim 18 wherein one of R$_1$ and R$_2$ is a trifluoromethyl radical and the other is an alkyl radical.

27. A composition according to claim 26 wherein Y is

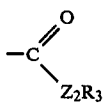

28. A composition according to claim 27 wherein R is selected from lower alkyl, lower alkenyl, lower alkenylalkyl, lower alkynyl, C$_{3-7}$ cycloalkyl, haloalkyl, and C$_{3-6}$ cycloalkanylalkyl.

29. A composition according to claim 27 wherein R is selected from alkoxyalkyl, benzyloxymethyl, dialkoxyalkyl, alkylthioalkyl, (1-alkoxy-1-alkylthio)-alkyl, and dialkylaminoalkyl.

30. A composition according to claim 26 wherein Y is —C≡N.

31. A composition according to claim 30 wherein R is selected from lower alkyl, lower alkenyl, lower alkenylalkyl, lower alkynyl, C$_{3-7}$ cycloalkyl, haloalkyl, and C$_{3-6}$ cycloalkanylalkyl.

32. A composition according to claim 30 wherein R is selected from alkoxyalkyl, benzyloxymethyl, dialkoxyalkyl, alkylthioalkyl, (1-alkoxy-1-alkylthio)-alkyl, and dialkylaminoalkyl.

33. A composition according to claim 18 wherein R$_1$ is trifluoromethyl, R$_2$ is selected from methyl, monofluoromethyl, and difluoromethyl, R is selected from isopropyl, cyclopropylmethyl, isobutyl, propyl, and Y is

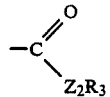

where Z$_3$ is O and R$_3$ is methyl or ethyl.

34. A composition according to claim 18 wherein R$_1$ is trifluoromethyl, R$_2$ is difluoromethyl, R is methylthiomethyl, and X and Y are

wherein R$_3$ in each occurrence is independently methyl or ethyl.

35. A herbicidal method comprising applying to the plant locus an effective amount of a compound represented by the structural formla

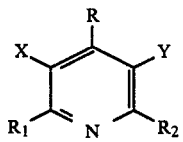

wherein:

R is selected from the group consisting of lower alkyl, lower alkenyl, lower alkynyl, lower alkenylalkyl, haloalkyl, haloalkenyl, C$_{3-7}$ cycloalkyl, C$_{3-6}$ cycloalkanylalkyl, phenyl, alkoxyalkyl, benzyloxymethyl, alkylthioalkyl, dialkoxyalkyl, (1-alkoxy-1-alkylthio)alkyl, aminoalkyl, alkylaminoalkyl, dialkylaminoalkyl, alkylsulfonylalkyl, alkylsulfinylalkyl, alkyl substituted with a dialkylsulfonium salt, cyanoalkyl, carbamylalkyl, carbalkoxyalkyl, carbalkoxyalkenyl, formylalkyl, dialkylaminoalkenyl, saturated and unsaturated heterocyclic radicals, selected from the group consisting of furyl, pyridyl, thienyl, thiiranyl, oxiranyl and aziridinyl and lower alkyl substituted with a saturated or unsaturated heterocyclic radical selected from the group consisting of furyl, pyridyl, thienyl, thiiranyl, oxiranyl and aziridinyl;

R$_1$ and R$_2$ are independently selected from alkyl, fluorinated methyl, and chlorofluorinated methyl radicals. provided that one of R$_1$ and R$_2$ must be fluorinated methyl or chlorofluorinated methyl radical;

X is

where R$_3$ is as defined below; and Y is selected from the group consisting of

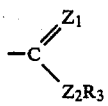

wherein Z$_1$ is selected from O and NR$_7$ where R$_7$ is selected from hydrogen and lower alkyl and wherein Z$_2$ is O, and wherein R$_3$ in each occurrence is independently selected from hydrogen, alkyl C$_{1-4}$, alkenylalkyl C$_{3-4}$, haloalkyl C$_{1-4}$, cyanoalkyl, cyanoalkanykalkyl, alkynylalkyl C$_{3-4}$ provided that when Z$_1$ is O, Z$_2$ cannot be S;

wherein R$_4$ is selected from hydrogen and halogen;

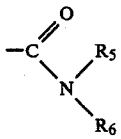

wherein R$_5$ and R$_6$ are independently selected from hydrogen, lower alkyl, and phenyl;

—CH$_2$OH; and

—C≡N.

36. A method according to claim 35 wherein one of R$_1$ and R$_2$ is a trifluoromethyl radical and the other is a fluorinated methyl radical.

37. A method according to claim 36 wherein Y is

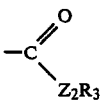

38. A method according to claim 37 wherein R is selected from lower alkyl, lower alkenyl, lower alkenylalkyl, lower alkynyl, C$_{3-7}$ cycloalkyl, haloalkyl, and C$_{3-6}$ cycloalkanylalkyl.

39. A method according to claim 37 wherein R is selected from alkoxyalkyl, benzyloxymethyl, dialkoxyalkyl, alkylthioalkyl, (1-alkoxy-1-alkylthio)-alkyl, and dialkylaminoalkyl.

40. A method according to claim 36 wherein Y is —C≡N.

41. A method according to claim 40 wherein R is selected from lower alkyl lower alkenyl, lower alkenylalkyl, lower alkynyl, C$_{3-7}$ cycloalkyl, haloalkyl, and C$_{3-6}$ cycloalkanylalkyl.

42. A method according to claim 40 wherein R is selected from alkoxyalkyl, benzyloxymethyl, dialkoxyalkyl, alkylthioalkyl, (1-alkoxy-1-alkylthio)-alkyl, and dialkylaminoalkyl.

43. A method according to claim 35 wherein one of R$_1$ and R$_2$ is a trifluoromethyl radical and the other is an alkyl radical.

44. A method according to claim 43 wherein Y is

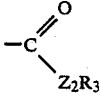

45. A method according to claim 44 wherein R is selected from lower alkyl, lower alkenyl, lower alkenylalkyl, lower alkynyl, C$_{3-7}$ cycloalkyl, haloalkyl, and C$_{3-6}$ cycloalkanylalkyl.

46. A method according to claim 44 wherein R is selected from alkoxyalkyl, benzyloxymethyl, dialkoxyalkyl, akylthioalkyl, (1-alkoxy-1-alkylthio)-alkyl, and dialkylaminoalkyl.

47. A method according to claim 43 wherein Y is —C≡N.

48. A method according to claim 47 wherein R is selected from lower alkyl, lower alkenyl, lower alkenylalkyl, lower alkynyl, C$_{3-7}$ cycloalkyl, haloalkyl, and C$_{3-6}$ cycloalkanylalkyl.

49. A method according to claim 47 wherein R is selected from alkoxyalkyl, benzyloxymethyl, dialkoxyalkyl, alkylthioalkyl, (1-alkoxy-1-alkylthio)-alkyl, and dialkylaminoalkyl.

50. A method according to claim 35 wherein R$_1$ is trifluoromethyl, R$_2$ is selected from methyl, monofluoromethyl, and difluoromethyl, R is selected from isopropyl, cyclopropylmethyl, isobutyl, propyl, and Y is

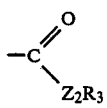

where Z$_2$ is O and R$_3$ is methyl or ethyl.

51. A method according to claim 35 wherein R$_1$ is trifluoromethyl, R$_2$ is difluoromethyl, R is methylthiomethyl, and X and Y are

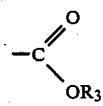

wherein R$_3$ in each occurrence is independently methyl or ethyl.

52. A compound according to claim 1 wherein R is selected from the group consisting of 2-methyl propyl, cyclopropylmethyl, and cyclobutyl.

53. A compound according to claim 52 wherein one of R$_1$ and R$_2$ is CF$_3$ and the other is CF$_2$H.

54. A compound according to claim 53 wherein X is

55. A compound according to claim 54 wherein Y is selected from the group consisting of

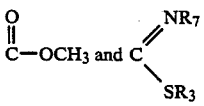

56. A compound according to claim 55 wherein R$_3$ and R$_7$ are CH$_3$.